United States Patent [19]
Lipsky et al.

[11] Patent Number: 5,616,458
[45] Date of Patent: Apr. 1, 1997

[54] TRIPTERYGIUM WILFORDII HOOK F EXTRACTS AND COMPONENTS, AND USES THEREOF

[75] Inventors: Peter E. Lipsky; Xue-Lian Tao; Jian Cai, all of Dallas, Tex.; William J. Kovacs; Nancy J. Olsen, both of Nashville, Tenn.

[73] Assignee: Board of Regents, University of TX System, Austin, Tex.

[21] Appl. No.: 455,906

[22] Filed: May 31, 1995

Related U.S. Application Data

[63] Continuation-in-part of Ser. No. 168,980, Dec. 17, 1993, which is a continuation-in-part of Ser. No. 862,836, Apr. 3, 1992, Pat. No. 5,294,443, which is a continuation-in-part of Ser. No. 494,113, Mar. 14, 1990, abandoned.

[51] Int. Cl.$^6$ ............... C12Q 1/00; G01N 33/53; A61K 31/74; A61K 35/78
[52] U.S. Cl. ............... 435/4; 435/7.5; 435/7.9; 424/78.05; 424/195.1; 514/469; 514/821; 514/825; 514/886
[58] Field of Search ............... 435/7.5, 7.9, 4; 424/195.1, 78.05; 514/469, 821, 825, 886

[56] References Cited

U.S. PATENT DOCUMENTS

| | | |
|---|---|---|
| 4,005,108 | 1/1977 | Kupchan et al. . |
| 4,241,536 | 12/1980 | Saint-Firmin . |
| 4,328,309 | 5/1982 | Chalmers et al. . |
| 5,192,817 | 3/1993 | Takaishi et al. . |
| 5,294,443 | 3/1994 | Lipsky et al. . |

OTHER PUBLICATIONS

Weijiang et al., "Studies on Diterpenoids from *Tripterygium wilfordii*," *Acta Academiae Medicinae Shanghai*, 13(4):272, 1986, published in China.
Kupchan et al., "Triptolide and Tripdiolide, Novel Antileukemic Diterpenoid Triepoxides from *Triptergium wilfordii*," *Journal of the American Chemical Society*, 94(20):7194–7195, 1972, published in USA.
Zhang et al., "Antineoplastic Action of Triptolide and its Effect on the Immunologic Functions in Mice," *Acta Pharmacologica Sinica*, 2(2):128–131, 1981, published in China.
Wenyan et al., "Triptergium in Dermatologic Therapy," *International Journal of Dermatology*, 24(3):152–157, 1985, published in USA.
Deng et al., "The Structure of Triptodihydroxy Acid Methyl Ester and Wilfortrine," *Chemical Abstracts*, 107:436, #55718y, 1987, published in Columbus, Ohio.
Wu et al., "The Crystal Structure of Triptophenolide Methyl Ether," *Chemical Abstracts*, 107:712, #96914c, 1987, published in Columbus, Ohio.
He et al., "Structures of Wilforgine, Wilforzine and Wilformine from *Tripterygium wilfordii*," *Chemical Abstracts*, 107:422, #130906p, 1987, published in Columbus, Ohio.
Deng et al., "The Isolation and Structure of Triptonoterpenol," *Chemical Abstracts*, 107:369, #112684k, 1987, published in Columbus, Ohio.

PCT search report dated 16 Aug. 1991 published in Europe.
Pu & Zhang, "Effects of Triptolide on T Lymphocyte Functions in Mice," *Chemical Abstracts, Pharmacology*, 112:45, #171972d, 1990, published Columbus, Ohio.
Bai et al., "*Tripterygium wilfordii* Hook F in Treatment of Rheumatoid Arthritis and Ankylosing Spondylitis," *Biological Abstracts*, 87(3), #29969, 1989, published in USA.
Zheng et al., "Immunosuppressive Effects of Wilfortrine and Euonine," *Chemical Abstracts*, 112(3):22, #16029h, 1990, published in Columbus, Ohio.
Zhang et al., "Antineoplastic Effect of Triptolide and its Effect on the Immunologic Functions in Mice," *Chemical Abstracts*, 95(9):102, #73690w, 1981, published in Columbus, Ohio.
Xia & Chen, "Alkaloids from Stems and Leaves of *Tripterygium wilfordii*," *Chemical Abstracts*, 113(25):38, #224305t, 1990, published in Columbus, Ohio.
*Tripterygium wilfordii* Hook Research Group, "Studies on Total Glycosides of *Tripterygium wilfordii* on Dermatoses," *Biological Abstract*, 79(9):762, #80151, 1985, published in USA.
Chang et al., "A Preliminary Study on the Immunosuppressive Activity of Mixed Glycoside of *T. wilfordii*," *Biological Abstracts*, 79(10), #89135, 1985, published in USA.
Li & Weir, "Radix *T. Wilfordii*: A Chinese Herbal Medicine with Potent Immunosuppressive Properties," *Biological Abstracts*, 90(7), #79317, 1990, published in USA.
Wang & Yuan, "A Tablet of *Tripterygium wilfordii* in Treating Lupus Erythematosus," *Chung Hsi I Chieh Ho Tsa Chih* (China), 9(7):389–407, 1989, published in China.
Xu et al., "Tripterygium in Dermatologic Therapy," *Int. J. Dermatol.*, 24(3):152–157, 1985, published in USA.
Su et al., "Comparative Clinical Study of Rheumatoid Arthritis Treated by Triptolide and an Ethyl Acetate Exract of *Tripterygium wilfordii*," *Chung Hsi I Chieh Ho Tsa Chih* (China), 10(3):131 & 144–146, 1990, published in China.

(List continued on next page.)

*Primary Examiner*—John W. Rollins
*Attorney, Agent, or Firm*—Denise L. Mayfield

[57] ABSTRACT

The present invention provides for the use of *Tripterygium wilfordii* Hook F extracts and purified components thereof in the treatment of inflammation or an immune disorder with concomitant lack of steroidal effect. Extracts of this plant (T2) bound to the glucocorticoid receptor and competitively inhibited glucocorticoid mediated cellular processes, such as dexamethasone binding to the glucocorticoid receptor, glucocorticoid mediated activation of target genes, dexamethasone dependent cellular growth, with concomitant inhibition of cyclooxygenase-2 induction and inflammatory processes such as the production of prostaglandin $E_2$. The T2 extract components triptolide and tripdiolide were effective inhibitors. The particular advantage provided by the methods herein is the treatment or prevention of inflammation and the concomitant lack of steroidal agonist effects and NSAID side effects. Conditions treatable by the present methods include inflammation and immune disorders including autoimmune disease.

6 Claims, 25 Drawing Sheets

OTHER PUBLICATIONS

Tao et al., "A Prospective, Controlled, Double-blind, Cross-over Study of *Tripterygium wilfordii* Hook F in Treatment of rheumatoid Arthritis," *Chin. Med. J.* [Engl] (China), 102(5):327–332, 1989, published in China.

Tao et al., "Effect of an Extract of the Chinese Herbal Remedy *Tripterygium wilfordii* Hook F on Human Immune Responsiveness," *Arthritis and Rheumatism*, 34(10):1274–1281, 1991, published in USA.

Chen et al., (1987) Clinical analysis of 10 cases of *Tripterygium wilfordii* Hook caused toxicity Symposium, "Clinical Application of *Tripterygium wilfordii* Hook," Hubei, China, published in China.

Zheng et al. (1983) "Studies on toxicity of total glycosides in *Tripterygium wilfordii*" *Acta. Med. Sinicae* 5(2):73, published in China.

Zheng et al. (1983) "Studies on pharmacological actions of total glycosides in *Tripterygium wilfordii* Hook F" *Acta. Acad. Med. Sinicae* 5:1, published in China.

Chang et al., (1984) "A preliminary study of the immunosuppressive activity of mixed glycosides of *Tripterygium wilfordii* Hook F" *Chinese J. Immunol.* 4:331, published in China.

Zheng et al. (1982) "Effect of the decoction of *Tripterygium wilfordii* Hook on immune functions" *Fujiang Med. J.* 4:222, published in China.

Zuo et al. (1986) "Different effect of *Tripterygium reglii* on T and B cell function" *Chinese J. Immunol.* 2:232, published in China.

Jia Li (1985) "Chemistry and pharmacology and clinical application of plants of Tripterygium family" *Yao Xue Tong Bao* 20:101, published in China.

Tao et al. (1987) "Prospective, controlled, double-blind, cross-over trial of T2 (polyglycosides extracted from *Tripterygium wilfordii* Hook F) in the treatment of rheumatoid arthritis" *Chinese J. Int. Med.* 26:399, published in China.

Tao et al. (1988) "Mechanism of treatment of rheumatoid arthritis with *Tripterygium wilfordii* Hook F I. Effect of T2 on secretion of total IgM and IgM–RF by PBMC" *Acta. Acad. Med. Sinicae* 10:361, published in China.

Hubei Study Group (1982) "Pharmacological study on the ethanol extract of *Tripterygium wilfordii* Hook F" *Zung Cao Yao* 13:27, published in China.

Wei et al. (1988) "Side effects of T2 in the treatment of 106 patients with glomerular diseases" *New Drug and It's Clinical Application* 1(6):37, published in China.

Jiang et al. (1987) "*Tripterygium wilfordii* Hook caused acute toxicity with kidney involvement in 17 cases" *Chinese J. Kidney Dis* 3(3):167, published in China.

Zhang, LS (1986) "Inhibitory effect of celastrol on murine lymphocyte proliferation" *Acta. Pharmacol. Sinicae* 7:85, published in China.

Kupchan, SM (1976) "Novel plant-derived tumor inhibitors and their mechanisms of action" *Cancer Treatment Reports* 60:1115, published in USA.

Zhang et al., (1986) "Studies on Diterpenoids from *Tripterygium wilfordii*," Shanghai Yike Da ue Xuebao 13(4):267–272, published in Chemical Abstracts, Columbus Ohio.

Kupchan et al. (1972), "Triptolide and Tripdiolide, Novel Antileukemic Diterpenoid Triepoxides from *Tripterygium wilfordii*," *J. Am. Chem. Soc.*, 94:7194–7195, published in USA.

Byers et al. (1990) "Patients with rheumatoid arthritis treated with a pan T-lymphocyte immunotoxin: phase II studies" *FASEB J* 4:A1855.

Goldberg et al. (1990) "Preliminary trial of an Anti–CD4 monoclonal antibody (MoAb)in rheumatoid arthritis (RA)" *Arthritis Rheum.* 33:S153.

Harris, E.D. (1990) "Rheumatoid Arthritis: Pathophysiology and implications for therapy" *N. Engl. J. Med.* 322:1277.

Horneff et al. (1991) "Treatment of rheumatoid arthritis with an anti–CD4 monoclonal antibody" *Arthritis Rheum.* 34:129.

June et al. (1990) "Increases in tyrosine phosphorylation are detectable before phospholipase C activation after T cell receptor stimulation" *J. Immunol.* 44:1591.

Kirkman et al. (1991) "Chimeric (human/mouse) CD7 monoclonal antibody treatment in rheumatoid arthritis" *Brit. J. Rheumatol.* 30 (Suppl 2):88.

Lipsky, P.E. (1991) "Rheumatoid Arthritis" In *Harrison's Principles of Internal Medicine*, J.D. Wilson et al. editors, McGraw Hill, Inc., New York, pp. 1437–1443.

Lu, Xiyu et al. The isolation and the structure of triptochlorolide (T4) from *Tripterygium wilfordii*. ACTH Academiae Medicinae Sinica 12(3):157, 1990.

Ma, Pengcheng et al. 16–hydroxytriptolide, a new active diterpene isolated from *Tripterygium wilfordii*. ACTA Pharmaceutica Sinica 26(10):759, 1991.

Minakuchi et al. (1990) "Delineation of the mechanisms of inhibition of human T cell activation by $PGE_2$" *J. Immunol.* 145:2616.

Moreland et al. (1991) "Treatment of refractory rheumatoid arthritis (RA) with a chimeric anti–CD4 monoclonal antibody" *Clin. Res.* 39:309A.

Mustelin et al. (1990) "T cell antigen receptor-mediated activation of phospholipase C requires tyrosine phosphorylation" *Science* 247:1584.

Pu et al. (1990) *Chem. Abtracts*, 112:45, abstract 171972d.

Racadot et al. (1991) "Immunologic follow-up of 13 patients with rheumatoid arthritis treated by anti–CD4 monoclonal antibodies" *Br. J. Rheum.* 30(suppl 2):88.

Reiter et al. (1991) "Treatment of rheumatoid arthritis with monoclonal CD4 antibody M–T151" *Arthritis Rheum.* 34:524.

Sewell et al. (1991) "Rapid improvement in refractory rheumatoid arthritis by an interleukin–2 receptor targeted immunotherapy" *Clin. Res.* 39:314A.

Strand et al. (1990) "Treatment of rheumatoid arthritis with an anti–CD5 immunoconjugate: clinical and immunologic findings and preliminary results of treatment" *Arthritis Rheum.* 33:S25.

Tao et al. (1991) "The effect of an extract of Chinese hebal remedy *Tripterygium wilfordii* Hook F on human immune responses" *Arthritis & Rheum.* 34:1274.

Wassmer et al. (1990) "Therapy of rheumatoid arthritis with CD4 monoclonal antibodies" *Arthritis Rheum.* 33:2153.

Wendling et al. (1991) "Therapeutic use of monoclonal anti–CD4 antibody in RA" *J. Rheumatol.* 18:325.

Zhang XY et al. (1992) "Prolonged survival of MRL–lpr/1pr mice treated with *Tripterygium wilfordii* Hook F," *Clinical Immunopathol* 62:66–71.

Adler et al., "Steroid Receptor–Mediated Inhibition of Rat Prolactin Gene Expression Does Not Require the Receptor DNA–Binding Domain," *Cell*, 52:685–695, 1988.

Agarwal et al., "Glucocorticoid antagonists," *FEBS Letter*, 217(2):221–226, 1987.

Akerblom et al., "Negative Regulation by Glucocorticoids Through Interference with a cAMP Responsive Enhancer," *Science*, 350–353, 1988.

Beato, "Gene Regulation by Steroid Hormones," *Cell*, 56:335–344, 1989.

Cai et al., "High Performance Liquid Chromatographic Determination of Triptolide and Tripdiolide in an Ethyl Acetate Extract of *Tripterygium wilfordii Hook F*," *Journal of Liquid Chromatography*, 17(20):4479–4487, 1994.

Evans, "The Steroid and Thyroid Hormone Receptor Superfamily," *Science*, 240:889–895, 1988.

Jonat et al., "Antitumor Promotion and Antiinflammation: Down–Modulation of AP–1 (Fos/Jun) Activity by Glucocorticoid Hormone," *Cell*, 62:1189–1204, 1990.

Tao et al., "The Identity of Immunosuppressive Components of the Ethyl Acetate Extract and Chloroform Methanol Extract (T2) of Tripterygium wilfordii Hook. F," *The Journal of Pharmacology and Experimental Therapeutics*, 272(3):1305–1312, 1995.

Schule et al., "Functional Antagonism between Oncoprotein c–Jun and the Glucocorticoid Receptor," *Cell*, 62:1217–1226, 1990.

Wahli and Martinez, "Superfamily of steroid nuclear receptors: positive and negative regulators of gene expression." *The FASEB Journal*, 5:2243–2249, 1991.

Pei, et al., Zhongguo Yoalixue Tongboa, vol. 9(1), pp. 68–72 (1993).

Pei, et al., Zhongguo Yoalixue Tongboa, vol. 14(3), pp. 238–242 (1993).

1, R = H
2, R = OH

1, R = OH
2, R = Me

*TRIPTERYGIUM WILFORDII* HOOK F EXTRACTS AND COMPONENTS, AND USES THEREOF

The government has rights in the invention developed in parent applications, U.S. Ser. Nos. 07/862,836 (filed Apr. 3, 1992) and 07/494,113 (filed Mar. 14, 1990), as research relevant to the development thereof was supported by a grant from the United States government, NIH grant AR-36169.

This application is a continuation-in-part application of U.S. Ser. No. 08/168,980 filed Dec. 17, 1993. U.S. Ser. No. 08/168,980 is a continuation-in-part application of U.S. Ser. No. 07/862,836 filed Apr. 3, 1992, since issued as U.S. Pat. No. 5,294,443 on Mar. 15, 1994. U.S. Ser. No. 07/862,836 was a continuation-in-part application of U.S. Ser. No. 07/494,113 filed Mar. 14, 1990, since abandoned. These applications and U.S. Patent are incorporated by reference herein.

BACKGROUND OF THE INVENTION

Rheumatoid arthritis (RA) is a chronic inflammatory disease of uncertain etiology. Since the cause is unknown, treatment has been directed at suppressing the signs and symptoms of chronic inflammation. Although many agents have been documented to decrease pain and swelling temporarily, none has been shown to have a major impact on the course of the disease. While therapeutic modalities have been developed for treatment of this disease[1-4], uniform and persistent suppression of this condition has not been reported. Although current approaches remain promising, alternative means of drug development seem warranted and could yield not only new and effective treatment modalities, but also provide new insights into disease pathogenesis that could serve as the basis of future therapeutic innovations.

An area to search for new therapeutic interventions for different forms of arthritis, and particularly RA and other autoimmune diseases, is that of traditional Chinese medicines. One of these traditional medicines is from *Tripterygium wilfordii* Hook F, a shrub-like vine from the Celastraceae family [5]. *Tripterygium wilfordii* Hook F is known to contain a number of constituents, some of which appear to be toxic [6]. It is known that the leaves, stem, flowers, and the skin of the roots are poisonous and that ingestion can cause death [7-9]. In contrast, the woody portion of the roots of the plant is much less toxic. An extract of *Tripterygium wilfordii* Hook F prepared from the root of the plant, designated $T_2$, has been described in the Chinese literature for the treatment of autoimmune diseases[10-26]. The preparation appeared to contain therapeutic components, and to have a reduced toxicity compared to other available preparations of the plant.

The $T_2$ extract has been evaluated in a double-blind placebo controlled cross-over study involving 70 RA patients, these patients having had a mean duration of RA of 6 years [10-11]. Significant improvement in a variety of clinical parameters, particularly ESR, CRP, and Rheumatoid factor titers, was noted after 12 weeks of therapy in the experimental group compared with either baseline measurements or the placebo treated group. Of the patients treated, 82–93% noted improvement in different clinical criteria or laboratory correlates of inflammation. An immunosuppressive activity of $T_2$ may be inferred from the finding that treatment induced inhibition of the production of IgM and IgM rheumatoid factor by the patients' peripheral blood mononuclear cells in vitro[7]. Toxicity, which consisted primarily of skin rash, gastrointestinal complaints and amenorrhea, was reportedly of a generally mild nature, and reversible with cessation of therapy.

The Chinese experience suggested that a daily dosage of 0.8–1.5 mg/kg of $T_2$ was relatively safe and effective. Acute and chronic toxicity studies have been carried out with $T_2$ in China using a variety of animal models. The $LD_{50}$ of $T_2$ in mice was found to be 159.7±14.3 mg/kg[27]. The major chronic toxicity noted in rats administered 30 mg/kg for 90 days was azoospermia and decrease in testicular weight[27]. Lower dosages of $T_2$ did not cause decreases in testicular weight. The toxicity studies, therefore, suggested that $T_2$ exhibited a reasonable safety index and should be able to be administered to patients safely.

Research has begun in China to determine the spectrum of activity of various preparations of *T. wilfordii*. According to the reported results of these studies, extracts of TwHF were able to inhibit E-rosette formation by guinea pig T cells, mitogen induced IL-2 production by mouse T cells, and antigen stimulated migration of rat lymphocytes[28, 29]. Components of *T. wilfordii* hook F known as triptonide and triptolide have been reported to inhibit the proliferation of lymph cells induced by concanavalin A[30]. Chloroform/ethanol extracts of the plant, referred to as $T_2$ in the literature, have been described as having significant activity in vivo against certain mouse leukemias and in vitro against cells derived from human carcinomas[31]. The capacity of $T_2$ to suppress a number of animal models of autoimmune disease, including adjuvant arthritis and experimental allergic encephalomyelitis, has been reported[28-29, 32-36]. Large concentrations of $T_2$ preparations (30 mg/kg) have been reported to suppress delayed-type hypersensitivity reactivity in mice and may also suppress graft-versus-host disease, as well as skin and heart allograft rejection[6,32]. It remains unclear whether lower, more pharmacologically appropriate concentrations would also exert therapeutic effects in these animals, however.

The $T_2$ examined in the Chinese literature is a crude extract containing a mixture of materials, including various glycosides, alkaloids, and diterpenoids. The active principle, however, has not yet been identified. A few components have been purified, including triptolide, wilfordine, and related compounds, but no particular purified component which accounts for the therapeutic or immunosuppressive activity of $T_2$ exists[40]. High concentrations of triptolide were reported to suppress B and T lymphocyte proliferation and interleukin-2 production by mouse spleen cells[41]. However, the concentrations of the $T_2$ used were sufficiently high that significant nonspecific toxicity undoubtedly occurred.

A number of pharmacologic agents have been used to treat rheumatoid arthritis and other inflammatory conditions. Among these are non-steroidal anti-inflammatory drugs (NSAIDS) and glucocorticoids. A major aspect of the mechanism of action of nonsteroidal anti-inflammatory drugs is generally thought to be the inhibition of cyclooxygenase, the enzyme responsible for the biosynthesis of some prostaglandins and certain related autacoids. This inhibition is dependent upon the drug reaching the cyclooxygenase enzyme, indicating that the mode of action is at the level of interaction with the enzyme protein itself. For example, acetaminophen can block the enzyme only in an environment that is low in peroxides which may explain its poor anti-inflammatory activity since sites of inflammation usually contain high concentrations of peroxides generated by leukocytes. Aspirin acetylates a serine at or near the active site of cyclooxygenase, inhibiting the enzymatic activity. The most common unwanted side-effect of NSAIDS and other aspirin-like drugs is a propensity to induce gastric or intestinal ulceration. More serious side-effects, such as anemia from resultant blood loss, may also sometimes occur.

Glucocorticoids have the capacity to prevent or suppress the development of the manifestations of inflammation. They are also of immense value in treating diseases that result from undesirable immune reactions. The immunosuppressive and anti-inflammatory actions of the glucocorticoids are inextricably linked because they both result in large part from inhibition of specific functions of leukocytes, in particular, inhibition of lymphokines.

Two categories of toxic effects are observed in the therapeutic use of adrenocorticosteroids[76]: those resulting from withdrawal and those resulting from continued use of large doses. Acute adrenal insufficiency results from too-rapid withdrawal of these drugs. Prolonged therapy with corticosteroids may result in suppression of pituitary-adrenal function that can be slow in returning to normal. Further complications resulting from prolonged therapy with corticosteroids are: fluid and electrolyte disturbances; hypertension; hyperglycemia and glycosuria; increased susceptibility to infections; including tuberculosis; peptic ulcers, which may bleed or perforate; osteoporosis; a characteristic myopathy; behavioral disturbances; posterior subcapsular cataracts; arrest of growth; and Cushing's habitus, consisting of "moon face", "buffalo hump," enlargement of supraclavicular fat pads, "central obesity," striae, ecchymoses, acne, and hirsutism.

An object of the present invention is to provide preparations of *T. wilfordii* Hook F, and isolated components thereof, for the treatment of inflammation and for immunosuppression without steroidal agonist effect. Current NSAID treatment modalities are accompanied by significantly undesirable side-effects. Therefore, agents that have the anti-inflammatory effects of NSAIDS without the side effects would be of great benefit. A second object of the present invention is to suppress the production of prostaglandins and other related autocoids without encountering the side effects of common NSAIDS. Accomplishment of these objectives will provide improved methods for treating inflammation, and immunosuppression, such as in the treatment of autoimmune disease, and particularly rheumatoid arthritis.

SUMMARY OF THE INVENTION

The present invention provides a method for treating inflammation or an immune disease in a subject while concurrently providing a steroid-sparing effect. These methods also limit, and in some cases essentially avoid, side effects associated with administration of NSAIDS. The method comprises the step of administering to the subject a pharmacologically active amount of a *Tripterygium wilfordii* Hook F root preparation to the subject, the preparation having anti-inflammatory and immunosuppressive pharmacological activity.

The *T. wilfordii* purified preparation is obtained by a process comprising extracting woody portions of *Tripterygium wilfordii* Hook F root, in most embodiments skinless root or root wherein at least some or most of the skin has been removed, to provide a preparation with reduced, or at least without substantial cellular toxicity, as compared to crude preparations that have not been purified or otherwise extracted apart from contaminating components. The methods described as part of the present invention employ *T. wilfordii* preparations that are observed to have glucocorticoid receptor binding activity. Glucocorticoid receptors are recognized by those of ordinary skill in the art as important in a number of pathologies. Thus, the methods are intended to encompass the use of these *T. wilfordii* components, in their isolated and purified form, that demonstrate this unique glucocorticoid receptor binding activity. Naturally derived and synthetically produced preparations of said components of the *T. wilfordii* may therefore be efficaciously used in the practice of the described methods. The glucocorticoid receptor binding active components of *T. wilfordii* have been characterized in root preparations, and may also exist in other parts of the plant. Intended within the meaning of the glucocorticoid receptor binding components of *T. wilfordii* are therefore those components, or pharmacologically active portions or fragments of those components, that bind glucocorticoid receptor. These components may be further characterized as suppressing inflammation and immune responses without or with minimal steroidal agonist effects and/or without, or with minimal NSAID effects.

The immune disease may be an autoimmune disease, such as rheumatoid arthritis, systemic lupus erythematosus, or psoriasis. The treatment of inflammation according to the present methods provides inhibition of a cyclooxygenase-2 dependent inflammatory process whereas the method of immunosuppression relates to suppression of interleukin-2 and of interferon γ production. Both of these effects relate to the capacity of components of TwHF to bind to the glucocorticoid receptor and inhibit transcription of genes with pro-inflammatory or immunoenhancing activity.

As used in the description of the present invention, the term "steroid sparing effect" is also defined as reducing the amount of steroid, such as prednisone, capable of providing a beneficial pharmacological effect of the steroid. For example, upon treatment with the described preparations, patients receiving prednisone treatments may be maintained on lower doses of the prednisone without significant loss of the pharmacological activity observed at the higher, initial doses of the steroid. This phenomenon is exemplified in the data presented at Table 13, in patients receiving the steroid prednisone. Thus, the "steroid-sparing effect" in the context of the present invention may also be described as the avoidance of commonly recognized steroid-related side effects, such as induction of glucose intolerance, osteoporosis, weight gain or a combination of these. This phenomenon may also relate to the absence of steroid agonist activity of a component(s) of the *T. wilfordii* preparation.

As also used in the description of the invention, the "woody" portion of the root is a portion of the root that is skinless, or without skin. Cellular toxicity as used in the present disclosure is measured by the induction of cell death, interleukin-2 receptor expression, cellular signaling activity, or a combination of one or more of these effects. Cellular signaling activity relates to inositol triphosphate production, diacylglycerol generation, translocation of protein kinase C, protein tyrosine kinase activity, or a combination of these activities.

An embodiment of the invention is a method for inhibiting cyclooxygenase-2 induction in a subject. The method comprises administering to the subject a pharmacologically active amount of a *Tripterygium wilfordii* Hook F root preparation, or a pharmacologically active component thereof, capable of binding glucocorticoid receptor. In this method, cyclooxygenase-1 activity is substantially unaffected. Inhibiting cyclooxygenase-2 induction inhibits the synthesis of a prostaglandin, an autacoid, or a cytokine inhibited by glucocorticoids, for example.

Constitutive production of prostaglandin and related autocoids is catalyzed by cyclooxygenase-1. Cyclooxygenase is found in many cells. Inhibition of this enzyme has been associated at least in part with side effects observed with treatment that includes NSAIDS. During inflammation and after stimulation, inflammatory cells, such as macrophage, transcribe a second gene and produce a new enzyme, cyclooxygenase-2, that accounts for much of the prostaglandin production at inflammatory sites. NSAIDS also inhibit this enzyme. Steroids (and T2) inhibit transcription of the gene for cyclooxygenase-2 while cyclooxygenase-1 activity is substantially unaffected. Therefore, they have the anti-inflammatory effects of NSAIDS but not the toxicity.

The cyclooxygenase-2 dependent inflammatory process may be the synthesis of a prostaglandin or the synthesis of a related autacoid. The additional corticosteroid-like immunosuppressive activities may be the synthesis of a cytokine inhibited by glucocorticoids, such as IL-2 or interferon $\gamma$, and may be related to a process of an autoimmune disease, such as, for example, rheumatoid arthritis, systemic lupus erythematosus or psoriasis.

Normally, when a glucocorticoid binds the glucocorticoid receptor, the bound complex induces the transcription of those genes activated by the glucocorticoid-receptor complex. The present inventors have shown herein that the TwHF extract, and components thereof, bind the glucocorticoid receptor, but do not activate steroid sensitive genes. Consequently, the genes that would normally be activated by that complex are not activated. Therefore, the related undesirable effects of steroid treatment are avoided by treatment with TwHF extract. Among the genes clearly shown by the present inventors to be inhibited by TwHF extracts are the IL-2 gene, the interferon $\gamma$ and the cyclooxygenase-2 genes. This provides a still further aspect of the invention as a method for inhibiting both immune reactions and inflammatory responses. Specific methods for inhibiting glucocorticoid and receptor complexing with the TwHF extract preparations are also hereby disclosed. The components of TwHF bind to the glucocorticoid receptor and that complex inhibits transcription of certain genes such as IL-2, IFN $\gamma$ and COX-2. However, unlike the complex of dexamethasone (a corticosteroid) and the glucocorticoid receptor, the complex of TwHF components and the glucocorticoid receptor does not activate genes that are driven by glucocorticoid response elements.

The undesired glucocorticoid receptor-dependent processes whose activation is avoided in the present invention may be induction of glucose intolerance, osteoporosis, or weight gain, suppression of pituitary-adrenal function, fluid or electrolyte disturbance, hypertension, hyperglycemia, glycosuria, susceptibility to infections, peptic ulcer, osteoporosis, myopathy, behavioral disturbance, posterior subcapsular cataracts, arrest of growth, or Cushing's habitus. In fact, all of the various hormone actions of glucocorticoids are driven by glucocorticoid response elements that regulate gene transcription.

The preparation may be a chloroform-methanol extract, a chloroform-ethanol extract, an ethanol, or an ethyl acetate extract of the woody portion of the *Tripterygium wilfordii* Hook F root. Preferably, the extract is an ethyl acetate extract and, most preferably, the extract is obtained from an ethanol extraction followed by an ethyl acetate extraction. The preparation may consist essentially of tripdiolide, triptolide, wilforonide, or related compounds of the extract that have the described biologic activity, or a compound synthesized having the basic triptolide structure that has triptolide activity, and the pharmacologically active amount may be about 30–600 mg/day, preferably about 50 mg/day to about 100 mg/day, or in some applications, about 60 mg/day. However, more or less of any of these doses may be clinically appropriate depending on the needs and progress of the particular patient or condition being treated and the evaluation of the attending physician.

The pharmacologically active amount of the preparation of the *Tripterygium wilfordii* Hook F root provided by the present invention is demonstrated by its $LD_{50}$ in mice, which is greater than about 860 mg/kg. Expressed as a range, the $LD_{50}$ of the preparation is between about 860 mg/kg to 1300 mg/kg. As demonstrated by the inventors, the EA extract produced in Texas is demonstrated to have an $LD_{50}$, more preferably, of about 1250 mg/kg. The $LD_{50}$ of the preparation is much higher than that observed with other TwHF preparations, as shown herein, and therefore, the present preparation is considerably less toxic (i.e., requiring higher doses to kill). This highlights the additional advantage of the present preparations as more pharmacologically acceptable.

The *T. wilfordii* preparation is further defined as having a therapeutic activity:toxic index ratio greater than about $2.6 \times 10^{-3}$, or preferably, from about $2.6 \times 10^{-3}$ to $4.5 \times 10^{-3}$ or more preferably, about $4.5 \times 10^{-3}$. The therapeutic activity:toxic index ratio is calculated from an $ID_{50}$ in vitro T-cell proliferation/$LD_{50}$ ratio.

The *Tripterygium wilfordii* Hook F preparation of the present method is also described as having less than about 1.3 µg/mg triptolide or preferably, about 0.2–1.3 µg/mg triptolide, or more preferably, about 0.2 µg/mg triptolide. While the preparation may be obtained by any means of chemical extraction techniques that yield a product having the described therapeutic activity:toxic index ratio and triptolide concentration, those techniques most preferred are ethyl acetate extraction of the root or by an ethanol extraction followed by an ethyl acetate extraction of the root.

In a preferred embodiment of the above described method, the preparation of the *Tripterygium wilfordii* Hook F root extract is obtained by a process comprising the steps of i) obtaining woody portions of roots of a *Tripterygium wilfordii* Hook F plant; and ii) extracting the woody portions with a solvent to produce a *Tripterygium wilfordii* Hook F preparation, wherein the preparation has less than about 1.3 µg/mg triptolide. The solvent is preferably ethyl acetate. Most preferably, the extracting step includes extracting with a first solvent and a second solvent where the first solvent is ethanol and the second solvent is ethyl acetate.

In a most preferred embodiment of the present invention, the *Tripterygium wilfordii* Hook F preparation has a therapeutic activity:toxic index ratio greater than about $2.6 \times 10^{-3}$, and the preparation is obtained by a process comprising the steps of i) obtaining woody portions of roots of a *Tripterygium wilfordii* Hook F plant and removing the skin; ii) extracting the woody portions with ethanol to produce an ethanol extract; and iii) extracting the ethanol extract with ethyl acetate to form a *Tripterygium wilfordii* Hook F preparation. The preparation has a therapeutic activity:toxic index ratio greater than about $2.6 \times 10^{-3}$ and an $LD_{50}$ in mice of greater than about 860 mg/kg, and less than about 1.3 µg/mg triptolide. In this embodiment of the present invention, the woody portions of the skinned roots are dried to form a dried woody portion; the dried woody portion is ground to form a powder; and the powder is extracted with ethanol to produce an ethanol extract; following the obtaining step aforedescribed. Most preferably, the woody portions of the root are to be dried under open sunlight.

Methods for treating inflammation, an immune disease, or rheumatoid arthritis without substantially activating a steroid-dependent gene in a patient are a further embodiments of the present invention. The method comprises administering about 30 to about 600 mg/day of a *Tripterygium wilfordii* Hook F root extract preparation having an $LD_{50}$ in mice of greater than about 860 mg/kg to the patient, wherein the preparation contains less than about 1.3 µg/mg triptolide and wherein the preparation binds to the glucocorticoid-receptor and thereby exerts anti-inflammatory and immunosuppressive activity.

A method for inhibiting glucocorticoid responsive genes, such as an interleukin-2 gene, an interferon γ gene and a cyclooxygenase-2 gene, is a further aspect of the present invention. Each of these genes is downregulated by a glucocorticoid receptor-binding molecular complex. Suppression of all pro-inflammatory or immune enhancing genes suppressed by glucocorticoids is envisioned by the present inventors. The method comprises the step of administering the above described preparation of *Tripterygium wilfordii* Hook F root extract in a pharmacologically active amount. The pharmacologically active amount is as herein described.

A method of reducing progesterone activity comprising the administration of the above described TwHF preparation is a further aspect of the present invention. The reduction of progesterone activity is useful for birth control, for example, or as a "morning-after" treatment. In addition, this approach should be useful as an abortifacient.

A further embodiment of the present invention is a method for determining the ability of a candidate substance to bind the glucocorticoid receptor in a competitive binding assay in the presence of TwHF preparation, or a glucocorticoid receptor binding component thereof. The method includes generally the steps of admixing a candidate substance with a glucocorticoid receptor in the presence of TwHF preparation or a glucocorticoid receptor binding component thereof, and determining binding of the candidate substance to the glucocorticoid receptor. In this method, the glucocorticoid receptor may be from a human skin fibroblast preparation; the glucocorticoid receptor binding component may be triptolide, tripdiolide or wilforonide; the glucocorticoid receptor is preferably conjugated to a label, such as an enzymatic, chemical, or a radioactive label. A preferred label is avidin/biotin.

Where it is desired to select among candidate substances for those which, like TwHF, do not activate steroid responsive genes, the candidate substances that exhibit glucocorticoid receptor binding activity would further be screened to identify those which do not activate steroid responsive gene expression. In so doing, other substances having the glucocorticoid receptor binding activity of TwHF, or its active components, that also avoid steroid-related side effects, may be identified.

A further embodiment of the invention is a method of selecting a substance for treating inflammation or immune disease comprising the steps of admixing a candidate substance with a glucocorticoid receptor in the presence of TwHF preparation or a glucocorticoid receptor binding component thereof, determining binding of the candidate substance to the glucocorticoid receptor, selecting a candidate substance having binding affinity for the glucocorticoid receptor, determining activity of the selected candidate substance for inducing steroid responsive gene expression, and selecting the candidate substance being inactive for inducing steroid responsive gene expression. The second determining step may be carried out using a reporter gene construct under regulatory control of asteroid responsive element, for example, the steroid responsive element from the MMTV long terminal repeat. The reporter gene may be the luciferase gene, the chloramphenicol acetyltransferase gene, or the β-galactosidase gene, for example. One of skill in the art upon reading the present disclosure would know of similar reporter gene constructs usable in the present invention.

Another embodiment of the invention is a method of blocking gamma interferon production in a subject. The method comprises administering to the subject a pharmacologically active amount of a *Tripterygium wilfordii* Hook F root preparation, or a pharmacologically active component thereof, capable of blocking gamma interferon production. A method of inhibiting interleukin-2 gene transcription in a subject is also an embodiment of the invention. The method comprises administering to the subject a pharmacologically active amount of a *Tripterygium wilfordii* Hook F root preparation, or a pharmacologically active component thereof, capable of inhibiting interleukin-2 gene transcription.

Following long-standing convention of patent law practice, case law, and claim construction, the words "a" and "an" denote "one or more", where they appear in the specification, including the claims.

The following abbreviations are used throughout the description of the present invention.
CRP=C reactive protein
DAG=diacylglycerol
ESR=erythrocyte sedimentation rate
FACS=fluorescence-activated cell sorter
GR=glucocorticoid receptor
Ig=immunoglobulin
IL-2=interleukin-2
IL-2R=interleukin-2 receptor
IP=phosphatidyl inositol triphosphate
MAb=monoclonal antibodies
MMTV=mouse mammary tumor virus
NHS=normal human serum
PBMC=peripheral blood mononuclear cells
PDB=phorbol dibutyrate
PHA=phytohemagglutinin
PMA=phorbol 12-myristate 13-acetate
PKC=protein kinase C
RA=rheumatoid arthritis
SA=formalinized Staphylococcus aureus
SK=streptokinase
SRBC=sheep red blood cells
$T_2$=a chloroform/methanol extract from the woody portion of *Tripterygium wilfordii* Hook F
TT=tetanus toxoid
TwHF or TWF=*Tripterygium wilfordii* Hook F

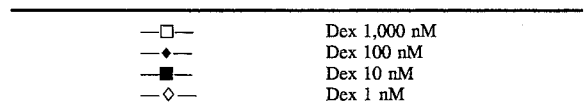

| | |
|---|---|
| —□— | Dex 1,000 nM |
| —♦— | Dex 100 nM |
| —■— | Dex 10 nM |
| —◊— | Dex 1 nM |

Figure 26:
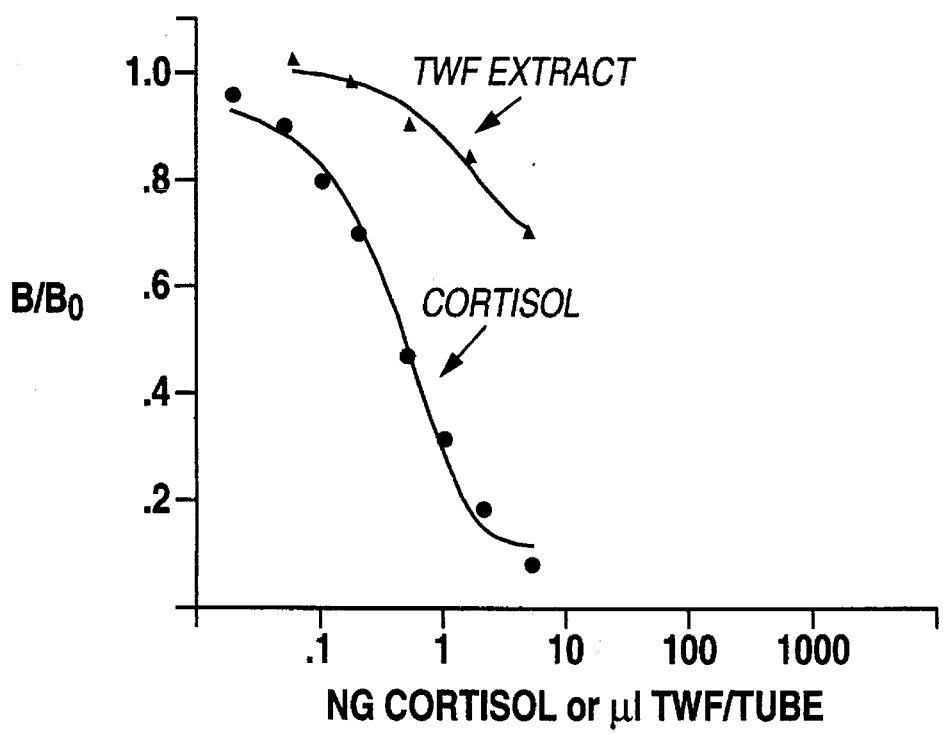

FIG. 26. Cortisol RIA with a novel A ring directed anti-cortisol antibody detects immunoreactivity in TwHF extract. Data are expressed as the fraction of radioactive cortisol tracer bound to antibody (B/B$_o$) as a function of added cortisol or TwHF. The TwHF displacement curve is not parallel to that of authentic cortisol, but some cross reactivity may exist.

Figure 27:
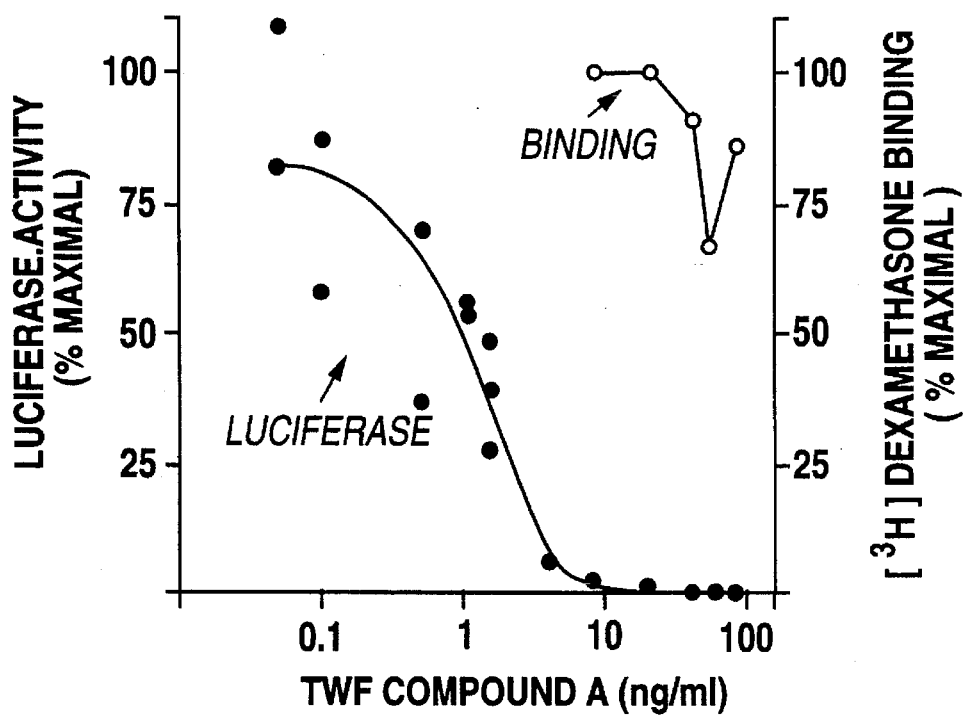

FIG. 27. Dose response curves for the TwHF compound A effect on GR ligand binding activity (as for FIG. 22) and GR-mediated target gene activation (as for FIG. 23). Data are shown as % maximal binding or activity as a function of TwHF concentration (log scale).

Figure 28:
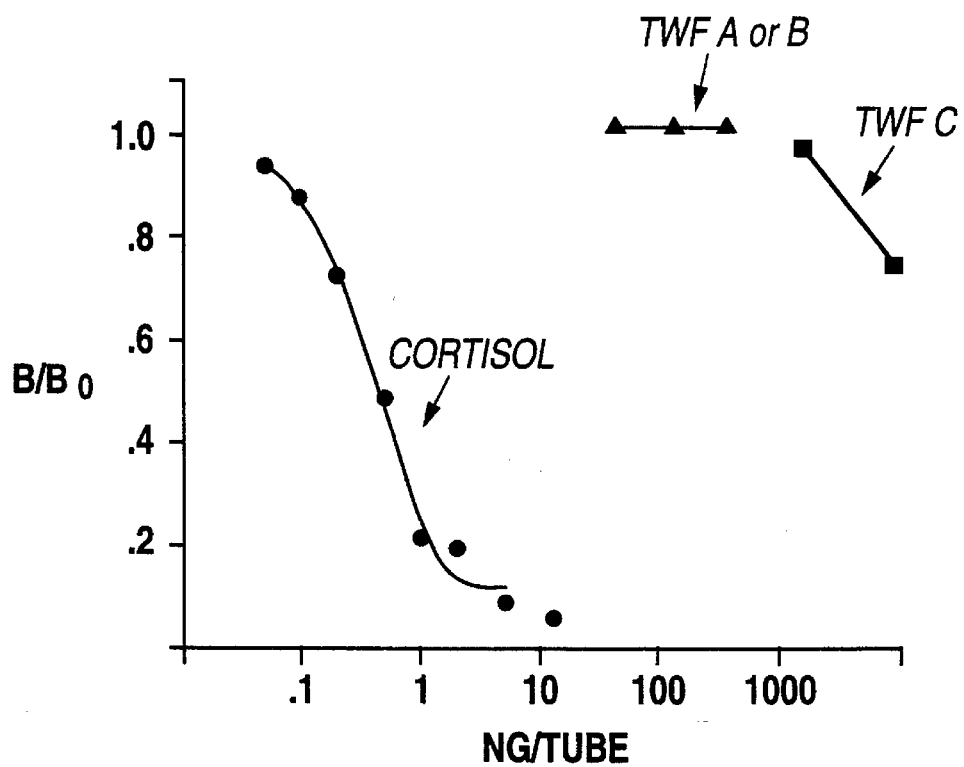

FIG. 28. Cortisol RIA with A ring-directed antibody fails to detect cortisol-like immunoreactivity in TwHF purified compounds A and B (triptolide and tripdiolide, respectively). Compound C (triptophenolide) may have low affinity immunoreactivity.

FIG. 29A, FIG. 29B, FIG. 29C and FIG. 29D. The extract of TwHF and purified components inhibit endotoxin induced PGE$_2$ production by human peripheral blood monocytes, RU 486 is tested in FIG. 29D.

Figure 30:
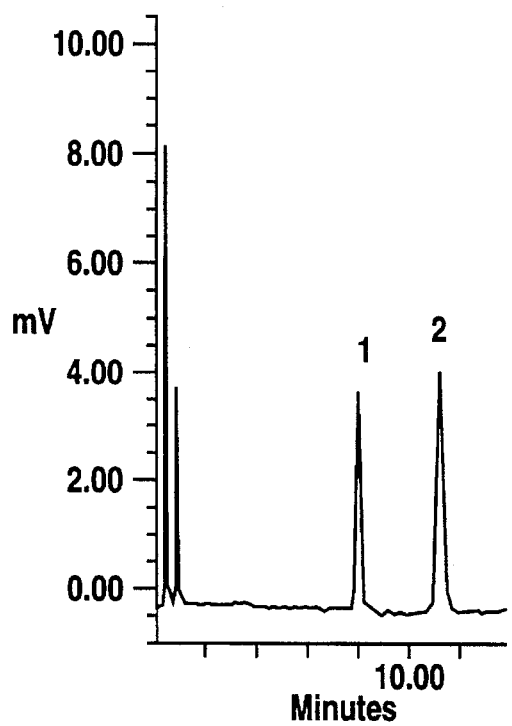

FIG. 30. Chromatogram of triptolide and acetophenone. Peaks: 1=acetophenone; 2=triptolide. Conditions: Nova-Pak C18 stainless steel column (150 mm×3.9 mm I.D.); mobile phase, acetonitrile-water (19:81); flow-rate, 1.5 ml/min.; UV monitor at 214 nm; sample volume 10 ul.

Figure 31:
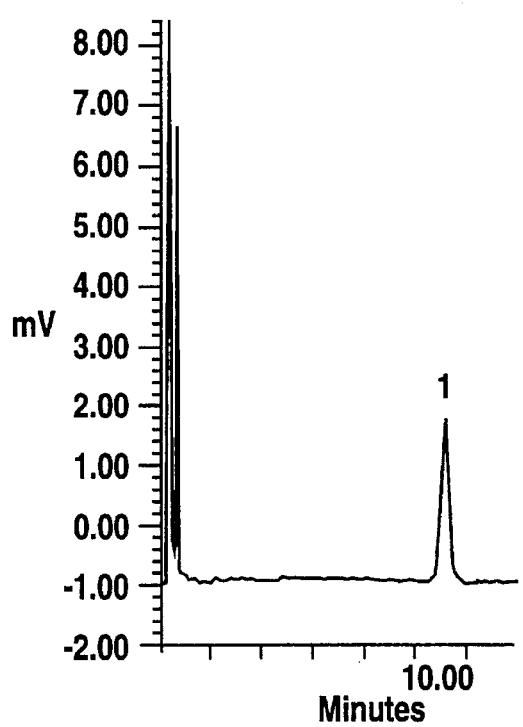

FIG. 31. Chromatogram of tripdiolide. Peak: 1=tripdiolide. Mobile phase acetonitrile-water (11:89); flow-rate, 2.0 mL/min. Other conditions as in FIG. 30.

Figure 32:
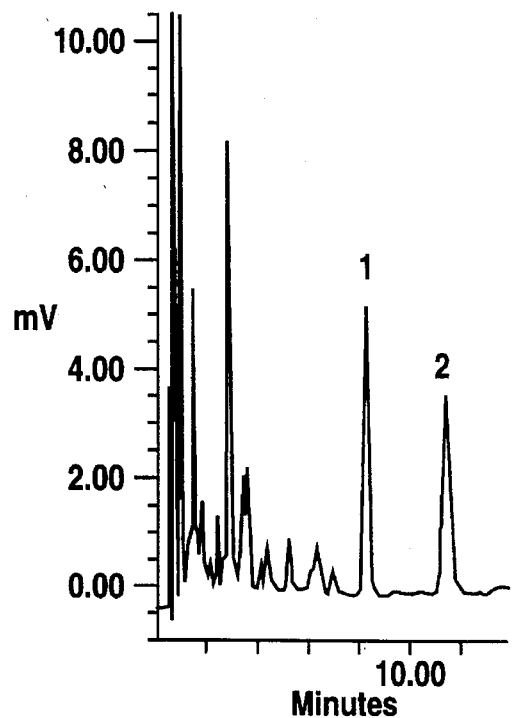

FIG. 32. Chromatogram of the extract of *Tripterygium wilfordii* Hook F. with the internal standard for the determination of triptolide. Peak: 1=acetophenone; 2=triptolide. Conditions as in FIG. 30.

Figure 33:
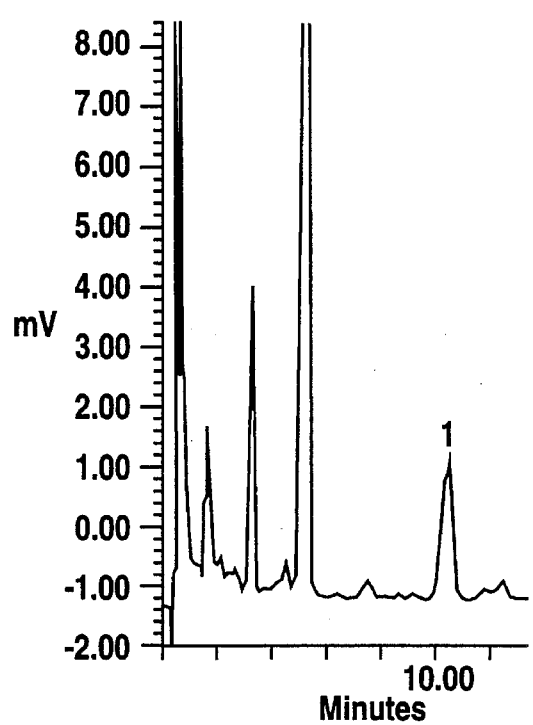

FIG. 33. Chromatogram of the extract of *Tripterygium wilfordii* Hook F. for the determination of tripdiolide. Peak 1=tripdiolide. Conditions as in FIG. 31.

Figure 34:
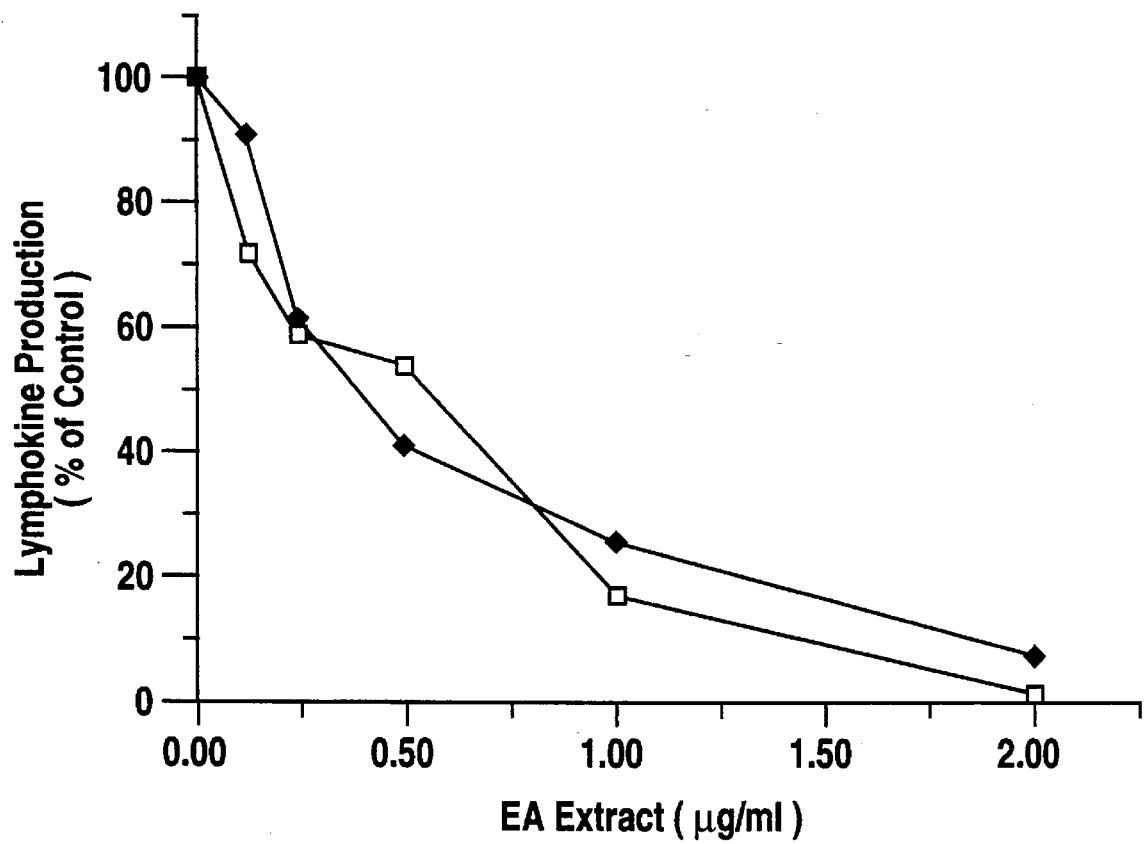

FIG. 34 shows the effect of the EA extract on the production of IL-2 and IFN-γ. T cells ($1 \times 10^5$/ml) were incubated with PHA (1 μg/ml) for 24 hr in the presence or absence of the indicated concentrations of the EA extract. -□-, IFN-γ, -♦-, IL-2.

DESCRIPTION OF PREFERRED EMBODIMENTS

The present invention concerns the use of *Tripterygium wilfordii* Hook F extracts, and components thereof, to inhibit inflammatory processes and immune disorders concurrently with the induction of glucocorticoid-receptor-mediated inhibition of expression of pro-inflammatory genes. The inhibition of the activation of these pro-inflammatory and immune enhancing genes provides a treatment for inflammation or an immune disorder. The further demonstration that these components of TwHF lack steroidal agonist effects indicates that this method may therefore be used to treat autoimmune disease, such as rheumatoid arthritis, to suppress immune function and to suppress inflammation without the undesirable effects of steroids or NSAIDs that are in current use.

Methods for binding to the glucocorticoid receptor are also provided, demonstrating that coupling of glucocorticoid to the glucocorticoid receptor is inhibited in the present of the TwHF preparation. An attractive alternative to use of steroid containing therapeutics in treatment of inflammation and other disorders is thus provided, use of TwHF avoiding the various steroid-related side effects associated with these agents, as well as avoiding the gastric irritation associated with NSAIDs. Therapeutic agents for the treatment and prevention of inflammation that are NSAID and steroid-free are also provided, these preparations containing as an active ingredient a pharmaceutically effective amount of a TwHF extract. Because the TwHF extract provides anti-inflammatory activity, amounts of other agents such as an NSAID or asteroid can be reduced to amounts better tolerated by the patient while providing an alternative medicinal function, i.e., such as the fever reducing or pain relieving function of NSAIDs.

The extract of TwHF inhibits the induction of cyclooxygenase-2 (COX-2) but has no direct effect on cyclooxygenase-1 (COX-1) and probably has no direct effect on the enzymatic activity of either. Therefore, the present invention provides for the blocking of inflammation by blocking the induction of COX-2, leaving COX-1 intact and thereby causing none of the side-effects of NSAIDS that are related to COX-1 inhibition.

T2 was prepared by chloroform-methanol and chloroform-ethanol extraction of *Tripterygium wilfordii* Hook F roots, the skin of the roots having been removed prior to processing the root. As an additional example, the preparation is prepared by ethyl acetate extraction (Example 5).

Example 1 concerns studies on the effect of the *Tripterygium wilfordii* Hook F preparation on human lymphocyte function. Interleukin-2 production by T cells is inhibited by the TwHF extract by inhibiting gene transcription, while the expression of IL-2 receptors is not affected. The *Tripterygium wilfordii* Hook F preparation is also shown to suppress proliferation of B cells and immunoglobulin production by B cells. The studies described in Example 2 indicate that signaling pathways are not affected by the *Tripterygium wilfordii* Hook F preparation, demonstrating the selective nature of the agent's inhibitory activity. Example 3 concerns studies on the effect of the *T. wilfordii* preparation in the treatment of patients with rheumatoid arthritis. Example 4 describes the components of the $T_2$ *T. wilfordii* Hook F preparation and toxicity thereof. Example 5 describes the *T. wilfordii* Hook F preparation obtained by ethyl acetate extraction, while Example 6 demonstrates the in cellulo (intact cell effects) activity of the ethyl acetate extract.

Example 7 provides in vivo studies with the *T. wilfordii* ethyl acetate extract. Example 8 provides a comparative toxicity study of various *T. wilfordii* preparations. Example 9 describes a technique that may be used for determining the dose schedule of the ethyl acetate extract for use in vivo. Example 10 describes the characterization and identification of a fraction '924' (wilforonide) from the ethyl acetate extract and Example 11 describes immunosuppressive effects of wilforonide. Example 12 provides studies that show inhibition of IL-2 gene transcription and inhibition of production of interferon γ by the T2 extract. Example 13 demonstrates inhibition of glucocorticoid-receptor-mediated activation of gene transcription concurrently with a lack of intrinsic GR agonist activity. The significance of these results is that inflammation may be addressed in a subject using T2 without steroids, thus avoiding the undesired agonist effects associated with steroids. Example 14 provides studies of the anti-inflammatory properties of the TwHF extract. A new method for separating and quantitating triptolide and tripdiolide is provided in Example 15 and Example 16 describes the effect of TwHF extract on progesterone metabolism, highlighting the utility of the present invention for reducing progesterone, and the various physiological conditions that are related to progesterone (i.e., pregnancy). Example 17 provides therapeutic preparations of the TwHF extract.

EXAMPLE 1

Effect of $T_2$ on Human Lymphocyte Function

This example describes the effect of the *T. wilfordii* preparation, $T_2$, on in vitro immune responsiveness of human peripheral blood mononuclear cells (PBMC) obtained from normal individuals. It was found that the preparation exerted a concentration-dependent profile of suppressive activity on both T cell and B cell functions, whereas the functional activities of monocytes were more resistant to the suppressive effects of this *T. wilfordii* preparation with chloroform/methanol.

Methods

Cell preparation. PBMC were obtained from the blood of healthy adults by centrifugation on sodium diatrizoate/Ficoll gradients (Sigma, St. Louis, Mo.). Monocytes were isolated from PBMC by centrifugation on Sepra-cell-MN (Sepratech, Oklahoma City, Okla.) or by glass adherence. The monocytes obtained from the two procedures were used to examine interleukin-1 (IL-1) production and antigen presentation, respectively. For purification of T cells and B cells, PBMC were incubated with L-leucine methyl ester HCl (Sigma) for 45 minutes at room temperature to deplete monocytes and natural killer cells[51]. The resultant lymphocytes were rosetted with neuraminidase-treated sheep red blood cells (SRBC) and were then separated by Ficoll/diatrizoate centrifugation[52]. T cells were further purified by passage of the rosette-positive population over a nylon-wool column to remove residual B cells and monocytes[53]. B cells were prepared from the initial population of rosette-negative cells by removing any remaining cells that formed rosettes with neuraminidase-treated SRBC.

Staining with monoclonal antibodies (MAb) to CD3 and CD20 and analysis with the fluorescence-activated cell sorter (FACS) indicated that the T cell and B cell populations were more than 96% and 90% pure, respectively. T cells were incubated with mitomycin c (0.1 mg/ml) for 45 minutes and then washed thoroughly[54].

Reagents, The *T. wilfordii* preparation, $T_2$, used in these studies was a chloroform/methanol extract prepared from the woody portion of the roots of TWH obtained from Taizhou Pharmaceutical Company (Taizhou, Jiang Su, People's Republic of China). This preparation, $T_2$, contained more than 8 different compounds including glycosides, diterpenoids, alkaloids, and ketones. Before use, the extract was dissolved in DMSO and further diluted with culture medium. Phytohemagglutinin (PHA; Wellcome Reagents, Research Triangle Park, N.C.), phorbol dibutyrate (PDB; Sigma), ionomycin (Calbiochem, San Diego, Calif.), and the anti-CD3 MAb, 64.1, were used for T cell activation[55]. MAb 64.1 was purified as previously described [Hansen et al., "T cell protocol", *Leukocyte Typing*. Edited by Bernard, et al. Berlin, Springer-Verlag, 1982]. Human recombinant interleukin-2 (rIL-2; Cetus, Emeryville, Calif.) and/or formalinized Staphylococcus aureus (SA; Calbiochem) was used for B cell activation. The MAb against the α chain of the IL-2 receptor (IL-2R), anti-Tac, was obtained from Dr. Thomas Waldmann (NIH, Bethesda, Md.) and was used to analyze IL-2R expression. Interleukin-1 (Cistron Technology, Pine Brook, N.J.) was purchased for standardization of the IL-1 assay. Affinity-purified goat anti-human IgA, IgG, and IgM and similar antibodies conjugated to horseradish peroxidase were purchased from Tago (Burlingame, Calif.). Streptokinase (SK) and tetanus toxoid (TT) were purchased from Hoechst-Roussel (Somerville, N.J.) and MCDC Biologics (Jamaica Plain, Md.), respectively.

Cell culture and assay of lymphocyte DNA synthesis. T cells ($1 \times 10^5$/well) or B cells ($5 \times 10^4$/well) alone or B cells with mitomycin c-treated T cells ($1 \times 10^5$/well) were cultured in RPMI 1640 medium (Hazleton Biologics, Lenexa, Kans.) supplemented with 10% fetal calf serum, penicillin G (200 units/ml), gentamicin (10 μg/ml), and L-glutamine (0.3 mg/ml) in 96-well microtiter plates in a total volume of 200 μl, with or without the stimuli indicated, and in the presence or absence of various concentrations of $T_2$. The final concentration of DMSO in culture was 0.02–0.002%. This concentration of DMSO had no effect on any of the responses analyzed.

For both T and B cell activation, immobilized anti-CD3 (MAb 64.1) stimulation was used. This MAb was immobilized by incubating 50 μl (5 μg/ml) in each well for at least 2 hours at room temperature. The excess soluble antibody was removed before cell culture (Hansen, supra). Cells were cultured for the indicated duration, and then pulsed with 1 μCi of $^3$H-thymidine, ($^3$H-TdR; New England Nuclear, Boston, Mass.) for the last 12 and 18 hours for T cell and B cell cultures, respectively. 3H-TdR uptake was measured in a liquid scintillation counter. All data are expressed as the mean counts per minute of 3 replicate determinations[56].

IL-1 production assay. Monocytes ($1 \times 10^5$/well) were suspended in RPMI 1640 medium with 1% normal human serum (NHS) and cultured with or without lipopolysaccharide (10 μg/ml) in the presence or absence of various concentrations of $T_2$ for 24 hours. The culture supernatants were collected, and serial dilutions were assayed for IL-1 using C3H/HeJ murine thymocytes as described elsewhere[57]. Concentrations of $T_2$ contained in the dilutions of supernatants had no effect on DNA synthesis by C3H/HeJ thymocytes.

IL-2 production assay. T cells ($1 \times 10^5$/well) were incubated with or without PHA (1 μg/ml) or immobilized anti-CD3 in the presence or absence of various concentrations of $T_2$ for 24 hours. Cell-free supernatants were harvested, serial dilutions were made, and IL-2 content was assayed with CTLL-2 cells as described previously[58].

IL-2R expression. T cells were cultured with or without the indicated stimuli in the presence or absence of various concentrations of $T_2$ for 36 hours. After washing, the cells were stained with saturating concentrations of anti-Tac or a mouse IgG control MAb, followed by fluorescein isothiocyanate-conjugated goat anti-mouse Ig antibody (Cappel, West Chester, Pa.). The samples were fixed with 1% paraformaldehyde and analyzed with a FACSTAR (Becton Dickinson, Mountain View, Calif.) flow cytometer, using a single-histogram statistics program (Davis, supra).

Measurement of Ig synthesis. The amount of IgG, IgA, and IgM in the culture supernatants of B cells stimulated with SA plus rIL-2 in the presence or absence of $T_2$ for 7 days was determined using an isotype-specific enzyme-linked immunosorbent assay method. Quantitation of the Ig in the supernatants was then determined by comparison with a standard curve. The sensitivity of the assay is 15 ng/ml for IgA and IgG, and 30 ng/ml for IgM[59].

Results

Figure 1:
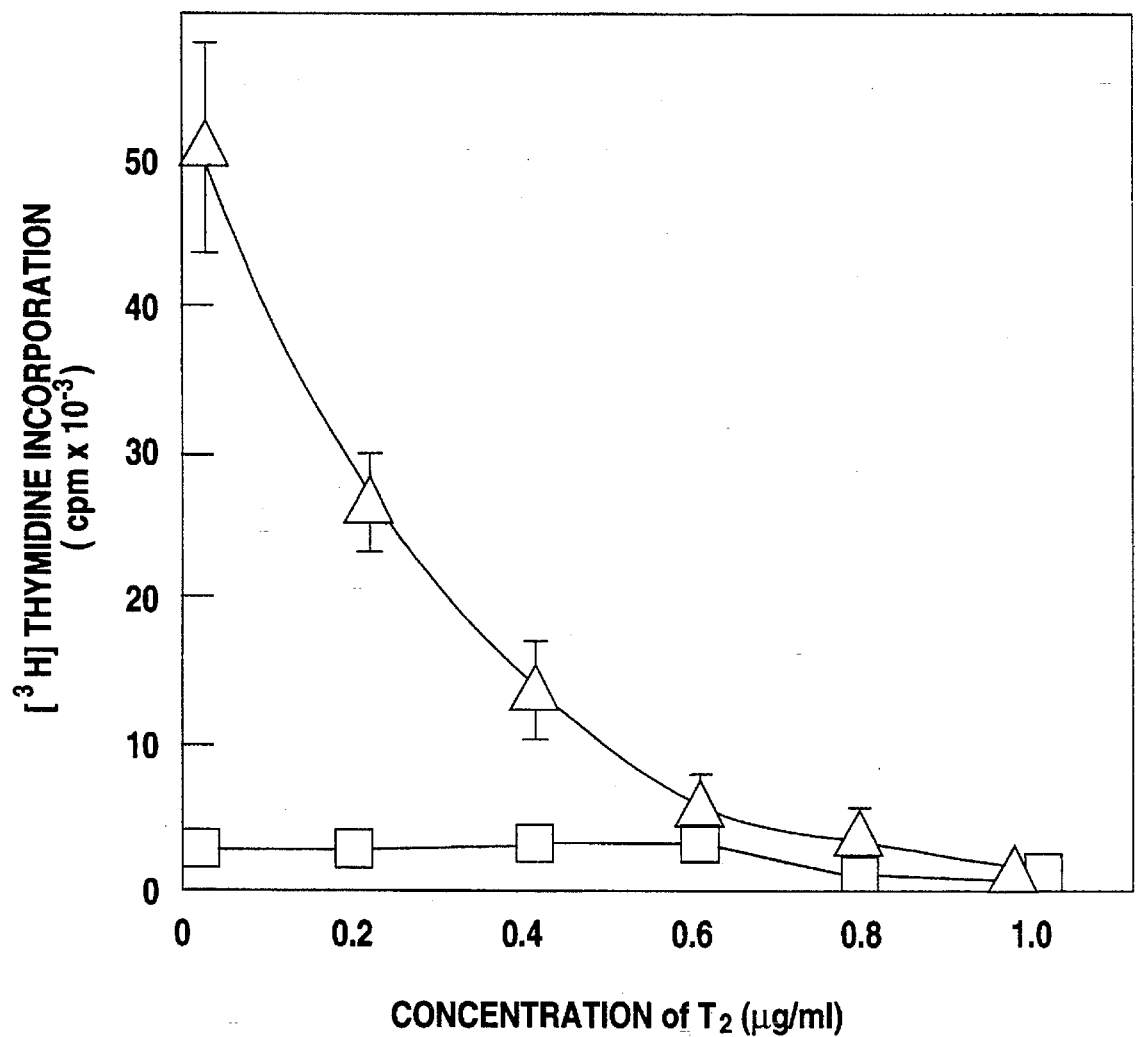
FIG. 1. Effect of $T_2$ on T cell proliferation. T cells ($1 \times 10^5$/well) were cultured with medium (□) or PHA (Δ) in the presence or absence of varying concentrations of $T_2$ as indicated for 3 days. Results represent the mean cpm±SEM of three experiments.
Figure 2A:
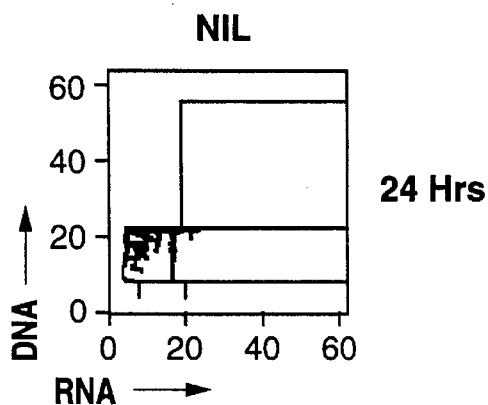
FIG. 2A, FIG. 2B, FIG. 2C, FIG. 2D, FIG. 2E, FIG. 2F, FIG. 2G, FIG. 2H, FIG. 2I, FIG. 2J, FIG. 2K and FIG. 2L. Effect of $T_2$ on cell cycle progression of human T cells. T cells ($1 \times 10^5$/well) were cultured with or without PHA (1 µg/ml) in the absence or presence of the indicated concentrations of $T_2$ for 24, 48 or 72 hrs. The samples were harvested, stained with acridine orange, and analyzed with an ORTHO flow cytometer using the CICERO program to determine the position of cells in the cell cycle as assessed by their RNA and DNA content.
Figure 2D:
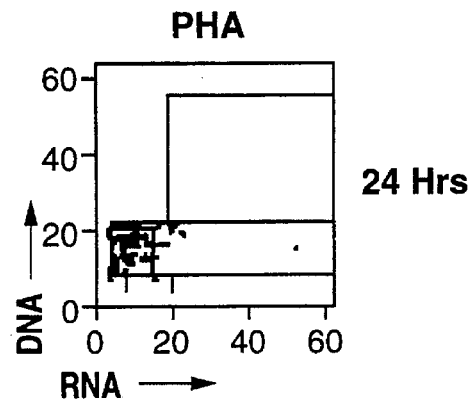
Figure 2B:
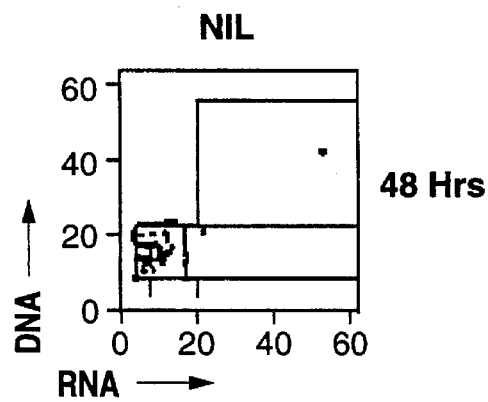
Figure 2E:
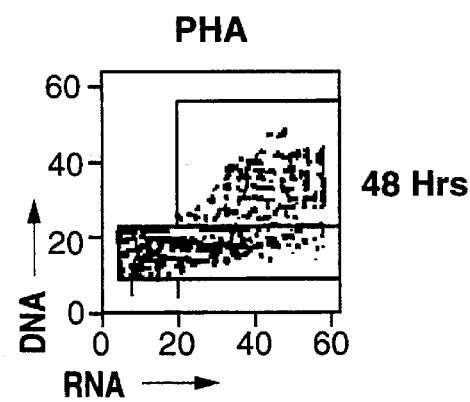
Figure 2C:
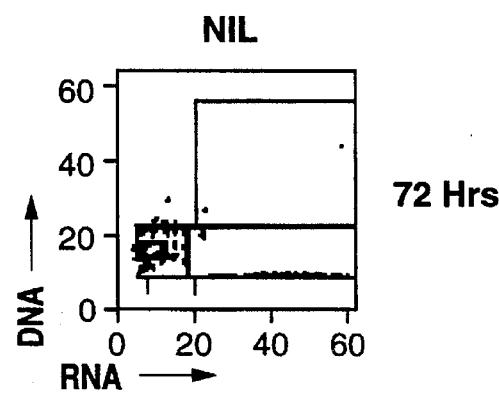
Figure 2F:
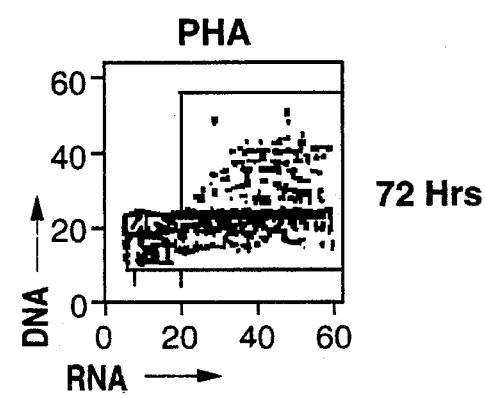
Figure 2G:
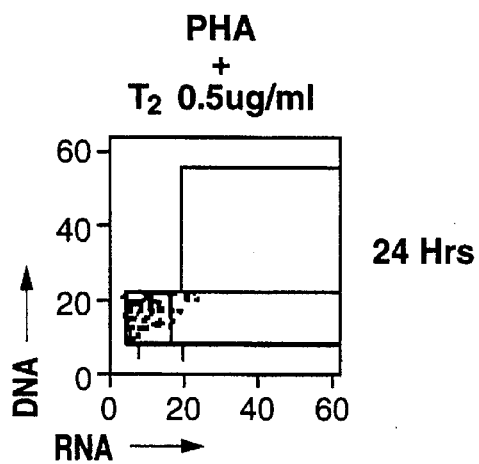
Figure 2J:
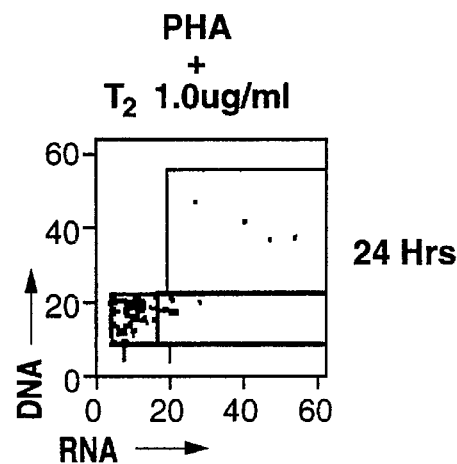
Figure 2H:
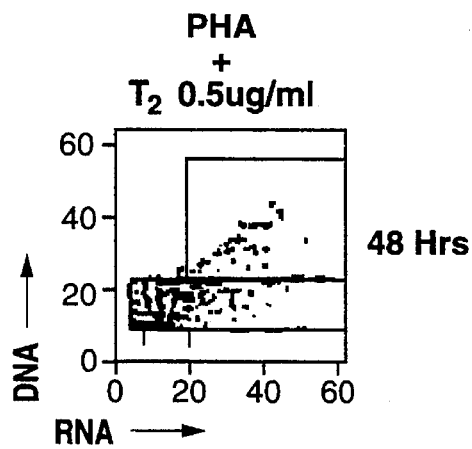
Figure 2K:
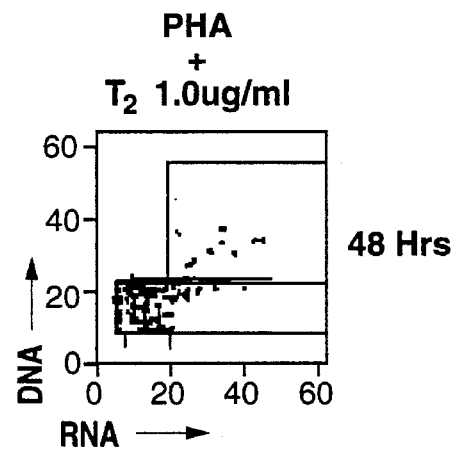
Figure 2I:
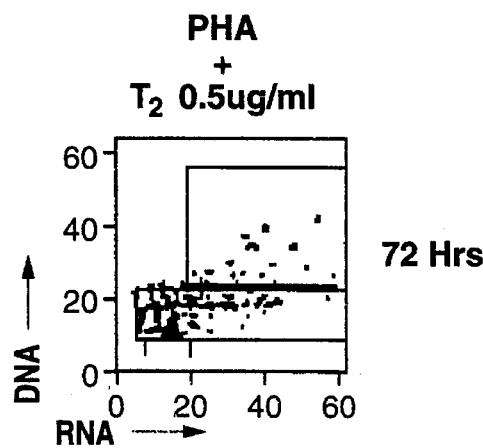
Figure 2L:
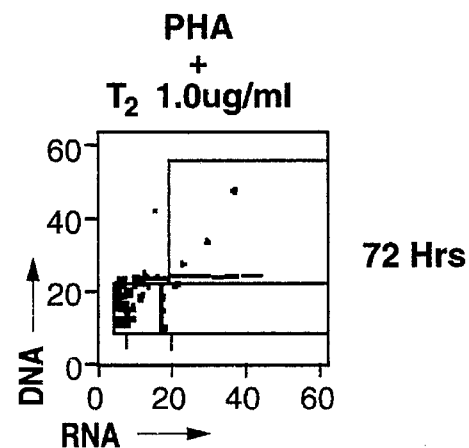
Figure 3:
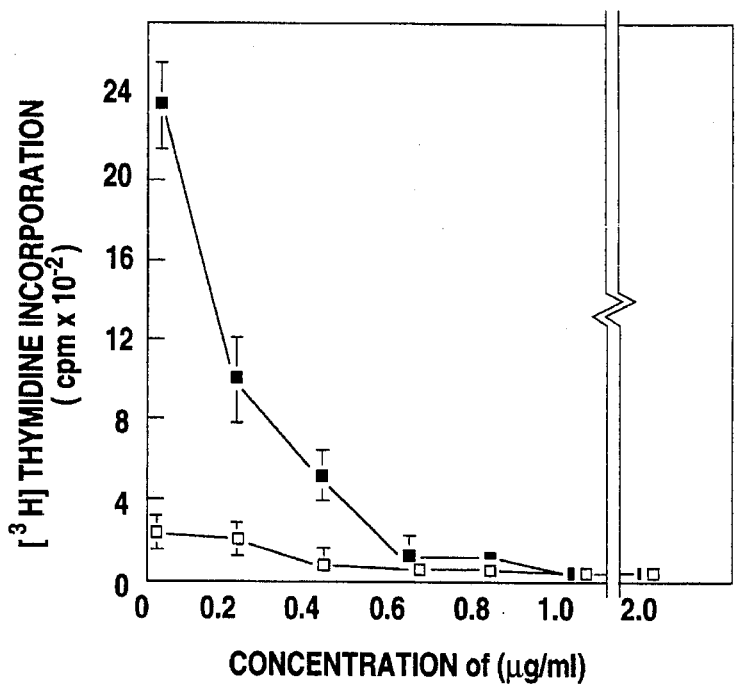
FIG. 3. Inhibitory effect of T2 on IL-2 production. T cells ($1 \times 10^5$/well) were cultured with medium (□) or PHA (■) in the presence or absence of varying concentrations of T2 for 36 hrs. The cell-free supernatants were diluted 1:4 and analyzed for IL-2 activity with CTLL-2 cells. Mean [$^3$H]-TdR incorporation ±SEM of CTLL-2 cells from 6 experiments is shown.

Effect of $T_2$ on human T cell responsiveness. These studies demonstrate that $T_2$ caused concentration dependent inhibition of PEA induced $^3$H-thymidine incorporation by purified human T lymphocytes (FIG. 1). Fifty percent inhibition was noted at concentrations of approximately 0.2 μg per ml. Cell cycle analysis indicated that $T_2$ prevented cells from progressing through the G1 phase of the cell cycle (FIG. 2A–2L). Mitogen induced IL-2 production by purified T-cells was also inhibited by a similar concentration of $T_2$ (FIG. 3). Mitogen induced expression of IL-2 receptors was not inhibited by $T_2$ (Table 1) indicating that it was nontoxic to this cellular activity. These results suggested that the decrease in proliferation might be the result of inhibition of IL-2 production.

TABLE 1

EFFECT OF $T_2$ ON INTERLEUKIN-2 (IL-2) RECEPTOR EXPRESSION*

| $T_2$ | Nil | | PHA | |
|---|---|---|---|---|
| | % positive | Fluorescence intensity | % positive | Fluorescence intensity |
| 0 μg/ml | 10 ± 2 | 483 ± 18 | 65 ± 17 | 561 ± 166 |
| 0.65 μg/ml | — | — | 60 ± 22 | 519 ± 109 |
| 1.25 μg/ml | 9 ± 2 | 504 ± 29 | 61 ± 20 | 525 ± 128 |
| 2.50 μg/ml | — | — | — | — |

*T cells ($1 \times 10^5$/well) were cultured with medium or phytohemagglutinin (PHA) in the presence or absence of various concentrations of $T_2$ as indicated for 36 hours. Cells were collected, stained with anti-Tac monoclonal antibody followed by fluorescein isothiocyanate-conjugated goat anti-mouse IgG, and analyzed by flow cytometry. Values are the mean ± SEM of 6 experiments.

Figure 4:
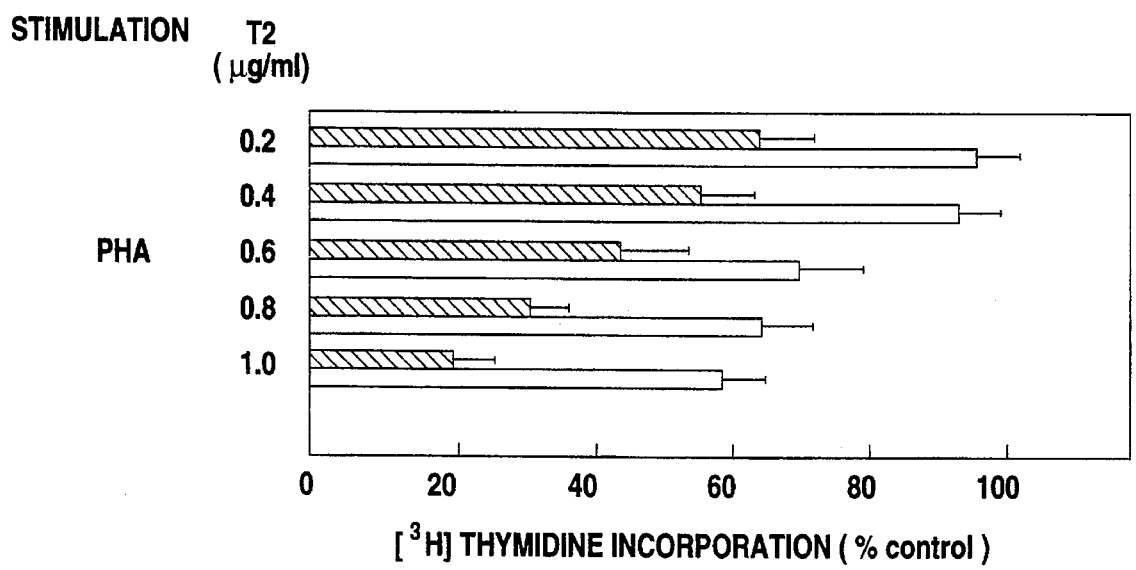
FIG. 4. Effect of supplemental IL-2 on T2 mediated inhibition of T cell proliferation. T cells ($1 \times 10^5$/well) were stimulated with PHA with (□) or without (■) IL-2(10 U/ml) and in the presence or absence of varying concentrations of T2 for 3 days. The data are expressed as percent of control [$^3$H]-TdR incorporation from three experiments.

In order to examine IL-2 production, experiments were carried out in which the effect of $T_2$ on proliferation was examined in the presence of supplemental IL-2. As can be seen in FIG. 4, much of the inhibitory effect of $T_2$ was overcome by supplemental IL-2. The effect of T2 on steady state levels of IL-2 mRNA in mitogen stimulated T cells was studied. T cells ($1\times10^6$/ml) were cultured with and without PHA in the presence or absence of T2 (1 µg/ml). After a 4-hour incubation, total RNA was isolated and IL-2 and actin mRNA levels determined by S1 nuclease protection. The results suggested that one of the major actions of $T_2$ was to inhibit IL-2 production. This appeared to result from an inhibition of IL-2 gene transcription since $T_2$ inhibited the appearance of mRNA for IL-2. These experiments confirmed that one action of $T_2$ was to inhibit IL-2 production.

A method of testing for selective inhibition of IL-2 specific mRNA production is described herein, the method consists of culturing eukaryotic cells in culture with and separately without *Tripterygium wilfordii* Hook F $T_2$ extract or components thereof in a therapeutically effective amount to provide a test sample and a control sample; measuring IL-2 mRNA level and a reference mRNA level such as actin mRNA to provide a test IL-2 mRNA sample, a test reference mRNA sample, a control IL-2 mRNA sample and a control reference mRNA sample; comparing (test IL-2 mRNA level÷control IL-2 mRNA level) to (test reference mRNA level÷control reference mRNA level); and when (test IL-2 mRNA level÷control IL-2 MRNA level) is substantially less than 1 and (test reference mRNA level +control reference mRNA level) is about 1, selective inhibition of IL-2 mRNA production by $T_2$ is indicated.

Effect of $T_2$ on human B lymphocyte responses.

Figure 5A:
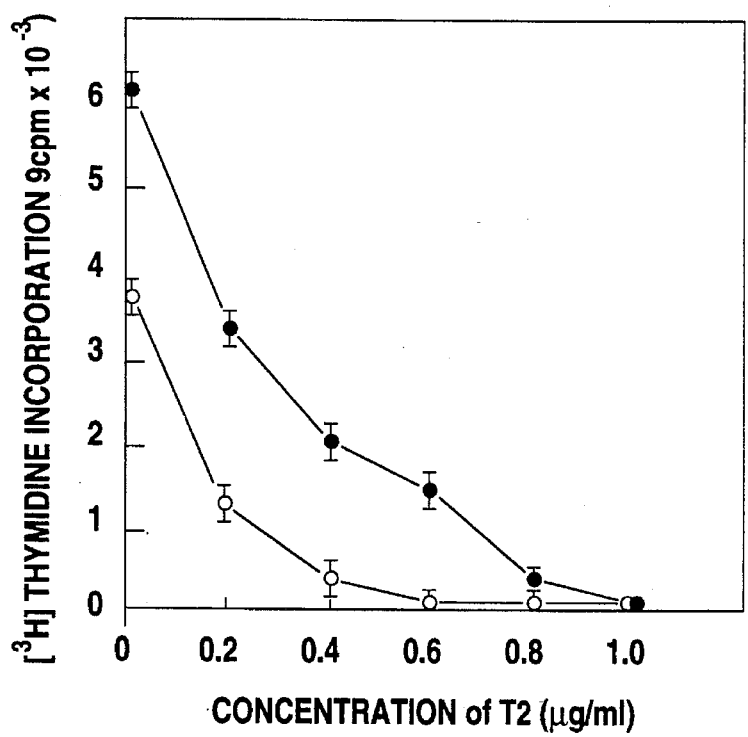
FIG. 5A, and FIG. 5D. Effect of T2 on B cell DNA synthesis and Ig production. In the left panel, B cells ($5 \times 10^4$/well) were stimulated with SA (o) or SA+IL-2 (o), and in the right panel with SA+IL-2 in the presence of varying concentrations of T2. [$^3$H]-TdR was determined after a 5-day incubation (left panel). Supernatants were harvested after a seven-day culture and assayed for IgM (■), IgG (o) and IgA (o) content (right panel). Results are the mean ± SEM of 3 experiments.
Figure 5B:
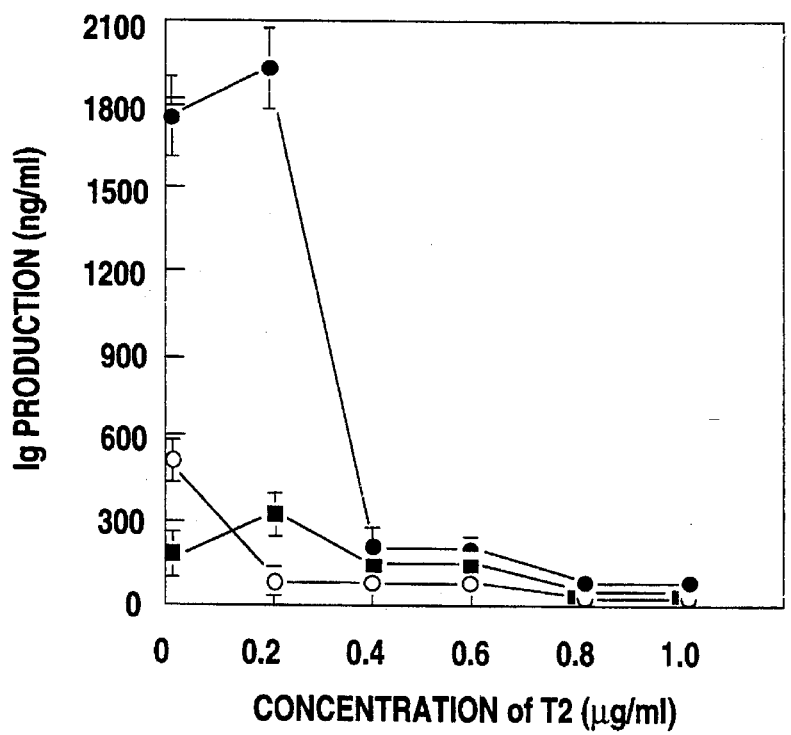

Additional effects of $T_2$ were demonstrated when its action on human B cell responses was examined. As can be seen in FIG. 5A and 5B, $T_2$ inhibited both mitogen-induced proliferation of highly purified B cells, as well as immunoglobulin production in a concentration dependent manner. These results suggested that $T_2$ had additional effects beyond altering IL-2 production. Some specificity for the action of $T_2$ was demonstrated, however, when its effects on a number of other cell types were examined. Thus, $T_2$ had no effect on IL-1 production by human monocytes nor on their capacity to function as antigen presenting cells. In addition, there was no effect on the growth of endothelial cells or fibroblasts during a 48 hour culture. None of the inhibitory effects of $T_2$ could be accounted for by non-specific toxicity, as inhibitory concentrations of $T_2$ had no effect on the viability of either resting or stimulated lymphocytes, endothelial cells, fibroblasts, monocytes, or polymorphonuclear leukocytes. These results support the contention that $T_2$ has a limited spectrum of immunosuppressive activity which cannot be accounted for by nonspecific toxic effects. Of importance, the capacity of $T_2$ to suppress both IL-2 production by T cells, and proliferation and immunoglobulin production by B cells may explain the action of this agent in patients with RA.

EXAMPLE 2

Effect of $T_2$ on Critical Signaling Pathways

The mechanism by which $T_2$ inhibits IL-2 production is examined in greater detail in the present example. *T. wilfordii* may inhibit a critical signaling pathway involved in inducing transcription of the IL-2 gene. Current information suggests that T cell receptor occupancy leads to activation of tyrosine kinases, followed by stimulation of phospholipase C. This results in production of phosphatidyl inositol triphosphate and diacylglycerol, that induce increases in intracellular calcium and activation of protein kinase C, respectively[60]. Therefore, additional studies were carried out to examine the possibility that $T_2$ might inhibit one of these signaling pathways.

Methods

Effect of $T_2$ preparation on total IP generation by activated T cells. Fresh T cells (A) or Jurkat cells (B) were labeled with [$^3$H]-myo-inositol overnight in the absence or presence of the indicated concentrations of the *T. wilfordii* preparation obtained by chloroform/methanol extraction was obtained from the supplier source described in Example 1. The cells were washed and incubated with 10 mM LiCl for 5 minutes then activated with PHA for 60 min. The cells were extracted with 0.75 ml of a 1:1 mixture of chloroform and methanol, followed by 0.25 ml of chloroform and 0.25 ml of water. The phases were separated by centrifugation and the water soluble fractions were applied to a 0.25 ml Agl-X8 formate ion exchange column. Total inositol phosphate was eluted with 1.5 ml of 0.1M formic acid and 1M sodium formate. The radioactivity was quantified by scintillation counting. An aliquot of each cell population was also stimulated with PHA for 24 hours and supernatants assayed for IL-2 content using CTLL-2 cells.

Effect of $T_2$ on the generation of IP fractions by PHA activated T cells. Jurkat cells were labeled with [$^3$H]-myo-inositol overnight in the presence or absence of various concentrations of $T_2$. Following a 5 minute incubation with 10 mM LiCl, the cells were activated with PHA for 60 min. Water soluble IPs were isolated and quantitated. To accomplish this, the cultures were extracted with 0.75 ml of a 1:1 mixture of chloroform/methanol, followed by 0.25 ml each of chloroform and water. The phases were separated by centrifugation and the water soluble fraction was applied to a 0.25 ml Agl-X8 formate ion-exchange column, and washed extensively with 5 mM cold myo-inositol. IP1, IP2 and IP3 were sequentially eluted with 4 ml of 0.2M ammonium formate plus 0.1M formic acid, 10 ml of 0.4M ammonium formate plus 0.1M formic acid and 10 ml of 1M ammonium formate plus 0.1M formic acid respectively. The radioactivity of the various elution fractions was quantified by scintillation counting.

Effect of $T_2$ on DAG generation and IL-2 secretion by PHA stimulated T cells. T cells for each sample were cultured overnight with PHA in the presence or absence of the indicated concentrations of $T_2$. The cell pellets were lysed with a mixture of chloroform and methanol, and fractions separated with 1M NaCl and chloroform. The organic phase was collected and dried under nitrogen. DAG mass in the organic extract was assayed by solubilizing the lipid residues in a mixture of $^{32}$P-γ-ATP and DAG kinase and phosphatidic acid, incubating at 37° C. for 1 hour during which DAG was quantitatively converted to p-phosphatidic acid. The samples were dried and redissolved in chloroform. The solvent was applied to a silica gel and separated by thin layer chromatography with chloroform/methanol/acetic acid. After visualization with iodine, the spot which contained phosphatidic acid was harvested and radioactivity determined by liquid scintillation counting. An aliquot of cells was also stimulated with mitogen and supernatants harvested after 24 hours and assayed for IL-2 content.

Effect of $T_2$ on translocation of PKC. Jurkat cells ($1\times10^6$/ml) were incubated overnight with or without $T_2$ at the indicated concentrations. The cells were lysed by sonication and then cytoplasmic and membrane fractions separated by centrifugation. PKC activity in both the cytoplasmic and membrane fraction was assayed using a protein kinase C assay system (Amersham) which employed a synthetic peptide as a phosphate acceptor in the presence of phosphatidylserine, calcium and PMA.

Figure 6A:
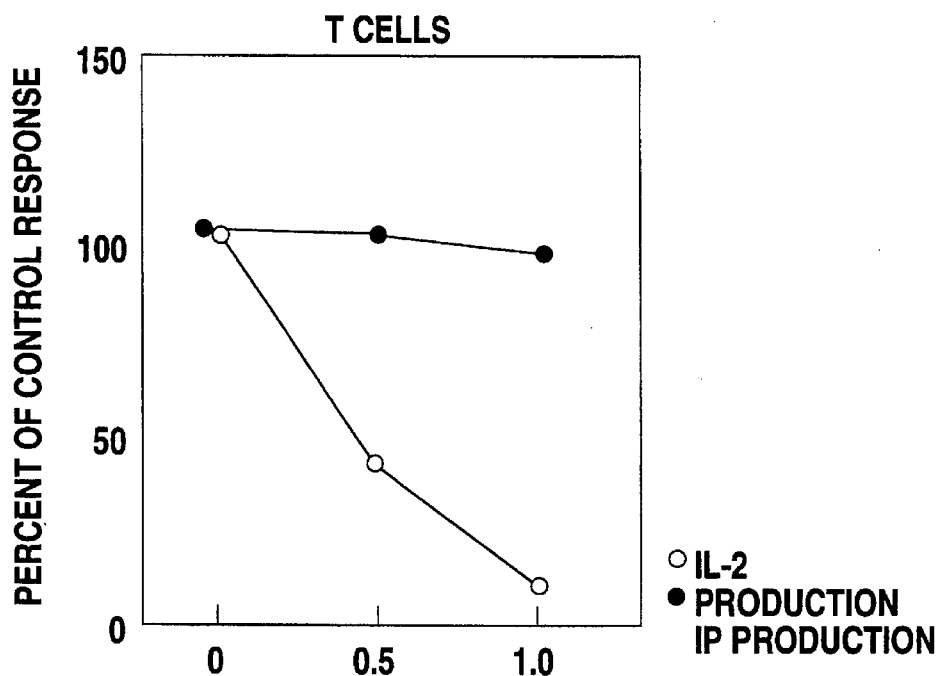
FIG. 6A and FIG. 6B. Effect of T2 on total IP generation by activated T cells. Fresh T cells (A) or Jurkat cells (B) were labeled with [$^3$H]-myo-inositol overnight in the absence or presence of the indicated concentrations of T2. Total IP was determined as described in Example 2. An aliquot of each cell population was also stimulated with PHA for 24 hours and supernatants assayed for IL-2 content using CTLL-2 cells (o). Data are the mean of three replicate experiments.
Figure 6B:
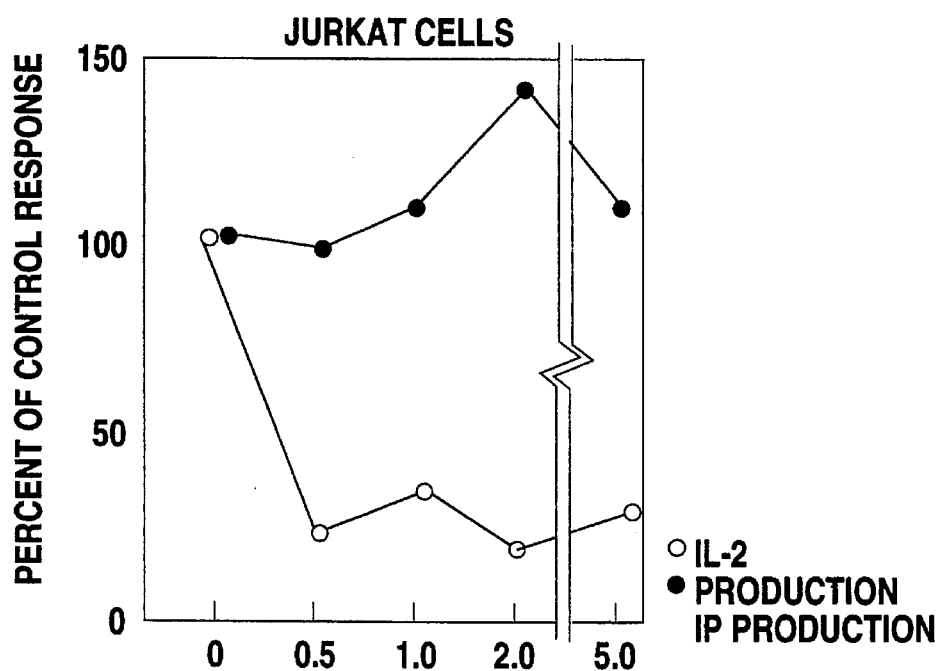
Figure 7A:
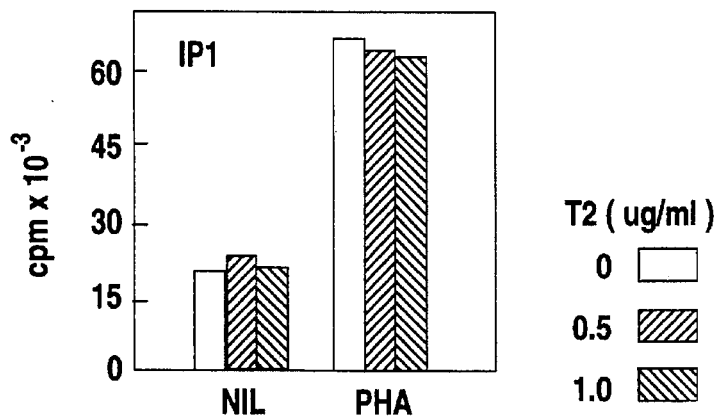
FIG. 7A, FIG. 7B and FIG. 7C. Effect of T2 on the generation of IP fractions by PHA activated T cells. Jurkat cells were labeled with [$^3$H]-myo-inositol overnight in the presence or absence of various concentrations of T2. Following a 5 minute incubation with 10 mM LiCl, the cells were activated with PHA for 60 min. Water soluble IPs were isolated (IP1, top panel; IP2, middle panel and IP3, bottom panel) and quantitated as described in Example 2. Data are from one of three similar experiments.
Figure 7B:
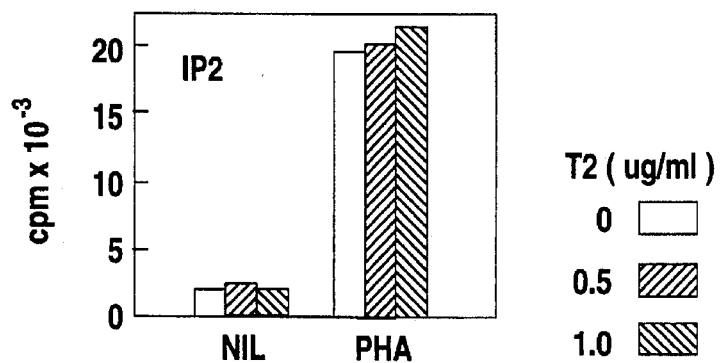
Figure 7C:
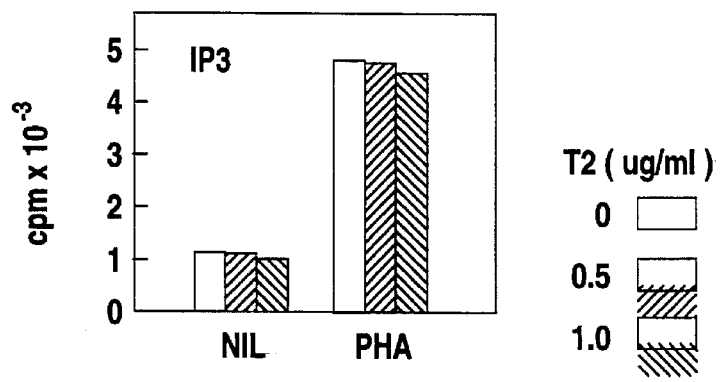
Figure 8:
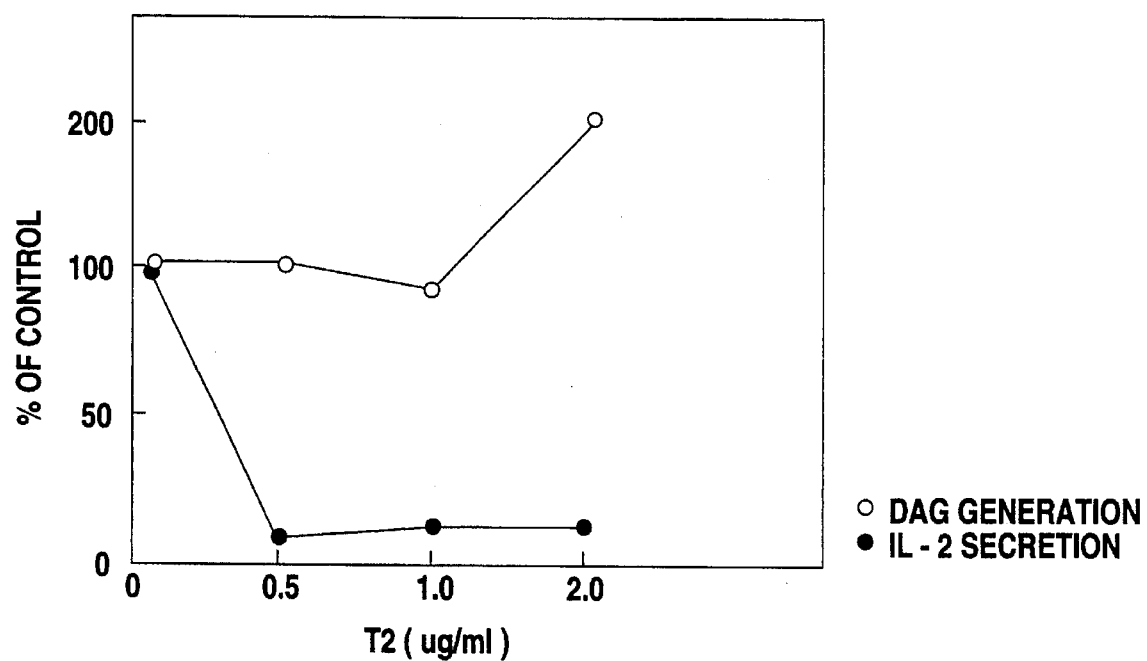
FIG. 8. Effect of T2 on DAG generation and IL-2 secretion by PHA stimulated T cells. DAG and IL-2 were assayed as described in Example 2. Data represent the mean of duplicate determination of three similar experiments.

Effect of $T_2$ on protein tyrosine phosphorylation. Jurkat cells ($3\times10^6$) were incubated overnight in the absence or presence of the indicated concentrations of $T_2$. The cells were washed and stimulated with PHA for 30 minutes. After centrifugation, the pelleted cells were solubilized with 1×SDS sample buffer containing protease inhibitors. The lysates were centrifuged at 10,000 rpm for 15 minutes. The supernatants were analyzed for protein phosphorylation by western blotting using a mouse monoclonal antibody (Upstate Biotechnology, Inc.) against phosphotyrosine.
Results The effect of $T_2$ on mitogen induced production of phosphatidyl inositol metabolites. As can be seen in FIG. 6A–6B, mitogenic stimulation lead to the production of IL-2 and phosphatidyl inositol metabolites. Whereas IL-2 production was inhibited, generation of phosphatidyl inositol metabolites was not. Similar results were seen in fresh T cells and in the Jurkat leukemic T cell line. Additional studies examined whether $T_2$ specifically inhibited generation of IP3, which is thought to induce increases in intracellular calcium[52]. As can be seen in FIG. 7A–7C, $T_2$ had no effect on the generation of IP3 or other specific PI metabolites by mitogen activated T cells. Similar experiments examined the effect of $T_2$ on the generation of diacylglycerol. As can be seen in FIG. 8, $T_2$ inhibited IL-2 production from mitogen stimulated T cells, but had no effect on DAG production. Additional of the inventors studies, not shown, examined the activity of $T_2$ on phospholipase C activity isolated from fresh T cells or Jurkat cells. Again, no inhibitory activity was observed. These experiments suggested that the action of $T_2$ cannot be explained by an effect on these early signaling pathways. At these levels of $T_2$ extract addition, nontoxicity to other cellular functions is established as indicated by these cellular assays.

Figure 9A:
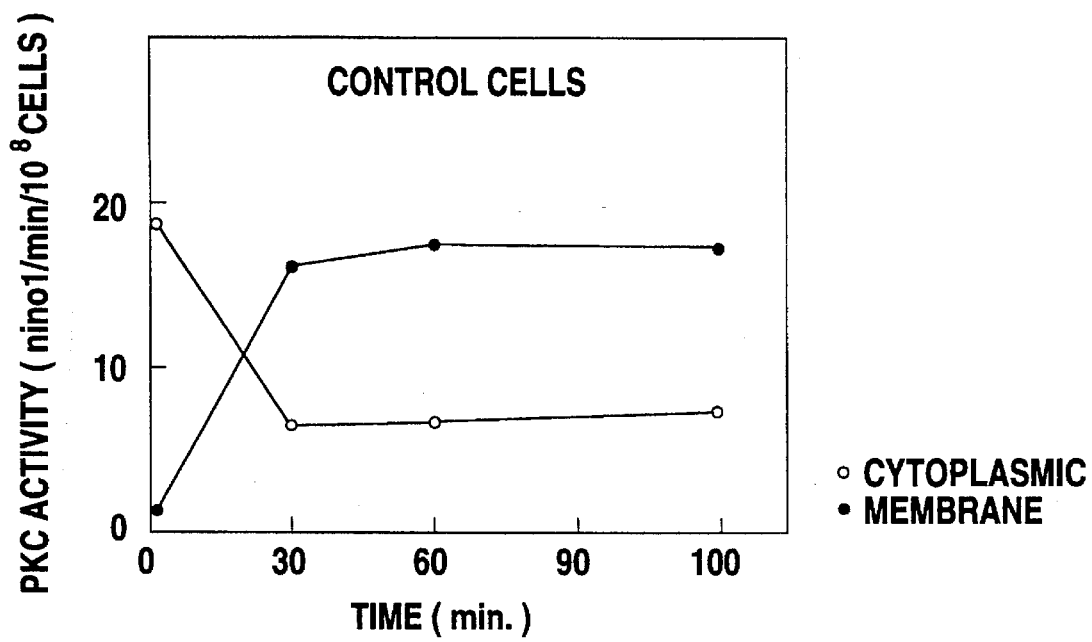
FIG. 9A and FIG. 9B. Effect of T2 on translocation of PKC. PKC activity in both the cytoplasmic and membrane fractions were assayed as described in Example 2.
Figure 9B:
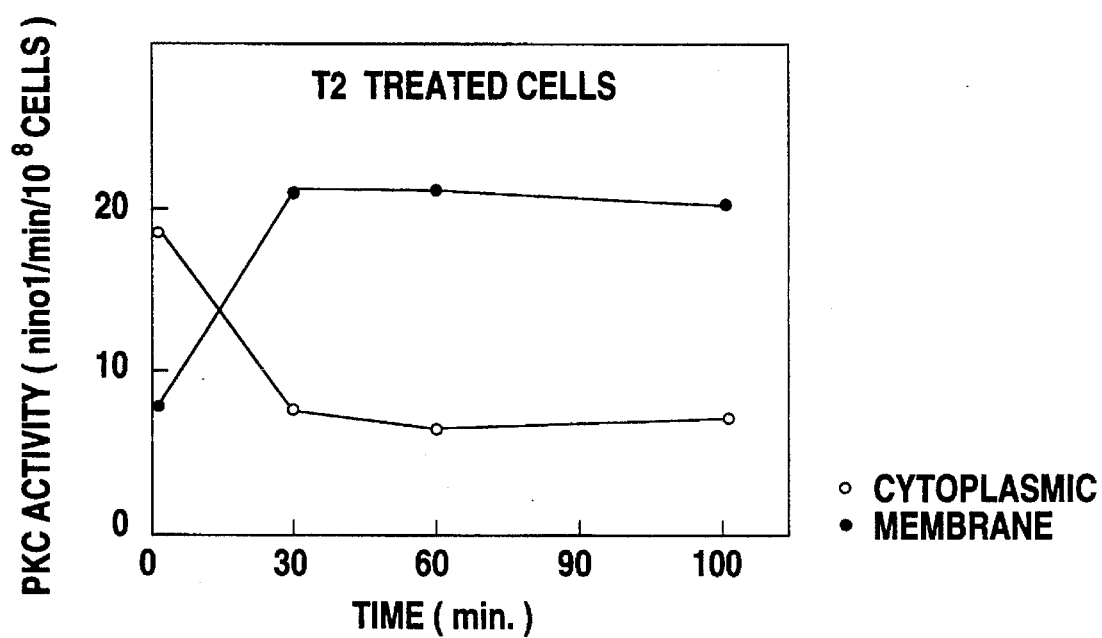

The effect of $T_2$ on protein kinase C activation. As can be seen in FIG. 9A-9B, mitogen stimulation led to translocation of PKC in Jurkat cells, and $T_2$ did not effect PKC translocation. Finally, the effect of $T_2$ on the activity of protein tyrosine kinase activity was explored. Mitogenic stimulation of T cells lead to phosphorylation of a number of protein species identified with a specific antibody to phosphotyrosine. However, $T_2$ did not inhibit the activity of protein tyrosine kinase since the same bands were observed regardless of the presence of $T_2$ during mitogenic stimulation. These experiments convincingly demonstrate that $T_2$ has no effect on early signaling pathways involved in induction of IL-2 gene transcription.

EXAMPLE 3

In Vivo Trials

In an open trial, it was found that a mixture of compounds ($T_2$) extracted from *Tripterygium wilfordii* Hook F was effective in the treatment of rheumatoid arthritis.

To confirm the previous results obtained from these open studies, a prospective, controlled, double-blind cross-over study was designed and carried out.

The treatment plan was designed as follows:

Seventy patients with classic or definite adult-onset rheumatoid arthritis who had active disease for more than 6 months were accepted into the trial and randomly assigned to 2 treatment groups. Patients in Group A received $T_2$ for a first course of treatment of 12 weeks, and then were subsequently changed to placebo for a second course of treatment of 4 weeks duration. Patients of Group B received placebo during the first course and then were crossed-over and received $T_2$ therapy during the second course. $T_2$ was taken in a dosage of 60 mg daily. Placebo tablets were identical in appearance to $T_2$ tablets. Table 2 shows the treatment plan schedule.

TABLE 2

TREATMENT PLAN (TOTAL COURSE: 16 WEEKS)

| | First course treatment (12 weeks) | Second course treatment (4 weeks) |
|---|---|---|
| Group A | $T_2$, 20 mg t.i.d. | Placebo |
| Group B | Placebo | $T_2$, 20 mg t.i.d. |

All patients were assessed in an arthritis clinic every 4 weeks. The clinical assessment, overall assessment by physicians and drug distribution were carried out by individual doctors in a blinded manner. The laboratory assessments were done by technicians of a central hospital laboratory, who were also blinded to the details of the trial.

TABLE 3

CLINICAL FEATURES OF PATIENTS ENTERING THE TRIAL

| | First Treatment Course | | Second Treatment Course | |
|---|---|---|---|---|
| | Group A $T_2$ | Group B Placebo | Group A Placebo | Group B $T_2$ |
| Number of Patients | 35 | 35 | 27 | 31 |
| Male/Female | 3/32 | 4/31 | 1/26 | 4/27 |
| Mean age, years | 46.3 | 48.0 | 46.2 | 47.7 |
| Mean disease duration (years) | 5.9 | 6.1 | 5.8 | 6.0 |
| Stage of Disease | | | | |
| (1) | 6 | 6 | 4 | 5 |
| (2) | 14 | 16 | 11 | 13 |
| (3) | 12 | 10 | 10 | 9 |
| (4) | 3 | 3 | 2 | 4 |

The clinical features of patients entering the trial are shown in Table 3. Statistical analyses demonstrated that at the beginning of the trial, Group A and Group B did not differ from each other significantly in age, sex, duration of disease or stage of disease.

TABLE 4

RESULTS OF A CONTROLLED TRIAL OF $T_2$ IN RHEUMATOID ARTHRITIS

| | | No. of Patients Completing Treatment | |
|---|---|---|---|
| Group | No. Beginning Treatment | First Course (12 wks) | Second Course (4 wks) |
| A ($T_2$ –> Placebo) | 35 | 27 | 24 |
| B (Placebo –> $T_2$) | 35 | 31 | 25 |

As shown in Table 4, 27 patients of Group A completed the first course of treatment, of which 24 completed the second course. 31 and 25 of Group B completed the first course and second course of treatment, respectively.

Table 5 indicates the reasons patients withdrew from the study. Three patients of Group B but none of Group A withdrew from the trial because of worsening of disease during the first course of treatment, whereas 4 patients from Group A but none from Group B withdrew from the trial because of side effects.

TABLE 5

REASONS FOR WITHDRAWAL FROM THE STUDY

|  | First Course Treatment | | | | Second Course Treatment | | | |
|---|---|---|---|---|---|---|---|---|
|  | Group A $T_2$ (n = 35) | | Group B Placebo (n = 35) | | Group A Placebo (n = 27) | | Group B $T_2$ (n = 31) | |
|  | No. | % | No. | % | No. | % | No. | % |
| Lost to follow up | 4 | 11 | 1 | 3 | 3 | 11 | 6 | 19 |
| Worsening of disease | 0 | 0 | 3 | 9 | 0 | 0 | 0 | 0 |
| Side effects | 4 | 11 | 0 | 0 | 0 | 0 | 0 | 0 |

Table 6 shows the therapeutic effects of the first course of treatment. In comparison with patients of Group B, patients of Group A showed significant improvement in all clinical assessments including morning stiffness, joint tenderness score, number of swollen joints, grip strength and 15 meter walking time.

TABLE 6

CHANGES IN CLINICAL PARAMETERS IN PATIENTS COMPLETING THE FIRST COURSE OF TREATMENT

|  |  | Group A $T_2$ (n = 27) | Group B Placebo (n = 31) | *p |
|---|---|---|---|---|
| Morning stiffness (hours) | Before | 2.4 ± 0.4 | 1.1 ± 0.2 | |
|  | After | 0.9 ± 0.2 | 2.3 ± 1.4 | 0.01 |
| Joint tenderness score | Before | 25.1 ± 1.9 | 25.5 ± 1.7 | |
|  | After | 7.9 ± 1.3 | 21.9 ± 2.1 | 0.001 |
| Number of swollen joints | Before | 9.2 ± 0.9 | 7.8 ± 0.7 | |
|  | After | 4.3 ± 0.6 | 7.4 ± 1.1 | 0.01 |
| Grip strength (mean of both sides, mm Hg) | Before | 49.0 ± 0.4 | 73.6 ± 7.7 | |
|  | After | 84.4 ± 7.5 | 81.2 ± 8.9 | 0.05 |
| 15 meter walking time (second) | Before | 36.6 ± 6.6 | 37.0 ± 2.4 | |
|  | After | 21.6 ± 1.5 | 31.9 ± 3.6 | 0.05 |

The most noteworthy improvement was observed in joint tenderness score, which improved from a mean of 25.1 before entry to a mean of 7.9 after the first course of treatment with $T_2$. By contrast, there were no significant changes in this score in Group B patients treated with placebo.

As shown in Table 7, treatment with $T_2$ also caused improvement in laboratory correlates of disease activity. Significant improvements in ESR, CRP and immunoglobulin levels were noted. The changes were significant at the p 0.001 level when compared between Group A and Group B.

TABLE 7

CHANGES IN LABORATORY PARAMETERS IN PATIENTS COMPLETING THE FIRST COURSE OF TREATMENT

|  |  | Group A $T_2$ (n = 27) | Group B Placebo (n = 31) | *p |
|---|---|---|---|---|
| ESR (mm/hour) | Before | 69.2 ± 6.4 | 63.9 ± 5.2 | |
|  | After | 41.0 ± 5.9 | 67.2 ± 6.6 | <0.001 |
| CRP (u/ml) | Before | 29.4 ± 5.7 | 31.6 ± 4.1 | |
|  | After | 10.4 ± 3.9 | 43.7 ± 7.0 | <0.001 |
| RF (titers) | Before | 87.1 ± 23.2 | 86.1 ± 35.5 | |
|  | After | 48.0 ± 13.4 | 63.4 ± 10.9 | NS |
| IgG (u/ml) | Before | 227.5 ± 4.6 | 231.9 ± 14.2 | |

TABLE 7-continued

CHANGES IN LABORATORY PARAMETERS IN PATIENTS COMPLETING THE FIRST COURSE OF TREATMENT

|  |  | Group A $T_2$ (n = 27) | Group B Placebo (n = 31) | *p |
|---|---|---|---|---|
|  | After | 117.4 ± 9.5 | 180.4 ± 29.8 | <0.001 |
| IgM (u/ml) | Before | 302.8 ± 40.3 | 284.5 ± 32.2 | |
|  | After | 105.2 ± 11.1 | 261.3 ± 29.3 | <0.001 |
| IgA (u/ml) | Before | 289.6 ± 29.4 | 257.6 ± 25.2 | |
|  | After | 149.0 ± 15.5 | 280.4 ± 29.8 | <0.001 |

*Group A vs Group B

There was a greater tendency to decrease RF titer in $T_2$ treated patients but the difference between the two groups after the first course of treatment was not statistically significant.

During the second course of therapy, patients who had received placebo initially improved significantly after 4 weeks of therapy with $T_2$. (See Table 8). Significant improvements in joint tenderness score, number of swollen joints and grip strength were noted. Improvement in morning stiffness and 15 meter walking time were also noted, but these changes did not achieve statistical significance. Patients who had received $T_2$ during the first 12 weeks of therapy continued to maintain improvement even after 4 weeks of placebo therapy during the second course.

TABLE 8

CHANGES IN CLINICAL PARAMETERS IN PATIENTS COMPLETING THE SECOND COURSE OF TREATMENT

|  |  | Group A $T_2$ (n = 27) | *p | Group B Placebo (n = 31) | *p |
|---|---|---|---|---|---|
| Morning stiffness (hours) | Before | 1.8 ± 0.2 | | 2.5 ± 1.7 | |
|  | After | 0.8 ± 0.2 | NS | 1.3 ± 0.9 | NS |
| Joint tenderness score | Before | 7.9 ± 1.4 | | 22.2 ± 2.4 | |
|  | After | 11.0 ± 2.6 | NS | 13.5 ± 2.0 | <0.001 |
| Number of swollen joints | Before | 4.2 ± 0.8 | | 7.0 ± 1.2 | |
|  | After | 4.4 ± 0.9 | NS | 3.5 ± 0.5 | <0.05 |
| Grip strength (mean of both sides, mm Hg) | Before | 87.5 ± 8.0 | <0.05 | 80.1 ± 9.2 | |
|  | After | 70.2 ± 9.5 | | 97.1 ± 13.2 | 0.05 |
| 15 meter walking time (second) | Before | 20.3 ± 1.7 | NS | 31.5 ± 5.9 | |
|  | After | 17.1 ± 0.6 | | 18.9 ± 2.3 | NS |

*After vs before treatment

Aside from grip strength, no significant changes were observed in clinical assessments in Group A patients after 4 weeks of placebo treatment.

As shown in Table 9, significant decreases in ESR and RF titer were noted in Group B patients after the second course of treatment. No significant worsening in laboratory parameters were noted in Group A patients after 4 weeks of placebo therapy.

TABLE 9

CHANGES IN LABORATORY PARAMETERS IN PATIENTS COMPLETING THE SECOND COURSE OF TREATMENT

|  |  | Group A $T_2$ (n = 24) |  | Group B Placebo (n = 25) | *p |
|---|---|---|---|---|---|
| ESR | Before | 42.3 ± 6.0 |  | 68.5 ± 6.9 |  |
| (mm/hour) | After | 31.7 ± 7.3 | NS | 22.0 ± 4.9 | <0.001 |
| RF | Before | 49.3 ± 13.5 |  | 67.2 ± 12.1 |  |
| (titers) | After | 32.0 ± 12.3 | NS | 32.0 ± 19.1 | <0.05 |

*After vs before treatment

The overall effectiveness of $T_2$ in the present trial was classified by its capacity to induce remissions, meaningful improvement or no therapeutic effect. (See Table 10).

TABLE 10

OVERALL EVALUATION OF THE PRESENT TRIAL

|  | First Course Treatment | | | | Second Course Treatment | | | |
|---|---|---|---|---|---|---|---|---|
|  | Group A $T_2$ (n = 27) | | Group B Placebo (n = 31) | | Group A Placebo (n = 24) | | Group B $T_2$ (n = 25) | |
|  | No. | % | No. | % | No. | % | No. | % |
| Remission | 2 | 7.4 | 0 | 0 | 0 | 0 | 0 | 0 |
| Improvement |  |  |  |  |  |  |  |  |
| Patient's assessment | 25 | 93 | 7 | 23 | 20 | 82 | 20 | 80 |
| Physician's assessment | 25 | 93 | 7 | 23 | 19 | 79 | 22 | 88 |
| Clinical criteria | 22 | 82 | 7 | 23 | 19 | 79 | 11 | 44 |
| Laboratory evaluation | 23 | 85 | 4 | 13 | 18 | 75 | 13 | 52 |

Based on the therapeutic criteria for remission in RA developed by a subcommittee of the ARA, remission was observed in two patients of Group A at the end of the first course of treatment.

The percentage of patients who experienced meaningful improvements was significantly higher for Group A than for Group B patients as evaluated by physician's assessment, and clinical and laboratory evaluations after the first course of treatment.

The percent of Group B patients experiencing meaningful improvement after the second course of treatment was also remarkable, whereas improvement was maintained in Group A patients during the 4 week second course of placebo.

In order to determine whether $T_2$ exerted an immunosuppressive effect in patients with RA, peripheral blood mononuclear cells (PBMC) were obtained from 18 patients of each group before and after the first course of treatment. These cells were cultured for 14 days and the amounts of IgM-RF and total IgM secreted were determined using a radioimmunoassay. (See Table 11).

TABLE 11

PRODUCTION OF IgM-RF AND TOTAL IgM BY PBMC OF PATIENTS AFTER THE FIRST COURSE OF TREATMENT

|  |  | Group A $T_2$ (n = 18) | Group B Placebo (n = 18) | *p |
|---|---|---|---|---|
| RF | Before | 7.2 ± 3.2 | 5.4 ± 1.6 |  |
|  | After | 1.5 ± 0.5 | 7.0 ± 2.2 | <0.01 |
| IgM | Before | 220.7 ± 53.6 | 260.5 ± 49.3 |  |
|  | After | 151.9 ± 55.3 | 301.2 ± 100.5 | <0.01 |

*Group A vs Group B

In comparison with Group B, significant decreases in both IgM-RF and total IgM were noted in Group A after $T_2$ treatment. These results suggest that $T_2$ therapy had suppressed both IgM and IgM RF production in these patients and thus exerted an immunosuppressive effect.

As shown in Table 12, the most common side effects of $T_2$ were dermal reactions including skin rash, cheilosis, thinning of skin and nails and pigmentation.

TABLE 12

INCIDENCE OF ADVERSE REACTIONS

|  | First Course Treatment | | | | Second Course Treatment | | | |
|---|---|---|---|---|---|---|---|---|
|  | Group A $T_2$ (n = 31) | | Group B Placebo (n = 31) | | Group A Placebo (n = 24) | | Group B $T_2$ (n = 25) | |
|  | No. | % | No. | % | No. | % | No. | % |
| Skin rash & cheilosis | 15 | 39 | 1 | 3 | 0 | 0 | 7 | 28 |
| Diarrhea | 6 | 27 | 0 | 0 | 0 | 0 | 2 | 8 |
| Anorexia | 2 | 5 | 0 | 0 | 1 | 4 | 0 | 0 |
| Abdominal pain | 2 | 5 | 1 | 3 | 0 | 0 | 0 | 0 |
| Amenorrhea | 5/16 | 31 | 0 | 0 | 5/16 | 31 | 1/18 | 6 |
| Postmenopausal vaginal bleeding | 1/10 | 10 | 0 | 0 | 0 | 0 | 0 | 0 |

Although the incidence of skin reactions was quite high in Group A during the first course of treatment, none of the patients had to discontinue $T_2$ treatment. Amenorrhea was another important side effect of $T_2$. It was observed that 31% of female patients aged 49 or less having received $T_2$ for 12 weeks developed amenorrhea whereas 6% of patients developed it after 4 weeks of $T_2$ treatment. Amenorrhea disappeared in most patients when $T_2$ was discontinued.

Figure 10:
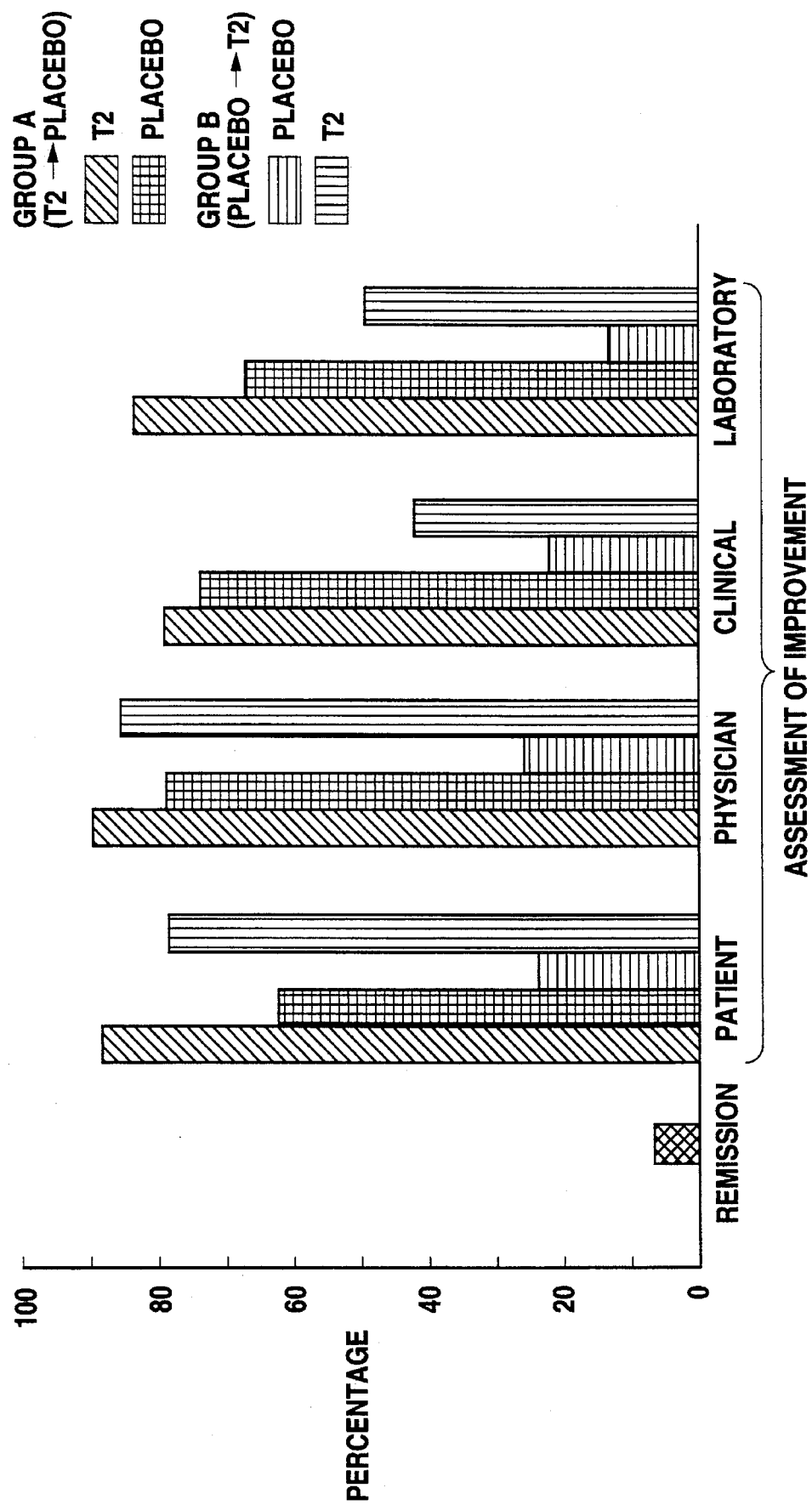
FIG. 10 summarizes assessment of symptomatic improvement in rheumatoid arthritis patients as a result of treatment with a mixture from *Tripterygium wilfordii* Hook F.

FIG. 10 summarizes the assessed improvements in symptoms of rheumatoid arthritis described above. $T_2$ is an effective treatment for rheumatoid arthritis, significantly improving clinical manifestations and laboratory correlates of inflammation. Although toxicity was frequent, it necessitated cessation of therapy in few. Clinical improvement was observed after only 4 weeks of therapy and persisted for at least 4 weeks after the medication was discontinued. Therapy with $T_2$ suppresses the in vitro production of IgM and IgM rheumatoid factor.

Administration of the $T_2$ extract has also been shown to be effective in the treatment of systemic lupus erythematosus (Table 130). It also appears to be effective in relieving acute clinical manifestations including joint inflammation, skin rash and renal disease (Table 13). Asteroid sparing effect of $T_2$ was also noted. In comparison with corticosteroids and commonly used immunosuppressive agents, such as cyclophosphamide, patients treated with $T_2$ had fewer significant complications.

TABLE 13

THERAPEUTIC EFFECT OF $T_2$ IN LUPUS NEPHRITIS

1. Patient group
   10 patients, aged 22–37, with duration of disease > 1 year were treated with $T_2$
2. Laboratory evaluation - before treatment
   +ANA:10
   anti-DNA binding > 20%:9
   Proteinuria > 3 g/24h:10
   Elevated serum creatinine: 3
3. Treatment plan:
   First month: $T_2$ 20 mg tid. Maintain prednisone < 40 mg/day
   Followed by $T_2$ 10 mg tid. and tapered prednisone
   Total course of $T_2$: 24 weeks
4. Results of treatment:
   Serum creatinine returned to normal in 2/3
   Proteinuria improved in 10/10:
   undetectable: 3
   <1 g/24h:3
   >1 g/24h:4
   Concomitant Medication
   3: withdrew from prednisone
   6: continued prednisone <10 mg/day
   1: changed to cyclophosphamide

EXAMPLE 4

Components of $T_2$ Extract and Toxicity Thereof

The present example is provided to demonstrate the isolation and characterization of the various chemical components of a *T. wilfordii* Hook F root extract identified by the present inventors.

Figure 11:
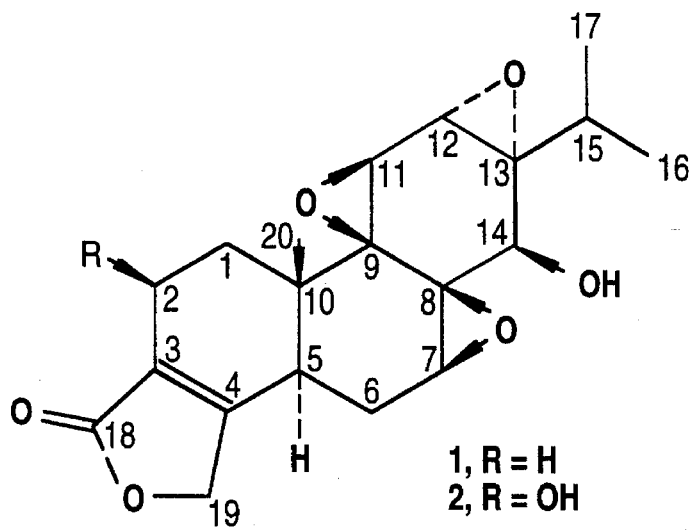
FIG. 11 schematically shows the structure of triptolide (1) and tripdiolide (2).
Figure 12:
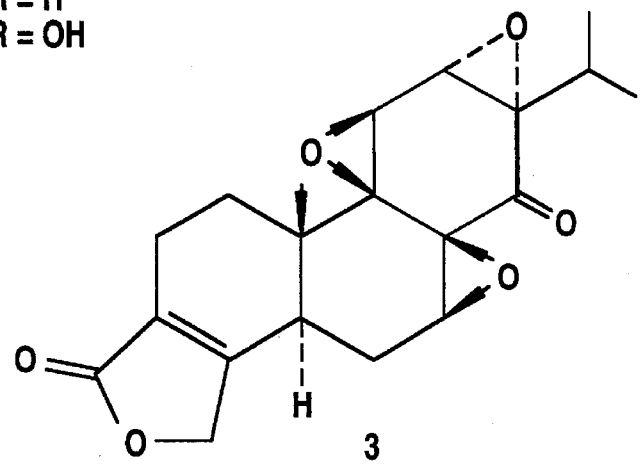
FIG. 12 schematically shows the structure of triptonide.
Figure 17:
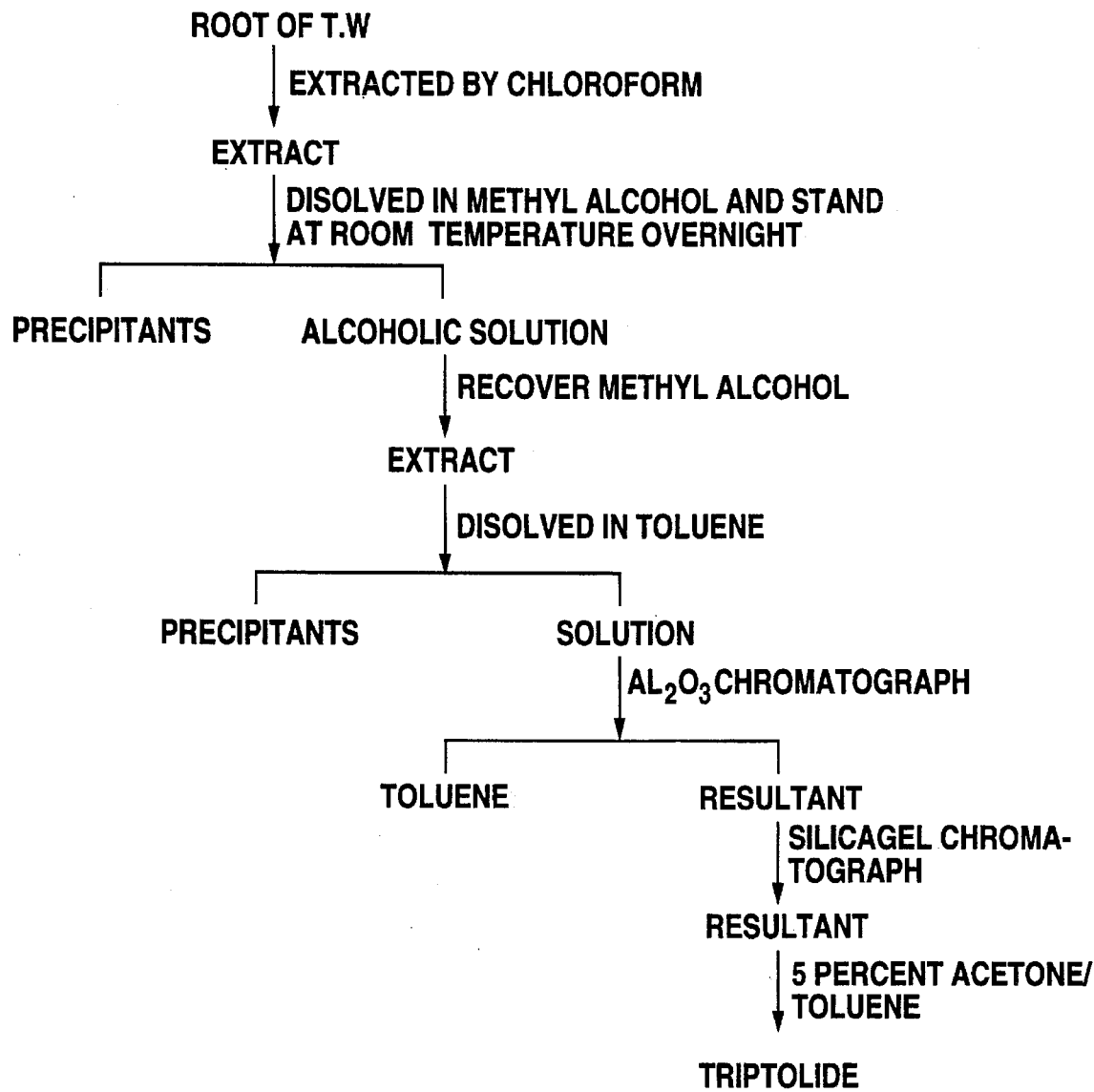
FIG. 17 outline the extraction procedure for preparation of triptolide.

The structures of triptolide and tripdiolide are shown in FIG. 11. FIG. 12 shows the structure of triptonide. Triptolide was isolated from alcoholic extracts of *Tripterygium wilfordii* Hook F by the method of Kupchan et al.[31]. This scheme for triptolide preparation is outlined in FIG. 17. The present example demonstrates the effects of the $T_2$ extract (described in Example 1) or triptolide on the in cellulo of viability of important immunopotent cells.

The effect of triptolide on immunopotent cells in vitro was determined as follows:

T cells, B cells and fibroblasts ($1\times10^6$/ml) were incubated with varying concentrations of $T_2$ or triptolide for 72 hr. The cells were assayed for cell viability by using a cytoflowmeter (FACSCAN) after the cells were stained with propidium iodine. Table 14 demonstrates the effect of $T_2$ or triptolide on cell viability.

TABLE 14

EFFECT OF $T_2$ OR TRIPTOLIDE ON CELL VIABILITY

| | Inhibitors | | | | | | | |
|---|---|---|---|---|---|---|---|---|
| | | $T_2$ (µg/ml) | | | | Triptolide (ng/ml) | | |
| Cell type | Control | 0.1 | 1.0 | 10.0 | 100.0 | 0.1 | 1.0 | 10.0 |
| | (Percent viable cells) | | | | | | | |
| T cells | 91.7 | 90.0 | 89.3 | 88.2 | 18.8 | 29.5 | 29.8 | 11.5 |
| B cells | 55.6 | 50.9 | 44.3 | 30.5 | 10.6 | 20.9 | 20.9 | 15.6 |
| Fibroblasts | 77.5 | 92.7 | 95.1 | 86.6 | 43.0 | 91.7 | 89.3 | 35.8 |

$T_2$ at 100 µg/ml and triptolide at 10 ng/ml were toxic to fibroblasts indicating that at these levels, toxicity is nonspecific. At lower levels, suppression of T cell and B cell function is seen.

The capacity of triptolide to inhibit in vitro responses of human lymphocytes was examined. As can be seen in table 15, triptolide inhibited proliferation of both T and B lymphocytes profoundly at concentrations of 0.1–1.0 ng/ml.

TABLE 15

| Concentration of triptolide (ng/ml) | PHA-Induced T Cell DNA Synthesis | SA-Induced B Cell DNA Synthesis |
|---|---|---|
| | ($^3$H-Thymidine Incorporation, CPM) | |
| 0 | 93,400 | 7,900 |
| 0.1 | 24,200 | 2,000 |
| 1.0 | 100 | 100 |

Figure 13:
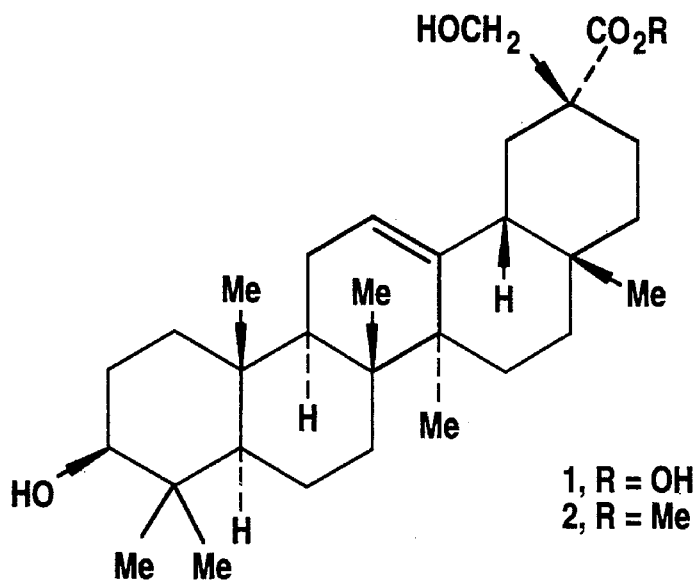
FIG. 13 schematically describes the structure of wilfortrine (1) and wilfortrine methyl ester (2).
Figure 14:
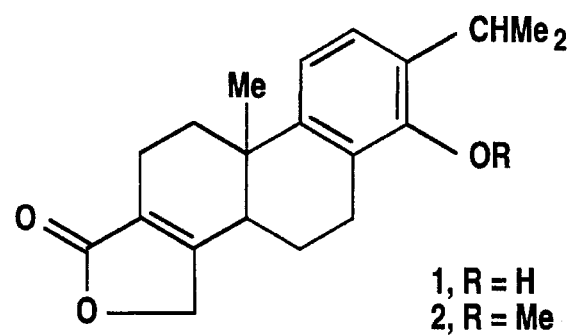
FIG. 14 shows the structure of triptophenolide (1) and triptophenolide methyl ester (2).
Figure 15:
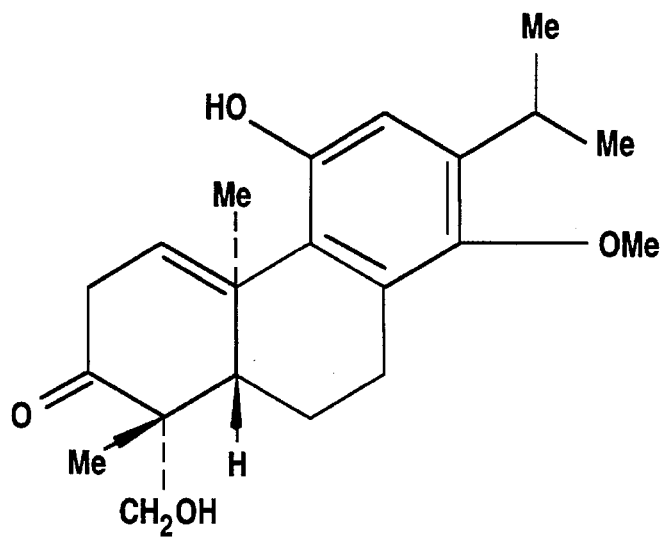
FIG. 15 schematically shows the structure of triptonoterpenol.
Figure 16:
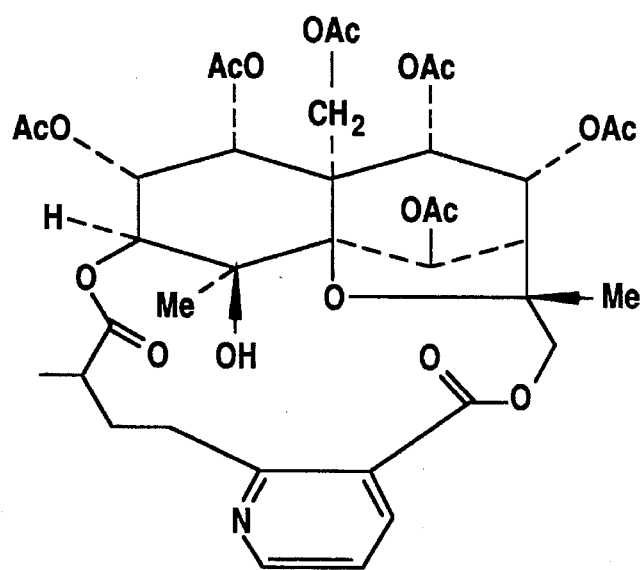
FIG. 16 schematically shows the structure of wilformine.

Additional studies indicated that this triptolide fraction also inhibited the in vitro production of immunoglobulin from mitogen stimulated human B lymphocytes at comparably small concentrations. These results demonstrate that the triptolide fraction is extremely toxic, however, its specificity of action is yet to be determined. Other components of *Tripterygium wilfordii* Hook F include:

polpunonic acid (wilfortrine) (1) and the methyl ester thereof (2) shown in FIG. 13 and described by Keng et al. (Chem. Abst. 107:55718y, p436, 1987);

triptophenolide (1) and triptophenolide methyl ether (2) shown in FIG. 14 and described by Wu et al. (Chem. Abst. 107:96917f, p712, 1987);

triptonoterpenol shown in FIG. 15 and described by Deng et al. (Chem. Abst. 107:112684k, p112692, 1987); and wilformine (shown in FIG. 16), wilforine, wilforgine, and wilforzine described by He et al. (Chem. Abst. 107:130906p, 1987;

Purified components of the *T. wilfordii* extract that have essentially undetectable concentrations of triptolide will be administered to patients with autoimmune and inflammatory diseases including rheumatoid arthritis, systemic lupus erythematosus and psoriasis. Dosage will be determined based on the concentration of each therapeutic component in the T. mixture.

EXAMPLE 5

Ethyl Acetate Preparation of *Tripterygium wilfordii* Hook F

The present example is provided to demonstrate that the preparation of *Tripterygium wilfordii* Hook F may be obtained using a variety of extraction protocols, including extraction by ethyl acetate.

An extract of the *Tripterygium wilfordii* Hook F root was prepared employing an ethyl acetate extraction protocol. It is proposed that the ethyl acetate extract will be administered orally in clinical use.

To prepare the ethyl acetate extract, roots of TWH obtained from Fujian Province of China were peeled and dried in the open air and in the sunlight. Roots obtained from other geographical areas are also expected to be equally useful. The plant wood may also be dried using other techniques including a low heat oven or incubator that will reach temperatures of about 60° C. The woody parts of the root were ground to a powder. One thousand grams of the coarse powder of TWH were extracted with 2500 ml of 95% ethanol for 24 hours. The extracted material was collected in 5000 ml of 95% ethanol. The plant residue was refluxed with 95% ethanol for 2 hours and the ethanol extract was combined with the initial extract. The combination was evaporated under reduced pressure until all ethanol was removed.

The concentrated ethanol extract was dissolved in ethyl acetate with the aid of ultrasonification. The ethyl acetate extract was filtered and the residue was dissolved with ethyl acetate repeatedly. The ethyl acetate extract was combined, filtered and evaporated to dryness under reduced pressure. The material was ground into a fine powder and mixed with starch. The mixed powder was further screened through a #60 sieve.

The mixed powder will be incorporated into capsules suitable for human use using techniques well known to those of ordinary skill in the art[61] (see Remington's Pharmaceutical Sciences, 18th ed. (1990) for clinical trials which reference is specifically incorporated herein by reference for this purpose). In some embodiments, one tablet will contain about 30 mg of the ethyl acetate extract. The ethyl acetate extract contains little triptolide, and the tablets will contain reduced amounts of triptolide, defined for purposes of the present invention as preferably no more than 10 μg to 20 μg of triptolide. Triptolide was measured with HPLC by comparison with a known standard of triptolide as described in Example 4 and FIG. 17. A single batch of 1400 gm was prepared and utilized for the pre-clinical evaluation described below.

Thin layer chromatographic scanner analysis carried out at Southwestern Medical Center at Dallas showed that the average triptolide content of the Chinese EA extract from different batches manufactured by Huang Shi Pharmaceutical Company was 1.33 μg per mg[44,45]. The ethyl acetate extract produced by the present inventors contained much lower concentrations of triptolide of about 0.22 μg of triptolide per mg of extract. Analysis by TLC and HPLC indicated that the Chinese and Texas EA extracts contained some similar components (FIG. 21).

Comparative Studies

Comparison of the diterpenes in the ethyl acetate extracts of *Tripterygium wilfordii* Hook F prepared in China and Texas was performed. 330 mg of the Texas ethyl acetate extract and 40 mg of the Chinese ethyl acetate extract were dissolved in ethyl acetate at a concentration of 66 mg/ml and 8 mg/ml, respectively, followed by sonication for 25 minutes and filtration in vacuum. The ethyl acetate solution was passed through a 5 g neutral $Al_2O_3$ column. The material was eluted with 30 ml of ethanol. After the ethanol elution was pooled with the ethyl acetate solution, the mixed solution was evaporated under nitrogen air till dryness. The residues were dissolved in 1 ml and 0.4 ml of chloroform, separately. 20 μl of each solution were applied to 20×20 cm silica gel G F 254 plate (polyester backing, 250 μm layer) and resolved with chloroform followed by chloroform/ether (1:4). Triptolide (3.6 μg), triptophenolide (10 μg) and tripdiolide (1.8 μg) served as reference standards. After the plates were air-dried, the diterpenes were visualized by the Kedde reaction. The relative concentrations of triptophenolide, triptolide and tripdiolide in the Chinese and Texas ethyl acetate extracts and a standard extract were performed. The results of this study are shown in FIG. 21. *TEA: the ethyl acetate extract of *Tripterygium wilfordii* Hook F prepared at UT Southwestern Medical Center at Dallas. **CEA: the ethyl acetate extract of *Tripterygium wilfordii* Hook F prepared in China.

Figure 21:
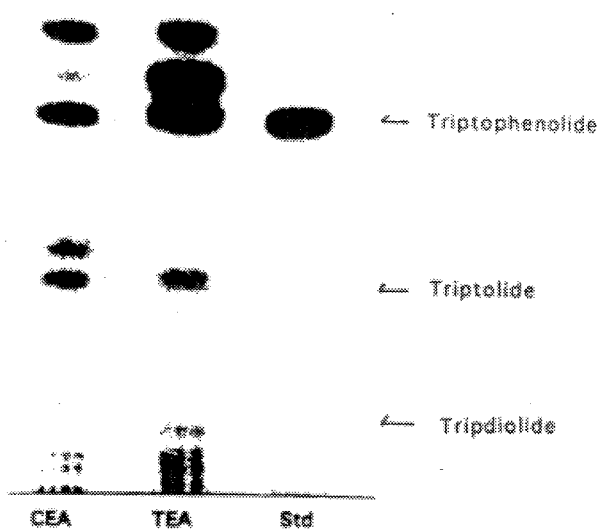
FIG. 21 shows a comparison of the diterpenes in the ethyl acetate extracts of *Tripterygium wilfordii* Hook F prepared in China (CEA) and Texas (TEA). The diterpenes of each T. wilfordii Hook F preparation (CEA and TEA) were visualized by the Kedde reaction. Triptolide (3.6 μg), triptophenolide (10 μg) and tripdiolide (1.8 μg) served as reference standards. The relative concentrations of triptophenolide, triptolide and tripdiolide of the CEA and TEA extracts are seen in this figure.

As shown in FIG. 21, the Texas ethyl acetate extract evidenced a more heavy staining band for triptophenolide than did the Chinese ethyl acetate extract, yet about equal to that of the standard. In contrast, the band for triptolide was more intense for the Chinese extract as compared to the Texas ethyl acetate extract. These findings demonstrate that there is more triptolide in the Chinese extract (because it is made from unskinned roots). Therefore the Chinese extract is more toxic.

Stability

The Texas ethyl acetate extract is stable at room temperature for at least 1 year. Photosensitivity of the extract is unclear, and therefore, it is stored in the dark. It is expected that the preparation will remain stable for at least 8 years.

EXAMPLE 6

In Cellulo Activity of the Texas Ethyl Acetate Extract

Initial attempts to understand the mechanism of the action of the ethyl acetate extract focused on its potential immunosuppressive activities. The present example demonstrates the significant in cellulo activity of the extract on antigen and mitogen-induced T cell proliferation and IL-2 production.

The ethyl acetate extract was prepared as outlined in Example 5. The ethyl acetate extract exerted a number of immunosuppressive effects on human immune responsiveness, including antigen and mitogen-induced T cell proliferation and IL-2 production. In cellulo (i.e., studies using intact whole cells) studies were carried out to determine the concentration of the extract that inhibited mitogen or antigen induced human T cell proliferation and IL-2 production by T cells by 50% ($ID_{50}$).

Materials and Methods

Proliferation Studies: T cells were cultured with or without PHA (0.5 μg/ml) in the presence or absence of the ethyl acetate extract at doses of 5.7 μg/ml, 7.3 μg/ml, 0.08 μg/ml, 1.32 μg/ml, 0.7 μg/ml and 1.0 μg/ml for 3 days. Significant effects on T cell proliferation were observed.

IL-2 Production Studies: The effects of the ethyl acetate extract on IL-2 production was examined. T cells were cultured with or without PHA (1 μg/ml) in the presence or absence of the extract at doses of 3.6 μg/ml, 3.9 μg/ml and 0.83 μg/ml. Significant effects on IL-2 production in the presence of either PHA or T.T. were observed (see Table 16).

The ethyl acetate extract at concentrations of 0.08–5.7 μg/ml inhibited proliferation and IL-2 production by about 50%. The concentrations of the extract that induced death of about 50% of cells was also determined ($LD_{50}$). The $LD_{50}$ of the extract on the mitogen or antigen activated T cells ranged from 17–70.5 μg/ml, which was 10–225 times the corresponding $ID_{50}$ (Table 16). These results demonstrate that the TEA extract retained strong potency for immunosuppressive activities in cellulo.

Much larger amounts of the ethyl acetate extract may be used with a significantly reduced toxicity level. Therefore, the ethyl acetate extract would be expected to be relatively safer than the $T_2$ extract.

TABLE 16

IN CELLULO $ID_{50}$ AND $LD_{50}$ OF THE
ETHYL ACETATE EXTRACT ON HUMAN PBMCS

| Assay | Stimulus | Length of Culture | $ID_{50}$ (μg/ml) | $LD_{50}$ (mg/per ml) |
|---|---|---|---|---|
| Proliferation | | | | |
| | PHA (1 μg/ml) | 2.5 days | 5.7 | 70.5 |
| | PHA (1 μg/ml) + IL-2 (25 u/ml) | 2.5 days | 7.3 | 74.2 |
| | T.T (10 μg/ml) | 5 days | 0.08 | 18.8 |
| | T.T (10 μg/ml) | 5 days | 1.32 | 17.0 |

TABLE 16-continued

IN CELLULO ID$_{50}$ AND LD$_{50}$ OF THE
ETHYL ACETATE EXTRACT ON HUMAN PBMCS

| Assay | Stimulus | Length of Culture | ID$_{50}$ (μg/ml) | LD$_{50}$ (mg/per ml) |
|---|---|---|---|---|
| | + IL-2 (25 u/ml) | | | |
| | SK (1 mg/ml) | 5 days | 0.7 | 20.0 |
| | SK + (1 mg/ml) + IL-2 (25 u/ml) | 5 days | 1.0 | 19.8 |
| IL-2 production | | | | |
| | PHA (1 μg/ml) | 24 hrs. | 3.6 | |
| | PHA (1 μg/ml) | 24 hrs. | 3.9 | |
| | T.T. (10 μg/ml) | 24 hrs. | 0.83 | |

PHA, phytohemagglutinin; TT, tetanus toxoid; SK, streptokinase.

EXAMPLE 7

In Vivo Animal Studies Of The Efficacy Of Ethyl Acetate Extract Of TWF

The present example describes studies that were conducted to demonstrate that the ethyl acetate extract of *T. wilfordii* exerts an immunosuppressive action on primary antibody responses in vivo. In these studies, mice (C57 BL/6J) were immunized with TNP-BSA emulsified with complete Freund's adjuvant, according to techniques well known to those of skill in the art. The ethyl acetate extract was prepared as outlined in Example 5. On the day of immunization, the mice were treated with the ethyl acetate extract at 125 or 250 mg/kg/day orally. In other studies, mice were immunized with phosphorylcholine-KLH emulsified with complete Freund's adjuvant 30 days after the beginning of treatment with the ethyl acetate extract. Sera were harvested 10 and 26 days after immunization. Antibodies against TNP, TNP-BSA or PC-KLH in these sera were determined by the ELISA method. The ELISA method is a standard immunoreactivity assay well known to those of skill in the art.

Results from these studies show that the primary antibody responses to each of these antigens were markedly decreased in the mice treated with the ethyl acetate extract (Table 17). Treatment beginning 30 days before immunization was the most effective at suppressing antibody responses, but treatment beginning on the day of immunization also significantly diminished antibody responses.

TABLE 17

EFFECT OF TREATMENT OF MICE WITH THE TEA EXTRACT ON
THEIR CAPACITY TO GENERATE PRIMARY ANTIBODY RESPONSES

| | | Treatment with the Ethyl Acetate Extract | | | | |
|---|---|---|---|---|---|---|
| Antigen Immunization | Assay | Daily dose (mg/kg of body weight) | before immunization (days) | after immunization (days) | Antibody Serum Dilution | OD |
| PC-KLH | PC-KLH | 0 | 30 | 10 | 1:80 | .250 |
| | | 125 | 30 | 10 | | .133 |
| | | 250 | 30 | 10 | | .084 |
| TNP-BSA | TNP-BSA | 0 | 0 | 10 | 1:320 | .671 |
| | | 125 | 0 | 10 | | .373 |
| | | 250 | 0 | 10 | | .454 |
| | | 0 | 0 | 26 | 1:5120 | .528 |
| | | 125 | 0 | 26 | | .364 |
| | | 250 | 0 | 26 | | .282 |
| TNP-KLH | TNP | 0 | 0 | 10 | 1:20 | .414 |
| | | 125 | 0 | 10 | | .375 |
| | | 250 | 0 | 10 | | .768 |
| | | 0 | 0 | 26 | 1:320 | .639 |
| | | 125 | 0 | 26 | | .552 |
| | | 250 | 0 | 26 | | .280 |

C57 BL/6J mice (5 in each group) were treated without or with varying doses of the ethyl acetate extract orally. 100 mg of the antigens emulsified in 0.1 ml of complete Freund's adjuvant were injected intraperitoneally on the same day as the EA treatment started or 30 days after the beginning of treatment with the TEA extract. Blood was taken from the tail vein on the 10th or 26th day after immunization. Antibodies against TNP alone or TNP-BSA or PC-KLH in the sera were determined with ELISA. Relative amount of antibodies in the sera was estimated by comparing the O.D. readings of each sample at the same dilution for individual assays. Multiple dilutions of serum were assayed and data shown for the dilutions at which all readings were on the linear part of the curve.

EXAMPLE 8

Toxicity of Ethyl Acetate Extracts

The present example is provided to demonstrate the reduced toxicity of the TWF preparations, particularly the ethyl acetate extract of the present invention as compared to other *T. wilfordii* extracts.

Acute toxicity testing was carried out using C57 BL/6J mice. For the initial studies, 25 mice (5 in each group) were used to estimate the approximate $LD_{50}$. No deaths developed with the ethyl acetate preparation of *T. wilfordii* until very high doses of 1200 mg/kg were administered. Eighty percent of the mice treated with 1400 mg/kg of the ethyl acetate extract died. Following this, 50 mice of the same strain were divided into 5 groups with equal numbers of each sex in each group. Mice were given a single dose of the ethyl acetate extract orally at 0, 1100, 1150, 1230, 1350 and 1500 mg/kg body weight. The mice were observed for 7 days thereafter. The $LD_{50}$ was estimated according to the Spearman-Karber Method[62]. $LD_{50}$ of the ethyl acetate extract from this experiment was 1253 mg/kg/day (Table 19). All death occurred within the first 3 days of the study.

TABLE 18

ACUTE TOXICITY TEST OF THE ETHYL ACETATE EXTRACT IN MICE

| Dose (mg/kg) | Xi | Ri | Ni | Pi | $\frac{Pi + Pi + 1}{2}$ | I |
|---|---|---|---|---|---|---|
| 1100 | 3.04 | 0 | 10 | 0 | 0.15 | 0.02 |
| 1150 | 3.06 | 3 | 10 | 0.3 | 0.35 | 0.03 |
| 1230 | 3.09 | 4 | 10 | 0.4 | 0.55 | 0.04 |
| 1350 | 3.13 | 7 | 10 | 0.7 | 0.85 | 0.05 |
| 1500 | 3.18 | 10 | 10 | 1.0 | | |

50 mice (C57BL/6j) were randomly divided into 5 groups with equal numbers of each sex for each group. The mice were treated with various doses of the ethyl acetate extract as indicated orally for 7 days. The number of dying mice was recorded. $LD_{50}$ was calculated according to Spearman - Karber method: If $X = LD_{50}$,
Log $X = X_k - \Sigma [(Pi + Pi_{+1}) \times I \times 0.5]$.
Log $X = 3.098$
$LD_{50} = 1253.1$ mg/Kg.
$Xi = Log_{dose}$; $Ri$ = number of dying mice; $Ni$ = number of tested mice; $Pi = (Ri/Ni)$; $I = Xi_{+1} - Xi$; $X_k$ = the logarithm of the dose (k) at which all treated animals died.

Autopsy was performed immediately after death of the mice. Histological examination demonstrated marked lymphocytic necrosis of splenic germinal centers and thymus, with only mild changes in liver, kidney, lung or brain of some of the animals.

TABLE 19

COMPARISON OF THE TEXAS WITH THE CHINESE ETHYL ACETATE EXTRACT

| | EA Extract | |
|---|---|---|
| | Texas | Chinese |
| Source of plant material | Fujian province | Hubei province |
| Portion of the plant the EA extracted from | woody portion of the roots | whole roots |
| Triptolide content | | |
| (μg/gm of plant material) | 4.80 | 27.50 |
| (μg/mg of the EA extract) | 0.22 | 1.33 |
| $ID_{50}$ (in vitro on PHA stimulated human T cell proliferation, μg/ml) | 5.7 | 2.0 |
| $LD_{50}$ (on mice, mg/kg of body weight) | 1253 | 764* |
| $ID_{50}$ in vitro T-cell proliferation/$LD_{50}$ ratio (on mice) | $4.5 \times 10^{-3}$ | $2.6 \times 10^{-3}$ |

*The average of the $LD_{50}$ of different batches of tablets of the CEA extract prepared from TWH obtained from different counties or provinces of China.

As shown in Table 19, the $LD_{50}$ dose of the Chinese preparation is about 764 mg/kg as compared to 1253 mg/kg for the Texas extract. The $LD_{50}$ of $T_2$ in mice has been reported to be 159.7±14.3 mg/kg 40 and the $LD_{50}$ of the Chinese extract varied from 608–858 mg/kg. The $ID_{50}$ of the Chinese preparation is 2.0 μg/ml as compared to 5.7 for the Texas extract. The $ID_{50}/LD_{50}$ ratio of the Chinese extract is $2.6 \times 10^{-3}$. This therapeutic activity:toxic index value is significantly lower than the $ID_{50}/LD_{50}$ ratio of the TEA extract, $ID_{50}:LD_{50}=4.5\times10^{-3}$. The ratios of each of the extracts as calculated with the data presented in Table 19 indicate that the Texas extract has a superior therapeutic activity:toxic index balance, and thus is superior as a therapeutic preparation compared to preparations of TwHF described in the literature.

EXAMPLE 9

In Vivo Use Of Texas Ethyl Acetate Extract

The present example is provided to outline the use of the Texas ethyl acetate extract in animals, particularly humans.

The dosage schedule of the ethyl acetate extract to be used in initial escalation and safety studies will be calculated using the $LD_{50}$ of the extract and its triptolide content. The Texas ethyl acetate extract was processed using the same procedure as used in China to produce the Chinese ethyl acetate extract with the exception that the material prepared as the Texas ethyl acetate extract is extracted from the peeled woody portion of the roots of TWH. The Chinese extract is extracted from the whole root of the plant. The reported dosage of the Chinese extract will be employed as a reference for calculating the dosage of the Texas ethyl acetate extract (Table 19). The Chinese literature reports that 60–120 mg/day of the CEA extract is safe and effective in the treatment of RA (Shu et al., 1989; Hubei cooperative study group, 1981). This amount of the Chinese extract contains 131.2–262.4 μg of triptolide per tablet. Clinical trials with the Texas extract will employ escalating doses of 30 mg, 60 mg and 120 mg/day in three divided doses. The lowest dose is equivalent to approximately 25% of the smaller dosage of the Chinese extract used safely in China whereas the highest dosage (120 mg dose of the TEA extract) approximates the lowest dosage of the CEA extract used in China and contains 26.4 μg of triptolide.

Administration of extracts of TWH are contraindicated in patients with leukopenia, thrombocytopenia, and impaired liver or kidney function. Studies have not been done to assess the effects of the extracts on pregnant or lactating women.

Patients will discontinue treatment with extracts of TWH if they develop any of the following: persistent vomiting or diarrhea; profound anorexia; WBC count of ≦2,500 cells/mm³ or platelet count of ≦100,000 cells. Patients who develop these symptoms should be monitored frequently for white blood cell counts, as well as liver and kidney function.

EXAMPLE 10

Fraction 924 of TWF-Characterization and Identification

The present example is provided to detail the biological activity of a fraction 924 component of a *T. wilfordii* ethyl acetate extract.

Based on previous examples, the present inventors were aware that many diterpenoid compounds of TwHF, such as triptolide, possess suppressive capacity on both in vitro and in vivo immune functions. The molecular groups responsible for the immune suppressive function of these compounds are unknown, however, the core structure of diterpenoids which may be related to their activity consists of an α-β-unsaturated 5 element lactone which can be identified by Kedde reagents. HPLC was used to fractionate the ethyl acetate extract of TwHF and the Kedde reagents were employed to trace the fractions. Then, the effect of selected fractions on the in vitro IL-2 production and [$^3$H]-thymidine incorporation by PHA-activated T cells was determined. Fractions that inhibit these T cell functions were selected and the chromatographic pattern was identified with HPLC. One fraction was further purified with HPLC and crystallized repeatedly; a pure, crystallized compound was obtained and designated "924".

Purification of a 924 Fraction from an Ethyl Acetate Extract

The dried woody skinned part of the root of TwHF was extracted with ethanol. The solution was concentrated at reduced pressure, and the residue was dissolved in ethyl acetate. This solution was passed through $Al_2O_3$ with ethanol as an eluent. The eluate was evaporated and the residue chromatographed on silica gel with chloroform, chloroform-ether and ethyl acetate as successive eluent. The fractions eluted with chloroform-ether were purified on a preparative HPLC column packed with Nova-Pak C18 and equipped with a 214 detector. Methanol-water was the mobile phase. A fraction having positive reaction to Kedde reagent was collected and extracted with chloroform. The chloroform solution was evaporated to dryness and the residue crystallized in dichloromethane-hexane to yield 924. "924" is soluble in ethanol, and ethanol and chloroform.

The "924" fraction inhibited DNA synthesis by T cells stimulated with PHA. The "924" fraction at a concentration of 1 ng/ml or more inhibited PHA-stimulated T cells to uptake [$^3$H] thymidine. The inhibition capacity was correlated with the concentrations of the compound. The slope of the inhibition curve of "924" on T cell proliferation was quite flat in that the degree of inhibition changed from 14.6% to 54.2% when the concentration of "924" increased from 1 ng/ml to 100 ng/ml. This was different from some components of TwHF, such as triptolide or tripdiolide which exerted potent immunosuppressive action with increase in its concentrations at the level of ngs, and resulted in significant enhancement of the inhibition of the cell function.

Figure 20B:
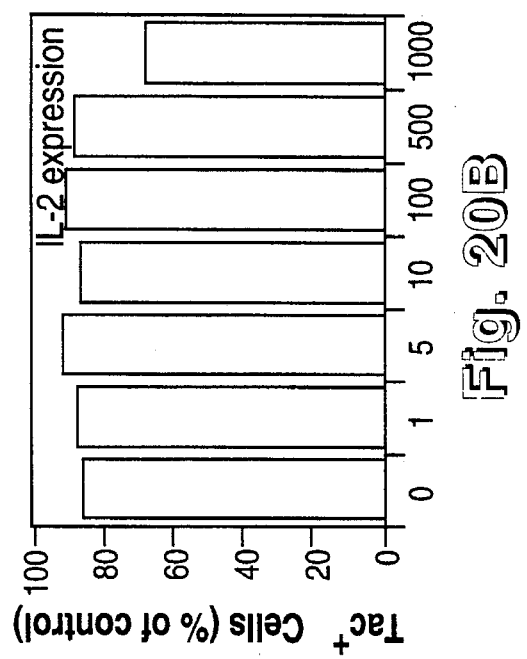
FIG. 20A, FIG. 20B, FIG. 20C and FIG.20D show the function of Fraction 924; 22A shows the effect of Fraction 924 on IL-2 production; 22B, the effect on IL-2 expression; 22C, the effect on T-cell proliferation; and 22D, the effect on cell viability.

The "924" fraction inhibited IL-2 production by PHA-stimulated T cells. Similar with the pattern of the inhibitory effect of "924" on T cell DNA synthesis, at the inhibitory concentrations, "924" was able to reduce the production of IL-2 by PHA-induced T cells. A 50% reduction of IL-2 secretion was seen at 42.11 ng/ml (see FIG. 20B).

Figure 20D:
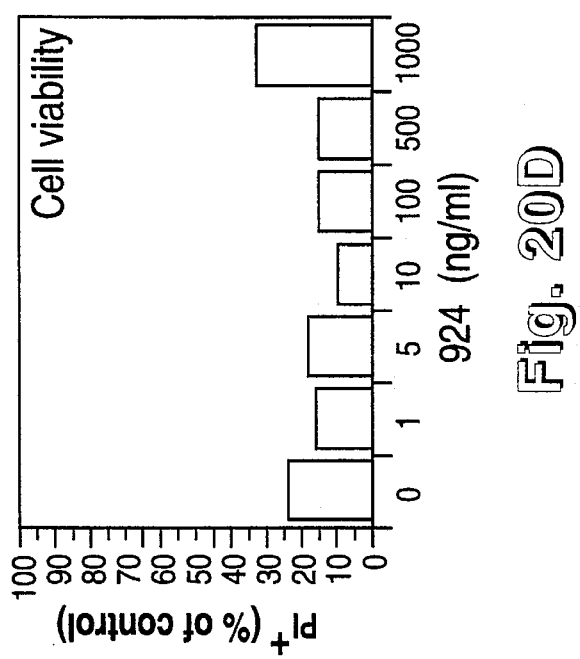
Figure 20A:
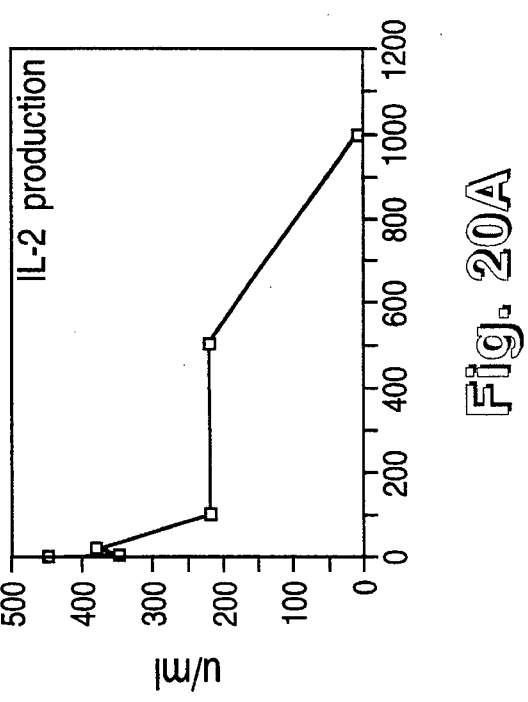
Figure 20C:
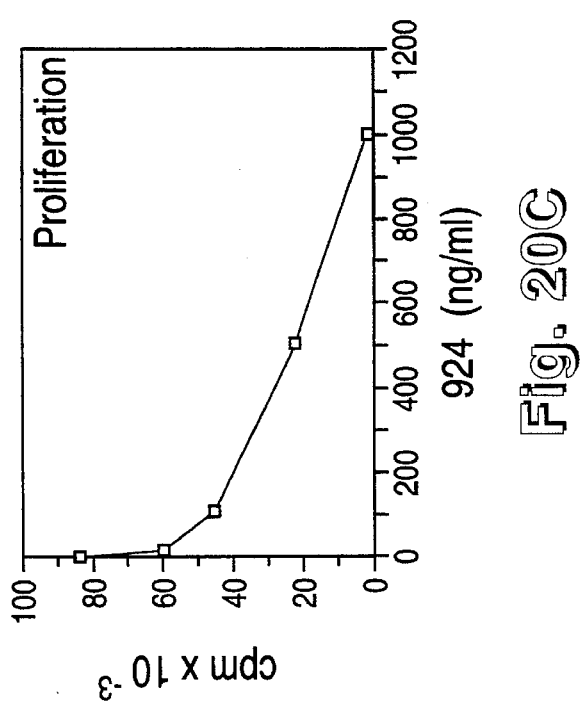

The 924 fraction also demonstrated significant activity in inhibiting proliferation of T cells, providing for inhibition of T cell proliferation at relatively low doses of 200 ng/ml of fraction 924 (see FIG. 20C). At concentrations of 1,000 ng/ml fraction 924, no cell proliferation was evident (see FIG. 20C). There was no effect of "924" on IL-2R expression by PHA-activated T cells. Fraction "924" at 500 ng/ml (at least 50 times the concentration effective to inhibit T cell proliferation or IL-2 production) did not affect the IL-2R expression by PHA-activated T cells.

Fraction "924" did not affect the viability of PHA-stimulated T cells at all employed concentrations, ranging from 1 ng/ml up to 1000 ng/ml. The in vitro $ID_{50}/LD_{50}$ of "924" of T cell proliferation was more than 10 indicating that, under the same cultural conditions, "924" did not increase cell death until it reached to 10 times more than its inhibitory concentration. The 924 fraction also demonstrated relatively low cell toxicity, as demonstrated in FIG. 20D. Concentrations of the 924 fraction of between 1 and 500 ng/ml did not differ significantly in terms of cell viability, expressed as a percent of viable cells in the control population. A 924 fraction concentration of 1,000 ng/ml was only slightly more toxic to cell viability as compared to the 0 ng/ml dose (see FIG. 20D, 0 ng/ml=22% of control; 1,000 ng/ml fraction 924=35% of control cell viability).

Figure 18:
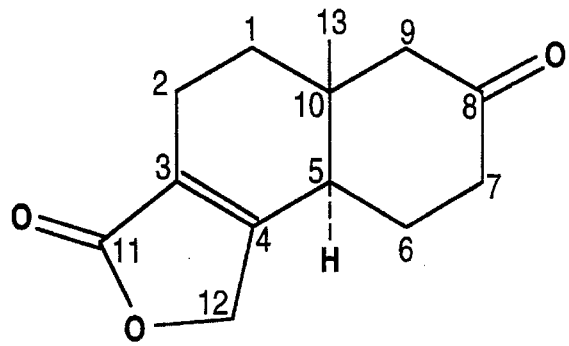
FIG. 18 depicts the structure of wilforonide (naphtho-[1,2-c]furan-3,7(1H,5H)-dione, 4,5a,6,8,9,9a-hexahydro-5a-methyl-(5aR-trans)-[104331–87–5]).
Figure 19A:
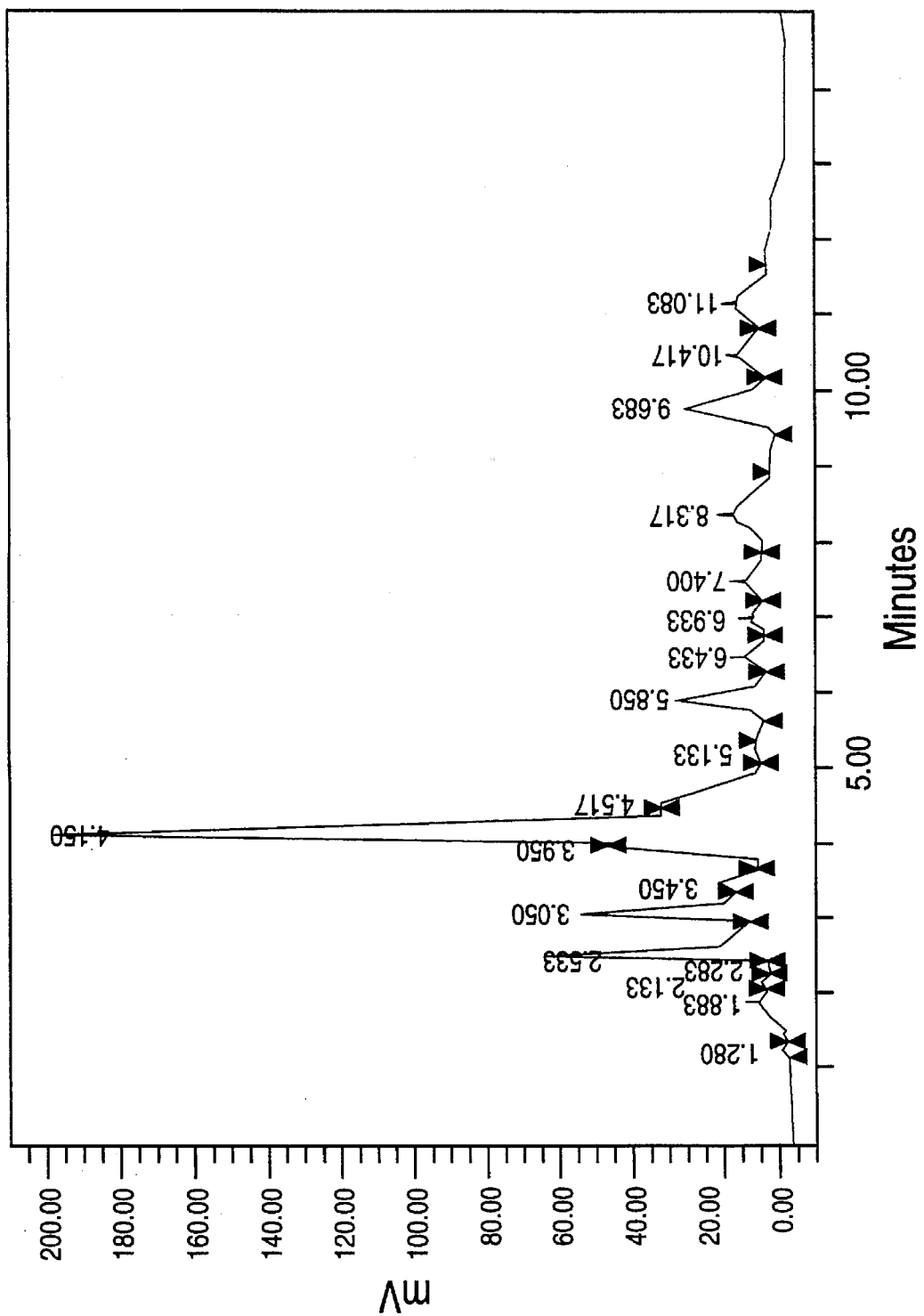
FIG. 19A and FIG. 19B show the elution profile of Fraction 924.
Figure 19B:
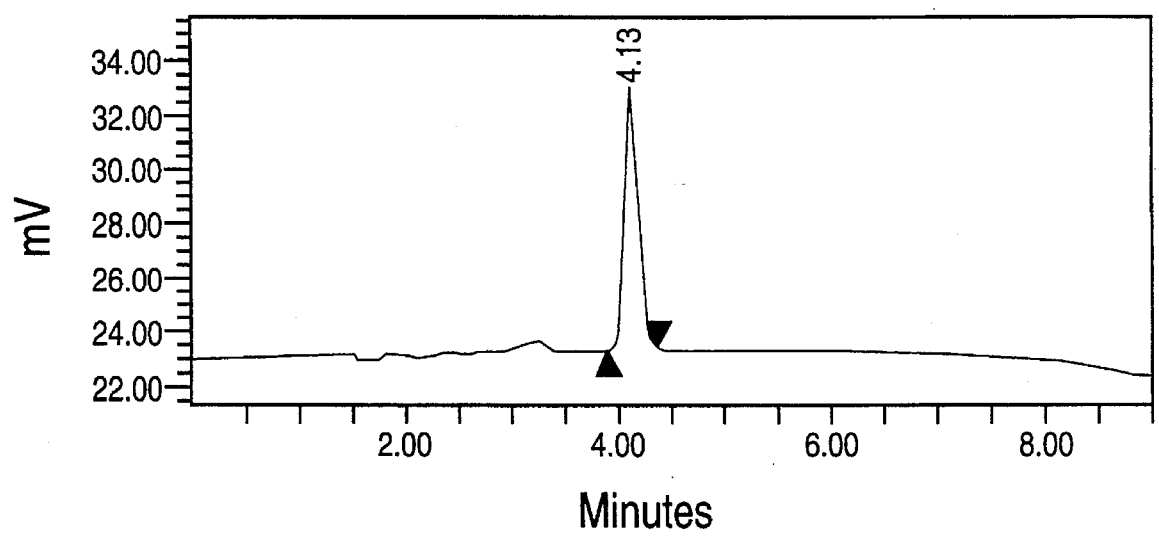

The positive reaction to Kedde reagent indicated that "924" has a structure of an $\alpha,\beta$-unsaturated lactone. Since many of the known diterpenoid compounds such as triptolide, triptochlorolide, 16-hydroxytriptolide, tripdiolide, triptonide and triptophenolide also have the $\alpha,\beta$-unsaturated lactone, the TLC and HPLC patterns of "924" were compared with these compounds. The pattern of "924" was different from that of all of the above mentioned compounds. The pattern did not have the chromatographic characteristics of diterpenoids and did not follow the regular pattern of diterpenoids tested by several normal and reverse phase chromatographic systems. Therefore, "924" seems to be a non-diterpenoid compound. Upon further analysis of the 924 fraction by NMR/mass spectroscopy, the fraction was determined to be the pure compound, wilforonide (FIG. 18).

EXAMPLE 11

Immunosuppressive Effects of Wilforonide

T cells were cultured with or without PHA(0.5 micrograms/ml) in the presence or absence of either, 10 ng/ml, 50 ng/ml, 100 ng/ml, 200 ng/ml or 500 ng/ml concentrations of the wilforonide preparation described in Example 10 for three days. [$^3$H] thymidine was added for the last 14 hours of culture. Each concentration was run in quadruplicate (4 times) and the results for each concentration averaged to provide a mean. The mean cpm $\times 10^3$ values were combined and expressed as a percent of T cell inhibition. These data are provided at Table 20.

As shown in Table 20, a concentration of 100 ng/ml wilforonide provided a 21.19% inhibition of PHA-induced T cell proliferation in cellulo. A concentration of 200 ng/ml wilforonide provided a 26.43% inhibition of PHA-induced T cell proliferation. A concentration of 500 ng/ml wilforonide resulted in a 62.86% inhibition of PHA-induced T cell proliferation (see Table 20). An $ID_{50}$ of 391.30 ng/ml wilforonide was observed (see Table 20).

TABLE 20

| EFFECT OF WILFORONIDE ON PHA-INDUCED T CELL PROLIFERATION* | | | | | | |
|---|---|---|---|---|---|---|
| Wilforonide | cpm $\times 10^3$ | | | | Mean | % |
| (ng/ml) | 1. | 2. | 3. | 4. | cpm $\times 10^3$ | inhibition |
| 0 | 34.1 | 36.9 | 58.5 | 38.5 | 42.0 | |
| 10 | 23.5 | 37.1 | 57.5 | 36.3 | 38.6 | 8.09 |
| 50 | 30.2 | 35.3 | 57.0 | 44.8 | 41.8 | 0.48 |
| 100 | 13.0 | 37.6 | 55.2 | 26.7 | 33.1 | 21.19 |
| 200 | 6.8 | 33.9 | 56.5 | 26.4 | 30.9 | 26.43 |
| 500 | 0.3 | 19.7 | 30.9 | 11.3 | 15.6 | 62.86 |
| $ID_{50}$ (ng/ml) | | | | | | 391.30 |

*T cells were cultured with or without PHA (0.5 µg/ml) in the presence or absence of the indicated concentrations of wilforonide for 3 days. [$^3$H]-Thymidine was added for the last 14 hours. Data are from 4 independent experiments.

Effect of Wilforonide on PHA-Induced IL-2 Production

The effects of wilforonide on IL-2 production was also examined. T cells were cultured with or without PHA(1 microgram/ml) in the presence or absence of 0 (control), 10 ng/ml, 50 ng/ml, 100 ng/ml or 200 ng/ml wilforonide overnight. Cell-free supernatants were diluted 1 to 80 and the IL-2 content assayed with CTLL-2 cells. IL-2 production by the T cells cultured without stimulation was found to be less than 0.32 units/mi.

The results obtained from the study are provided in Table 21. The 10 ng/ml concentration of wilforonide evidenced a 37.94% inhibition of PHA-induced IL-2 production relative to control. The 50 ng/ml concentration of wilforonide resulted in a 54.22% inhibition of PHA-induced IL-2 production relative to control. Concentrations of 100 NG/ML resulted in a 68.20% inhibition, with the 200 ng/ml wilforonide concentration resulting in a 74.96% inhibition of PHA-induced IL-2 production.

An overall $ID_{50}$ of 42.11 ng/ml was also determined. These data are provided in Table 21.

TABLE 21

EFFECT OF WILFORONIDE ON PHA-INDUCED IL-2 PRODUCTION*

| Wilforonide | IL-2 (unit/ml) | | | | | % |
|---|---|---|---|---|---|---|
| (ng/ml) | 1. | 2. | 3. | 4. | Mean | inhibition |
| 0 | 1.422 | 23.436 | 50.020 | 10.701 | 21.395 | |
| 10 | 1.628 | 20.723 | 27.374 | 3.385 | 13.278 | 37.94 |
| 50 | 1.664 | 26.983 | 4.509 | 6.042 | 9.795 | 54.22 |
| 100 | 0.800 | 11.160 | 10.170 | 4.982 | 6.803 | 68.20 |
| 200 | 0.850 | 10.301 | 8.502 | 1.773 | 5.357 | 74.96 |
| $ID_{50}$ (ng/ml) | | | | | | 42.11 |

*T cells were cultured with or without PHA (1 μg/ml) in the presence or absence of the indicated concentrations of wilforonide overnight. Cell-free supernatants were diluted 1 to 80 for IL-2 content assay with CTLL-2 cells. IL-2 production by the T cells cultured without stimulation was less than 0.32 unit/ml.

Inhibitory Effect of Wilforonide on Antigen-Induced T Cell Proliferation.

T cells were cultured with or without SK (1 ng/ml) or SK+IL-2 (50 u/ml) or SK+PMA (0.2 ng/ml) in the presence or absence of the following concentrations of wilforonide: 10 ng/ml, 50 ng/ml, 100 ng/ml, 500 ng/ml or 1,000 ng/ml. The cells were allowed to culture for five days. The cultures were pulsed with [$^3$H]-thymidine for the last 24 hours of culture. The data collected from this study is provided in Table 22. These data represent the mean of the percent inhibition of [$^3$H]-thymidine incorporation of five independent experiments. $ID_{50}$ were calculated based on the regression formula by using the fx-3600 calculator. T cells cultured with SK or SK+IL-2 or SK+PMA gave cpm of $1.87 \times 10^3$, $4.99 \times 10^3$ and $6.67 \times 10^3$, respectively.

The response to SK inhibited by low concentrations Wilforonide is shown to be partially overcome by adding IL2 or PMA, as demonstrated by the markedly higher (increased) $ID_{50}$. This indicates that inhibition correlates to a decrease in IL2 production. This decrease is overcome by adding IL2 or co-stimulating with PMA that induces IL-2 production.

The data from this study is provided in Table 22.

TABLE 22

INHIBITORY EFFECT OF WILFORONIDE ON ANTIGEN-INDUCED T CELL PROLIFERATION*

| Wilforonide (ng/ml) | SK | SK + IL-2 | SK + PMA |
|---|---|---|---|
| 10 | 42.15 | 19.59 | 22.67 |
| 50 | 44.47 | 12.37 | 17.70 |
| 100 | 49.14 | 14.52 | 20.32 |
| 500 | 75.20 | 61.70 | 53.30 |
| 1,000 | 84.23 | 86.21 | 65.43 |
| $ID_{50}$ (ng/ml) | 127.12 | 476.00 | 613.00 |

*T cells were cultured with or without SK (1 mg/ml) or SK plus IL-2 (50 u/ml) or SK plus PMA (.2 ng/ml) in the presence or absence of indicated concentrations of wilforonide for 5 days. Cultures were pulsed with [$^3$H]-thymidine for the last 24 hours. Data represent the mean of the % inhibition of [$^3$H]-thymidine incorporation of 5 independent experiments. $ID_{50}$ were calculated based on the regression formula by using the fx-3600 calculator. T cells cultured with SK or SK + IL-2 or SK + PMA gave cpm of $1.87 \times 10^3$, $4.99 \times 10^3$ and $6.67 \times 10^3$, respectively.

EXAMPLE 12

TwHF T2 Extract Inhibits Production of Interferon γ And Transcription of the IL-2 Gene The present example demonstrates that the T2 extract of *Tripterygium wilfordii* Hook F inhibits production of interferon γ and transcription of the IL-2 gene.

Transcription studies were carried out to determine whether the extract of TwHF directly affected IL-2 gene transcription or had post-transcriptional effects. Jurkat cells that had been stably transfected with a construct containing the IL-2 promoter driving transcription of the reporter gene, chloramphenicol acetyltransferase (CAT), were employed.
Methods IFN-γ assay. IFN-γ content in supernatants was determined with a radioimmunoassay kit as described by the manufacturer (Centocor, Malvern, Pa.). T cells ($1 \times 10^5$/ml) were incubated with PHA (1 μg/ml) for 24 h in the presence or absence of the EA extract. Cell-free supernatants were assayed for IL-2 and IFN-γ content.

IL-2 CAT assay. Jurkat cells were electroporated with a construct of the IL-2 promoter containing most of the T cell specific transcription factor binding sites within the promoter/enhancer (region −342 to +47 derived from IL-2/pJGFCA19 construct) driving the bacterial chloramphenicol acetyl transferase (CAT) gene inserted into a vector containing a neomycin selection marker, designated IL-2/PML3 (72,73). The cells were selected with geniticin (0.5 mg/ml) for approximately one month before use. The cells were then incubated with PHA and PMA, in the presence of varying concentrations of an extract of TwHF (a chloroform/methanol extract from the woody portion of the roots of TwHF, dissolved in DMSO and diluted with culture medium) or in medium alone for 20 h. After incubation, the supernatants were collected for assay of secreted IL-2 and equivalent numbers of cells were washed and lysed by repeated freeze/thaw in 100 μl of 0.25M Tris-HCl (pH 7.8) and centrifuged for 5 minutes at high speed to remove cellular debris. CAT activity was measured by the addition of 1 μCi [$^{14}$C]-chloramphenicol (60 mCi/mmol; New England Nuclear, Boston, Mass.) and 14 μl of 5 mM acetyl coenzyme A to the lysates followed by a 12 h incubation at 37° C. as previously described by Gorman et al.(74). The reaction was stopped by the addition of 1 ml cold ethyl acetate and after phase separation, the organic phase was evaporated, resuspended in 20 μl of ethyl acetate and spotted onto silica gel thin layer chromatography plates. The chromatograms were visualized and the radioactivity quantified using an automated β-detection and imaging device (AMBIS). The percent conversion was calculated by dividing the cpm of the acetylated chloramphenicol by the total chloramphenicol present in each sample. CAT activity was found to correlate with levels of secreted IL-2 when these cells were stimulated with various mitogens. Jurkat cells transfected with PML-LDLr-6500 were taken as a positive control for CAT activity[75].
Results Inhibition of mitogen-induced IL-2 gene transcription by extracts of TwHF. The data of Table 23 show that the extract of TwHF inhibited mitogen-induced CAT activity in a dose-dependent manner, similar to that observed for IL-2 production.

TABLE 23

Inhibition of IL-2 Transcription by a T2 Extract[1]

|  | % Acetylation | IL-2 Production (Units/ml) |
|---|---|---|
| Control | 0.17 | 23.4 |
| PHA + PMA | 6.90 | 5440 |
| PHA + PMA + T2 1 µg | 0.22 | 0 |
| PHA + PMA + T2 5 µg | 0.22 | 0 |
| PHA + PMA + T2 10 µg | 0.19 | 0 |
| 4JK cells | 95.80 | — |

[1]Jurkat T cells stably transfected with an IL-2 promoter/CAT construct, were incubated with or without PHA (2 µg/ml) in the presence or absence of varying concentrations of an extract of TwHF for 18 h. Supernatants were collected for IL-2 assay with CTLL-2 cells. Cellular extracts were assessed for CAT activity as described in the methods. CAT activity of a control cell line transfected with a CAT construct driven by a constitutively active promoter (4JK cells) is shown as a positive control for the assay.

These results indicate that the extract of TwHF inhibits transcription of the IL-2 gene.

Inhibition of IFN-$_7$ production. As shown in FIG. 34, the EA extract inhibited PHA-induced IL-2 production ($EC_{50}$= 0.75±0.12 µg/ml). PHA-induced IFN-$\gamma$ production was also very sensitive to EA-mediated inhibition ($EC_{50}$=0.64±0.04 µg/ml).

EXAMPLE 13

Glucocorticoid Receptor Binding of Components of *Tripterygium wilfordii* Hook F (TwHF)

The present example provides data on the capacity of the TwHF extract and purified TwHF components to bind to the glucocorticoid receptor (GR). Binding of the TwHF extract and components thereof to the GR was demonstrated by competitive inhibition of binding of the natural GR ligand using several model systems. The ability of TwHF to compete with [$^3$H] dexamethasone for binding to the glucocorticoid receptor, the ability of TwHF to inhibit glucocorticoid receptor-mediated activation of a responsive target gene construct in transfected mammalian cells, and the capacity of TwHF to inhibit growth of a transfected cell line expressing a glucocorticoid receptor regulating the SV40 large T antigen, and therefore, whose growth is dependent on dexamethasone, were examined.

Chloroform-methanol extracts of TwHF were used in this example; the activity of these extracts is correlated to the activity of the ethyl acetate extracts by the amount of triptolide in the preparations. The amount of triptolide was measured by HPLC as described in Example 15.

Methods

Whole cell glucocorticoid binding assay. Human skin fibroblasts were cultured in MEM-10% bovine calf serum in an atmosphere of 5% $CO_2$ at 37° C. Cells were plated in 7 cm wells at 750,000 cells per well. Twenty-four hours before experiments, the medium was changed to MEM with 5 mg/ml bovine serum albumin. On the day of the experiment, the medium was replaced with 3.0 ml of MEM per well with 10 nM [3h] dexamethasone. Varying amounts of the extract of TwHF were added to some wells. The cells were incubated at 37° C. for 60 minutes, then washed, harvested by trypsinization, and lysed in 1 ml water. Aliquots were assayed for protein and counted for bound radioactivity. These cells express, on average, about 170 fmol of glucocorticoid receptor per mg protein.

Cell transfections and assays of GR mediated gene activation. COS-7 cells were maintained in culture in DMEM-10% bovine calf serum. These cells do not express endogenous steroid hormone receptors. Cells were plated at $10^6$ cells per 10 cm plate. Twenty-four hours later, the cells were transfected with 500 ng pRShGrα, a GR expression vector (obtained from the Salk Institute, La Jolla, Calif.) and 10 µg of pMMTV-luciferase, a synthetic reporter gene. However, other expression vectors and synthetic reporter genes available to those of skill in the art may be used for transfection. The vector pMMTV-luciferase contains the luciferase gene under regulatory control of glucocorticoid-inducible elements in the MMTV-long terminal repeat. Cells were transfected using the calcium-phosphate precipitation technique (mammalian transfection kit, Stratagene, La Jolla, Calif.). After transfection, dexamethasone, (1 µM) was added to the medium. Twenty-four hours later, the cells were washed, harvested, and lysates prepared by three cycles of freeze/thawing. The lysates were cleared by centrifugation at 12,000× g for 5 minutes; aliquots were assayed for protein content and equal amounts of proteins were used for luciferase assays.

An additional assay system that was employed involved IDH4 cells, whose growth is dependent on the presence of dexamethasone. IDH4 cells, that express endogenous glucocorticoid receptors, were produced by transfecting human fibroblasts with a plasmid containing the MMTV-long terminal repeat driving the SV40 large T antigen. Since extended growth of these cells is dependent on expression of the large T antigen, these cells require exogenous glucocorticoid to maintain proliferation.

Results

Figure 22:
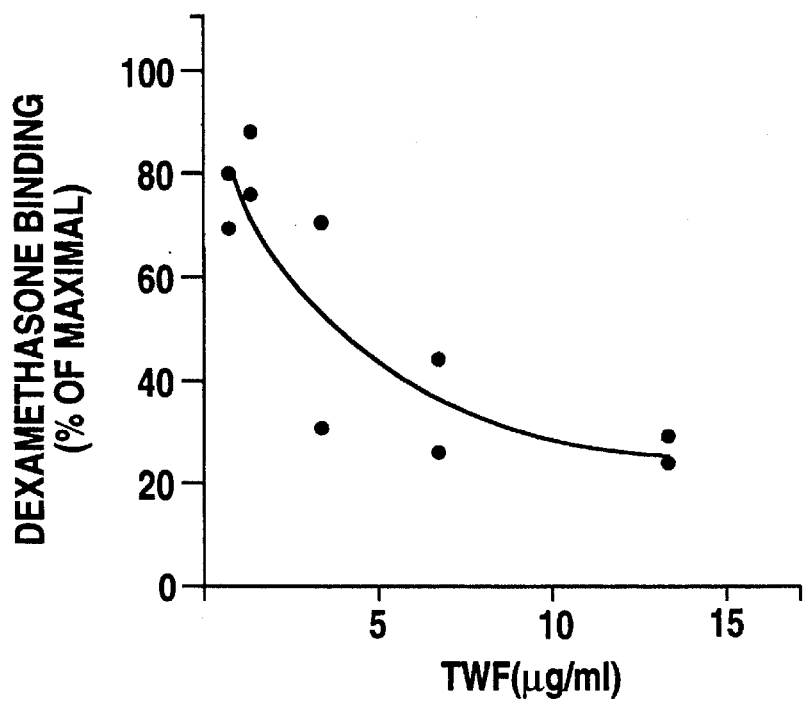
FIG. 22. TwHF inhibits binding of dexamethasone to human skin fibroblast glucocorticoid receptor (GR).

TwHF extract binds GR. The chloroform-methanol extract of TwHF inhibited binding of [$^3$H]dexamethasone to the GR endogenously expressed in human skin fibroblasts (FIG. 22). Intact monolayers of human genital skin fibroblasts (about 170 fmol GR per mg protein) were incubated with 10 nM [$^3$H] dexamethasone alone or with an increasing concentration of TwHF. No estimate of the relative binding affinities of TwHF and dexamethasone is possible, however, since the TwHF extract is a mixture of compounds. Inhibition of 50% of GR activity occurred with the addition of approximately 5 µg of the extract. Addition of pure ethanol, the solvent for the TwHF extract, in equal volumes had no effect on GR ligand binding activity. Moreover, the TwHF extract had no effects on binding of dihydrotestosterone to genital skin fibroblasts, indicating that it did not inhibit androgen receptor activity, implying a specific effect on GR.

Figure 23:
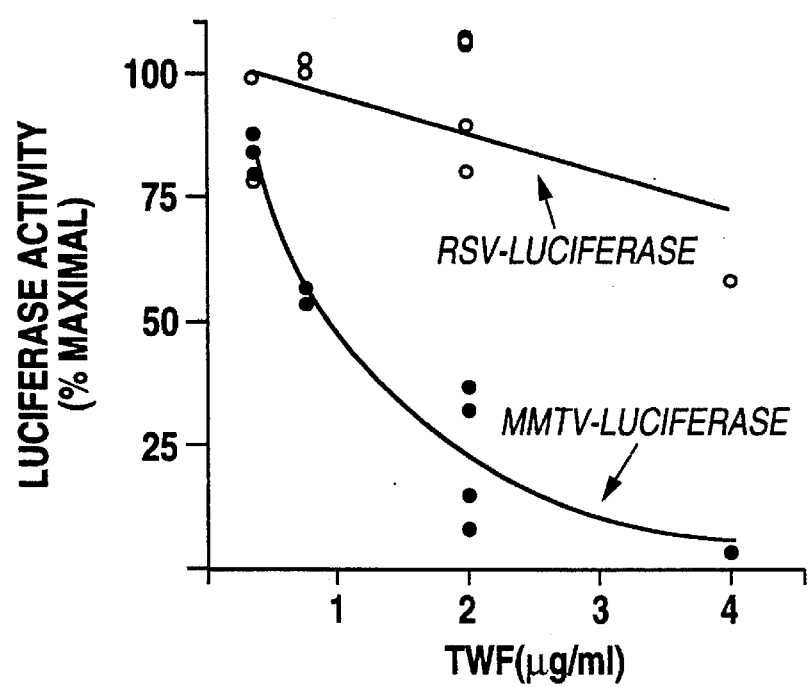
FIG. 23. TwHF inhibits GR-mediated target gene activation. The target gene was the luciferase gene under regulatory control of glucocorticoid-inducible elements in the MMTV long terminal repeat.

TwHF extract inhibits dexamethasone-induced activation of target gene transcription but lacks intrinsic GR agonist activity. The chloroform-methanol extract of TwHF also inhibited GR-mediated activation of a synthetic target gene (FIG. 23). COS-7 cells were transfected with a human GR expression vector and the MMTV-luciferase reporter gene construct. A parallel set of plates was transfected with the constitutively active RSV-luciferase construct. After 24 hours, dexamethasone was added at a concentration of 10 nM alone or in combination with increasing concentrations of TwHF. Cells were lysed after 24 hours and assayed for luciferase activity. In the absence of TwHF, background levels of luciferase activity were about 1% of dexamethasone-induced activity. Addition of dexamethasone resulted in, on average, a 100- to 200-fold induction of luciferase activity. Addition of the TwHF extract in concentrations shown to compete for GR binding inhibited target gene activation (FIG. 23). Luciferase expression under control of a constitutively active promoter, i.e., a promoter not responsive to glucocorticoid receptor, (RSV-luciferase) was not inhibited by the addition of TwHF (FIG. 23) indicating specificity of TwHF extract for GR dependent processes.

To determine whether TwHF had direct glucocorticoid agonist activity, COS-7 cells transfected with a human GR expression vector and the MMTV reporter construct were stimulated with TwHF, but without dexamethasone. TWF caused no direct target gene activation (Table 24). By contrast, dexamethasone induced dramatic reporter gene transcription.

TABLE 24

| | TWF Lacks Intrinsic GR Agonist Activity | | | | |
|---|---|---|---|---|---|
| | Control | TWF 0.4 μg/ml | TWF 0.8 μg/ml | TWF 2.0 μg/ml | TWF 4.0 μg/ml | DEX 10 nM |
| RLU #1 | 998 | 1260 | 1603 | 1167 | 903 | 193,419 |
| RLU #2 | 2850 | 2012 | 1905 | 1106 | 517 | 218,786 |

COS-7 cells were transfected with human GR expression vector and the MMTV-luciferase reporter gene construction. After 24 hours TWF at concentrations known to compete for GR binding (0.4–4.0 μg/ml) were added. Cells were lysed after 24 hours and extracts assayed for luciferase activity. Controls included no addition (negative control) and 10 nM dexamethasone (positive control). Data shown are relative light units (luciferase activity) for duplicate transfections in a single experiment.

Similar experiments in L929 cells, and in both COS and L929 cells stimulated with cAMP (known to "unmask" agonist activity of some GR competitors) confirmed this lack of agonist function of TwHF.

Figure 24:
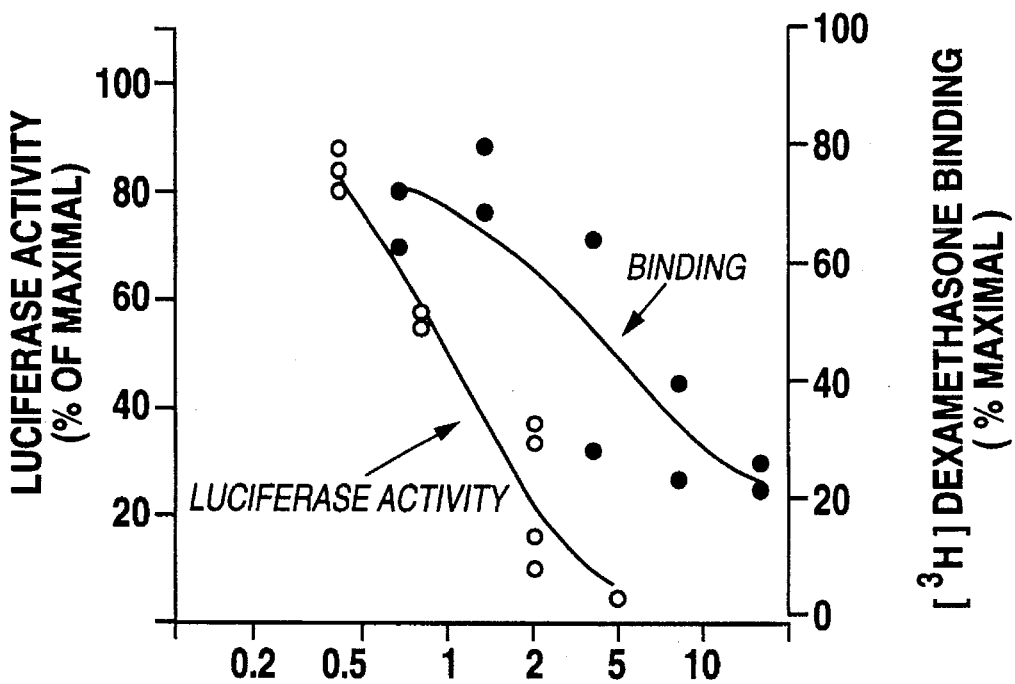
FIG. 24. Dose response curves of the effect on GR ligand binding and target gene activation data of FIG. 20 and 21 are replotted together as % maximal binding or activity as a function of log TwHF concentration.

To compare the concentration response curves for TwHF-mediated inhibition of GR ligand binding activity and TwHF inhibition of GR-mediated target gene activation, the data of FIG. 22 and 23 were combined. Whereas the curves are comparable, TwHF appears several-fold more potent for inhibition of target gene activation compared to ligand binding inhibition (FIG. 24).

Figure 25A:
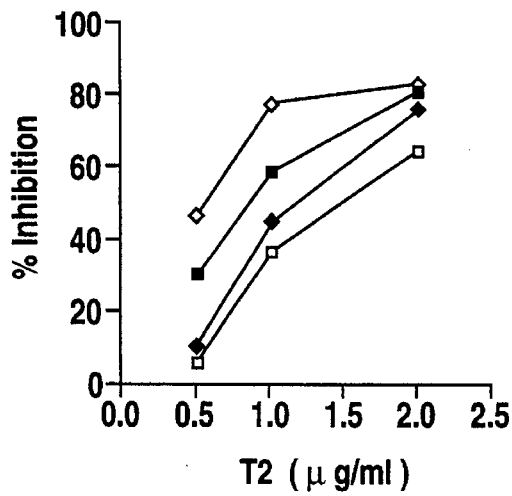
FIG. 25A, FIG. 25B and FIG. 25C. The extract of TwHF and purified components inhibit dexamethasone dependent growth of IDH4 cells in a concentration dependent manner. IDH4 cell proliferation was assessed by $^3$H-thymidine incorporation after a 72 hour culture. (The n in $10^n$ is the abscissa of the graph, i.e., 1, 2, 3, 4, or 5; indicating nanomolar concentration).
Figure 25B:
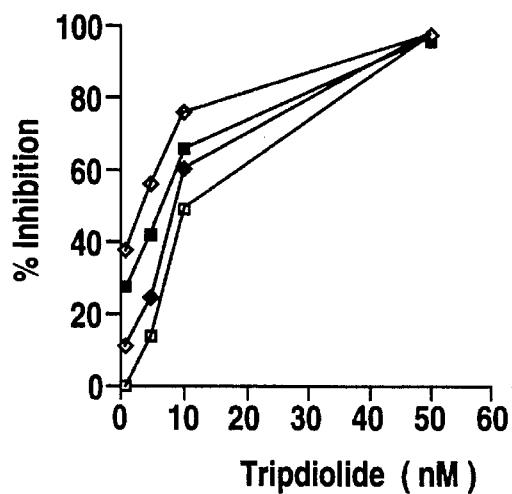
Figure 25C:
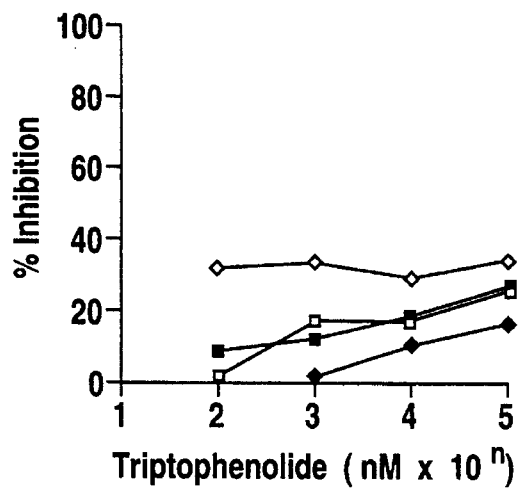

The extract of TwHF and the purified component tripdiolide inhibited dexamethasone dependent growth of IDH4 cells in a concentration dependent manner (FIG. 25A, 25B and 25C). Tryptophenolide was less active and its activity was not generally correlated with dosage. IDH4 cells ($1 \times 10^6$/ml) were cultured for 72 hours in DMEM supplemented with 10% of dexamethasone-free bovine serum with or without dexamethasone in the presence or absence of T2 or tripdiolide or triptophenolide, as indicated. [$^3$H]-Thymidine was present for the last 16 h. Data represent the mean % inhibition of [$^3$H]-thymidine incorporation of three replicate determinations of three separate experiments. IDH4 cells incubated without stimulation gave 16,391 cpm. Cells cultured with dexamethasone at 1 nM, 10 nM, 100 nM and 1,000 nM gave 35,554, 52,937, 105,357 and 96,677 cpm, respectively.

Further studies assessed whether cortisol-like immunoreactivity was contained in TwHF extract. With most anti-cortisol antibodies tested, no evidence for the presence of such molecules in TwHF was found. This was confirmed by fractionation experiments on Sephadex LH-20 in which the glucocorticoid receptor blocking capacity of TwHF was found to exist in fractions distinct from the elution position of authentic cortisol. With a single anti-cortisol antibody directed against the A ring of the steroid, some cortisol-like immunoreactivity was detected (FIG. 26). These data suggest that some components of TwHF could have cortisol-like structural features, but no authentic cortisol was found.

Purified TwHF compounds were similarly tested for effects on ligand binding to GR, and for inhibition of GR-mediated target gene activation. Both triptolide (compound A) and tripdiolide (compound B) inhibited target gene activation by GR, whereas triptophenolide (compound C) was far less potent. Of importance, triptophenolide is much less immunosuppressive than triptolide or tripdiolide. Binding inhibition and target gene activation curves are shown for compound A (FIG. 27). Again, the compound was more potent at inhibition of MMTV-luciferase induction by more than an order of magnitude. None of the purified TwHF components showed cortisol immunoreactivity (FIG. 28.)

EXAMPLE 14

Anti-Inflammatory Properties of TwHF Extract

In the present example, the extract of TwHF and tripdiolide were examined for their ability to inhibit the in vivo induction of a pro-inflammatory enzyme activity, namely the stimulation of the inducible form of cyclooxygenase (COX-2). Cyclooxygenase-1 is the enzyme responsible for the constitutive synthesis of prostaglandins and certain related autocoids, mediators of inflammation. Inhibition of this enzyme causes the side effects of NSAIDS. During inflammation and after stimulation, inflammatory cells, such as macrophages, produce a new enzyme, cyclooxygenase-2, that is responsible for much of the prostaglandin production at inflammatory sites.

Monocytes ($1 \times 10^6$/ml), separated from normal human PBMCs, were incubated in RPMI-1640 medium supplemented with 5% normal human serum with or without LPS (10 μg/ml) and in the presence or absence of one of the following reagents: T2, tripdiolide, dexamethasone, or RU486, at the indicated concentrations (FIG. 29A–29D). After 18 hours of incubation, cell-free supernatants were collected and assayed for PGE2 content with a radioimmunoassay kit (Amersham), as described by the manufacturer. Data represent the mean of two replicate determinations of two separate experiments. Monocytes cultured without LPS produced 392 pg PGE2/0.2 million cells. Human monocytes produce prostaglandinE$_2$ (PGE$_2$) when stimulated with bacterial endotoxin. This relates to the induction of cyclooxygenase 2 (COX-2) and is inhibited by dexamethasone (FIG. 29A–29D). Similarly, the production of PGE$_2$ is inhibited by the extract of TwHF and its purified immunosuppressive component, tripdiolide. Constitutive PGE$_2$ production by unstimulated monocytes that is mediated by cyclooxygenase-1 was not inhibited by TwHF or its components. Specificity is shown in that previous studies had documented that the extract of TwHF did not inhibit other functions of monocytes, such as antigen presentation.

In summary, the data are consistent with the conclusion that components of TwHF specifically interact with the glucocorticoid receptor and exert anti-inflammatory and immunosuppressive effects by this mechanism, and have no direct agonist activity on glucocorticoid responsive genes.

These data further demonstrate that the T2 extract, and components thereof, bind the glucocorticoid receptor, and the bound complex fails to activate glucocorticoid receptor-sensitive promoter regions. Genes that require those promoters to be active, therefore, are not induced. Concomitantly, T2 inhibits inflammatory processes as demonstrated herein by the inhibition of induction of cyclooxygenase-2 and also by the inhibition of IL-2 and interferon γ gene activation. The combined effect of anti-inflammatory property without induction of steroidal-related agonist activity provides a heretofore unknown and long-sought treatment method for inflammation, autoimmune disease and other immunosuppressive conditions where the undesirable effects of steroids (TwHF has no agonist activity) and non-steroidal anti-inflammatory drugs (e.g., aspirin) can be avoided (cyclooxygenase-1 is not inhibited by TwHF).

EXAMPLE 15

HPLC Determination of Triptolide and Tripdiolide In An Ethyl Acetate Extract of TwHF A new analytical method for the determination of triptolide and tripdiolide in ethyl acetate extracts of *Tripterygium wilfordii* Hook F. is described in the present example. The procedure consists of preliminary enrichment of the triptolide and tripdiolide by Sep-Pak alumina B cartridge chromatography followed by HPLC analysis. HPLC is performed with a stainless steel column packed with Nova-Pack C18, using acetonitrile-water (19:81) as a mobile phase for triptolide and acetonitrile-water (11:89) for tripdiolide. The effluent is monitored by ultraviolet detection at 214 nm. Quantitative analysis of triptolide is then carried out by comparison to an internal standard, and of tripdiolide by the external standard method. The amounts of triptolide and tripdiolide per 100 mg of the ethyl acetate extract were determined to be 19.88 µg and 9.58 µg respectively. The method is sufficiently sensitive and specific to assay the diterpenes found in *Tripterygium wilfordii* Hook F. accurately.

Methods

Instruments. The Waters (Milford, Mass.) liquid chromatograph employed was configured with two Model 510 pumps, a Model U6K injector and Model 441 UV detector set up at 214 nm. The data was processed with Millennium software, Version 1.10 (Waters Assoc.). The stainless steel column (150 mm×3.9 mm I.D.) was packed with Nova-Pak C18 particle size 4 µm (Water Assoc.). An HPLC precolumn, with an insert packed with Nova-Pak C18, (Water Assoc.) was used to extend the column life. The model ULTRAsonik 2QT/H ultrasonic water bath used in the solvent degassing and sample preparation was purchased from NEY Barkmeyer Division (Yucaipa, Calif.).

Chemicals and reagents. Triptolide and tripdiolide were prepared from the ethyl acetate extract of TwHF by silica gel column chromatography successively with chloroform, chloroform-ether and chloroform-ethyl acetate as the eluents. The fractions containing triptolide and tripdiolide were purified on preparative HPLC with a Nova-Pack C18 column, 25×100 mm, using acetonitrile-water as the mobile phase. The compounds were recrystallized from n-hexane-dichloromethane. Triptolide was identified by UV, IR, proton NMR and mass spectrums. Tripdiolide was identified by HPLC, TLC and proton NMR and comparison with the known laboratory product provided by Boehringer Ingelheim Pharmaceuticals Inc. (Ridgefield, Conn.). Acetonitrile was HPLC grade purchased from Aldrich Chemical Co. (Milwaukee, Wis.), water was Millipore pure, and other solvents were GR grade. The mobile phases were degassed by vacuum in conjunction with sonication just before use. The Sep-Pak Plus alumina B cartridge was purchased from Waters Assoc. (Milford, Mass.); acetophenone, selected as an internal standard for the triptolide assessment, was purchased from Sigma Chemical Co. (St. Louis, Mo.). The chemical structures of triptolide and tripdiolide are shown in FIG. 11.

Preparation of the ethyl acetate extract of TwHF. The roots of TwHF were collected from Fujian province, China. The skin was removed from the roots and the woody portion of the roots was ground to coarse powder. 1000 g of the coarse powder was extracted with ethanol three times. The ethanol solutions were combined and evaporated under reduced pressure. The residue was then extracted with ethyl acetate. Concentration of the solution under reduced pressure yielded 22 g of the ethyl acetate extract.

Enrichment procedure. About 50 mg of the ethyl acetate extract was weighed accurately and dissolved in 10 ml of chloroform in an ultrasonic bath for 25 minutes. The extract solution was filtered and the residue was washed with 10 ml of chloroform-ethyl acetate (9:1). The washings combined with the original chloroform solution were applied to the Sep-Pak cartridge. 25 ml of chloroform-ethyl acetate (9:1) and 15 ml of ethyl acetate-methanol (9:1) were successively passed through the cartridge. The chloroform-ethyl acetate fraction, used for the determination of triptolide, was evaporated to dryness under a gentle stream of nitrogen. The residue was dissolved with 1.00 ml of acetophenone solution, that was prepared by dissolving acetophenone in methanol to obtain a solution having a concentration of 12.5 µg per ml. The dissolved residue was diluted with acetonitrile-water (19:81) to 2.00 ml. The ethyl acetate-methanol fraction was evaporated. The residue was dissolved in 1.00 ml of acetonitrile-water (11:89) solution and used to analyze for tripdiolide content.

Determination of diterpenes. A 10 µl volume of each purified sample solution was injected into the liquid chromatograph. The mobile phase for each separation is listed with the individual chromatogram. Triptolide was determined by comparison to an internal standard. The reference solutions containing 1.83, 3.66, 7.32, 16.08 and 36.18 ng µl$^{-1}$ of triptolide and 6.25 ng µl$^{-1}$ of acetophenone for each solution were prepared in acetonitrile-water (19:81). The reference solutions of tripdiolide were prepared in acetonitrile-water (11:89) at the concentrations of 1.28, 2.55, 5.10, 10.20, 20.40, 30.60, and 40.80 ng µl$^{-1}$. Two replicates of each were injected into the HPLC system. The resulting chromatograms yielded data for the standard curves. The contents of triptolide and tripdiolide were calculated and expressed per 100 mg of the dried extract (drying at 80° C. to a constant weight.

Results

The enrichment procedure and chromatographic separation as well as the selection of an internal standard are three major problems in HPLC analysis of crude plant extracts. Many enrichment procedures were investigated during the preliminary phases of this study. These included different absorbents, such as silica gel, alumina N, florisil, diol, aminopropyl $NH_2$, cyanopropyl CN, activated carbon and polyamide. In addition, different solvent systems were tested. Sep-Pack Plus alumina B cartridge was found to be an efficient and convenient purifying method that involved the minimum number of steps. HPLC was performed with a Nova-Pack C18 column using acetonitrile-water as a mobile phase system. This resulted in a better separation of triptolide, tripdiolide and acetophenone from other components of the plant than did the use of methanol-water as a mobile phase. A detective wavelength of 214 nm was employed because of the α, β-unsaturated lactone ring in the diterpene structures. Acetophenone was found to be the most suitable internal standard for the determination of triptolide. Because of interference from other components, attempts to use an internal standard in the determination of tripdiolide were unsuccessful. FIG. 30 illustrates the chromatogram of triptolide and acetophenone. The retention times of the two compounds were 11.35 min. and 8.15 min. respectively. FIG. 31 shows the chromatogram of tripdiolide. The retention time was 10.3 min.

The separation of triptolide, acetophenone and tripdiolide from the extracts of TwHF by HPLC was achieved using the method described above. This approach provided a good quantitative and reproducible recovery. FIG. 32 depicts a typical chromatogram of the extract for the determination of triptolide after addition of acetophenone. It is apparent that the other components present in the extract did not alter the internal standard peak. FIG. 33 shows a typical chromatogram of the extract for the determination of tripdiolide.

The peak purity was tested by collecting the fractions corresponding to both of the compounds and analyzing them by HPLC on the same column using methanol-water (30:70) as a mobile phase and adjusting the flow rate to 1.0 mL per min. The results indicated that a single component with the retention times corresponding to triptolide (5.1 min.) or tripdiolide (16.7 min.) had been isolated.

A linear calibration graph for triptolide was obtained by plotting the ratio of the peak area of triptolide to the internal standard (y) versus the amount of triptolide (x, ng). The regression equation and correlation coefficient (r) were y=0.025x–0,049, r=0.99999, n=5. The linear calibration graph of tripdiolide was obtained by plotting the peak area response of tripdiolide (y) versus the amount of tripdiolide (x, ng). The regression equation and correlation coefficient were y=744.2x–2123, r=0.9998, n=7. The range of the calibration curve was from about 18.3 ng to about 361.8 ng for triptolide and from about 12.8 ng to about 408.0 ng for tripdiolide.

The detection limit was determined at very low concentrations using the described method. The detectable amounts of triptolide and tripdiolide were about 4.77±0.66 ng (n=4) and about 9.05±0.66 ng (n=3) respectively.

The recovery test was carried out by adding pure triptolide and tripdiolide to the extract and assaying with the same procedure described above. The recoveries (mean % ±SD) of triptolide was about 98.34±1.54 (n=4) and tripdiolide was about 95.85±1.49 (n=4).

The assay results are displayed in Table 25. Each term is the mean of two injections. The contents of triptolide and tripdiolide in about 100 mg of the ethyl acetate extract of TwHF were about 19.88 and about 9.58 μg respectively.

TABLE 25

CONTENTS OF TRIPTOLIDE AND TRIPDIOLIDE IN THE EXTRACT OF TRIPTERYGIUM WILFORDII HOOK F. DETERMINED BY HPLC[1]

| Diterpenes | Amount in individual Determinations (μg per 100 mg of extract) | | | | Mean ± SD | Relative Standard Deviation (%) |
|---|---|---|---|---|---|---|
| Triptolide | 18.45 | 20.90 | 21.05 | 18.95 | 19.88 ± 1.04 n = 6 | 0.052 |
|  | 19.82 | 20.12 |  |  |  |  |
| Tripdiolide | 10.30 | 10.03 | 10.17 | 9.64 | 9.58 ± 0.54 n = 15 | 0.056 |
|  | 9.72 | 10.14 | 10.14 | 9.51 |  |  |
|  | 9.12 | 8.75 | 8.98 | 9.01 |  |  |
|  | 8.98 | 9.11 | 10.06 |  |  |  |

[1]The values from individual experiments are the amounts per 100 mg of dry ethyl acetate extract.

In summary, this example provides an accurate, sensitive and reliable method for the determination of triptolide and tripdiolide in an extract of TwHF. The pretreatment of samples with the Sep-Pak alumina B cartridge before HPLC represents a fast, simple and effective enrichment procedure with a very satisfactory recovery of the compounds. The successful employment of the internal standard greatly improved the accuracy and reproducibility for the triptolide assay. Triptolide and tripdiolide are two of the major diterpene compounds contained in TwHF. This study provides the first quantitative data about the tripdiolide content in TwHF. Combined with the capacity to analyze triptolide, the approach makes it possible to evaluate the efficacy and toxicity of the TwHF extract and control the quality and safety of the preparation of this material for clinical trials and animal experiments.

EXAMPLE 16

TwHF Extract Interferes With Progesterone Metabolism

Figure 29A:
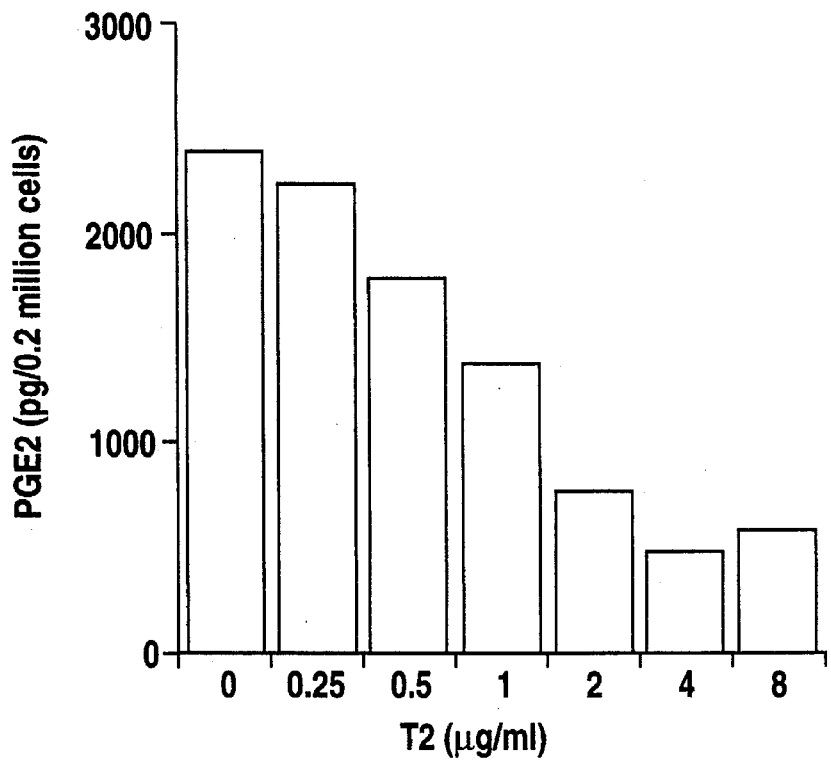
Figure 29B:
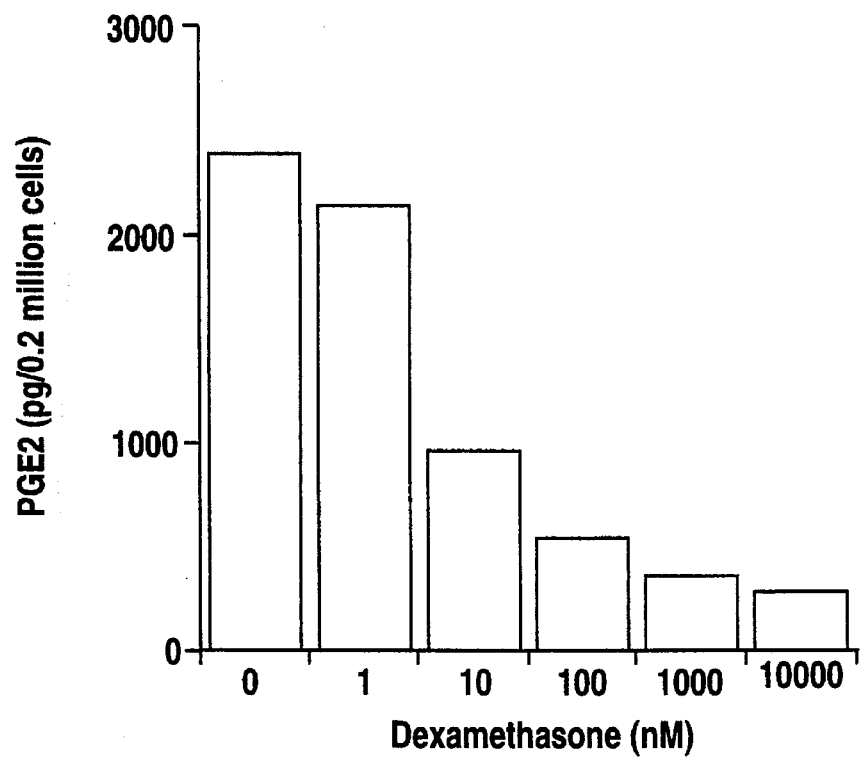
Figure 29C:
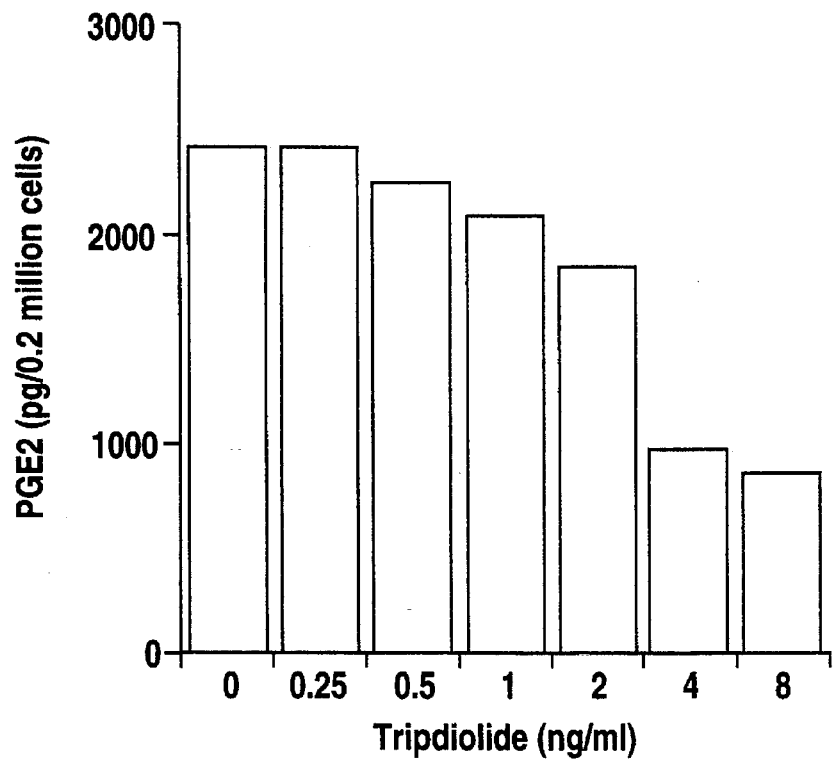
Figure 29D:
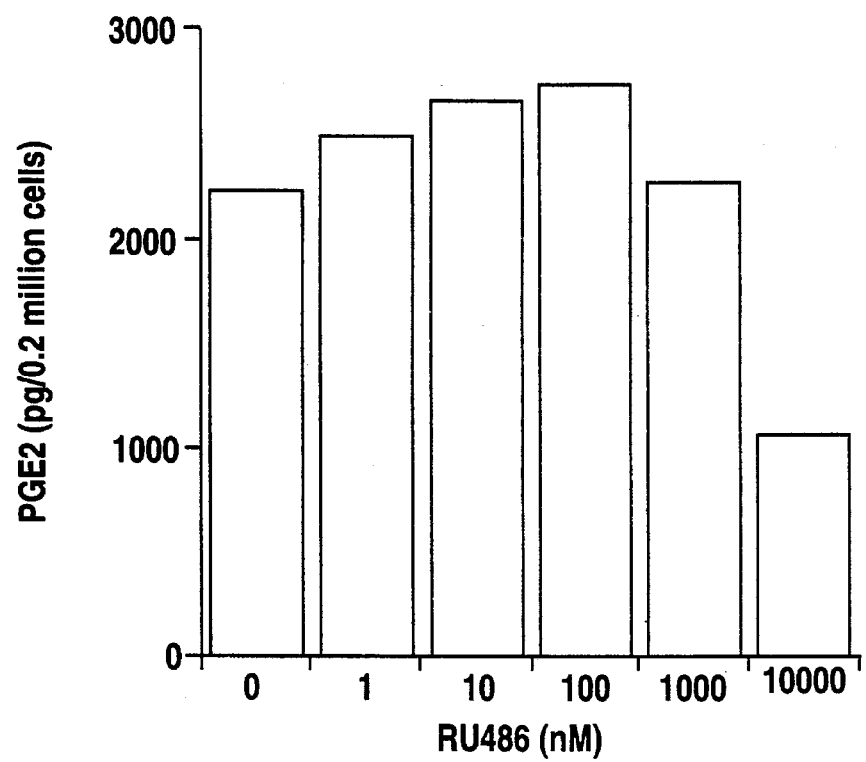

The present prophetic example describes a property of the TwHF extract in interfering with progesterone metabolism. It is expected that the extract or components thereof may bind the progesterone receptor as many compounds that bind to the glucocorticoid receptor also bind to the progesterone receptor and therefore be used as a means of birth control or as a means of interrupting a pregnancy. As shown in FIG. 29D, RU486 inhibits endotoxin-induced $PGE_2$ production by human peripheral blood monocytes, however, it is not as effective as the TwHF extract at lower concentrations. The use of TwHF preparations in humans is provided in Example 9.

EXAMPLE 17

Therapeutic Preparations of the TwHF Extract

The present example details convenient preparations of the extracts, such as pills, tablets, capsules, and the like that may be prepared and used in the various aspects of the invention.

The TwHF extract, or purified components thereof, may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the extract, or components thereof, may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is about 30–120 mg, preferably about 60 mg, such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the extract, or components thereof, may be incorporated into sustained-release preparation and formulations.

The extract, or components thereof, related to triptolide, tripdiolide, or wilforonide selected by the biological and molecular activities described herein may also be administered parenterally or intraperitoneally. Solutions of the purified active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the extract, or components thereof, in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

EXAMPLE 18

Methods For Screening For Agents Having GR Binding Activity And A Steroid-Sparing Effect The present example provides assays for screening candidate substances for glucocorticoid receptor binding activity while being inactive for induction of steroid responsive genes. Since TwHF, and components thereof, are demonstrated for the first time in the present disclosure to bind the receptor even in the presence of dexamethasone; an assay for identifying other glucocorticoid receptor binding substances has been identified using TwHF, or a receptor-active fraction/component thereof. By way of example, a candidate substance is incubated with the glucocorticoid receptor in the presence of TwHF, or a receptor-binding component thereof, and substances competing with TwHF, or a component thereof, for the receptor would be selected. It is contemplated that this screening technique will prove useful in the general identification of a compound or mixture of compounds that has binding activity for the glucocorticoid receptor. In other embodiments of the method, the candidate substance will be further screened to determine if it is capable of inhibiting the activation of steroid dependent genes, using the TwHF as a standard.

Another embodiment of the present invention is a method for determining the ability of a candidate substance to bind the glucocorticoid receptor in, for example, a competitive binding assay in the presence of TwHF preparation, or pharmacologically active glucocorticoid receptor binding components thereof. For example, the method, in some embodiments, includes generally the steps of obtaining a glucocorticoid receptor preparation, admixing a candidate substance with the glucocorticoid receptor preparation in the presence of TwHF preparation or a pharmacologically active component thereof that binds glucocorticoid receptor, and determining the ability of the candidate substance to bind the glucocorticoid receptor in the presence of the TwHF, or pharmacologically active component thereof.

Naturally, one would measure or determine the binding of the TwHF composition or component of the composition, in the absence of the added candidate substance in a separate control study. One would then add the candidate substance and the TwHF preparation together to a receptor preparation and determine the ability of the candidate substance to compete with the TwHF for binding the receptor. A candidate substance which reduces the binding of TwHF preparation to the receptor relative to the binding in its absence is indicative of a candidate substance with glucocorticoid receptor binding capability.

Accordingly, in screening assays to identify pharmaceutical agents that bind the glucocorticoid receptor, it is proposed that compounds isolated from natural sources such as plants, animals or even sources such as marine, forest or soil samples, may be assayed for the presence of potentially useful pharmaceutical agents. It will be understood that the pharmaceutical agents to be screened could also be derived from chemical compositions or man-made compounds. The active compounds may include fragments or parts of naturally-occurring compounds or may be only found as active combinations of known compounds which are otherwise inactive.

Any method may generally be employed to determine glucocorticoid receptor binding. For example, by using the methods of Example 15 to determine the amount of unbound triptolide or tripdiolide present in a supernatant fraction of the above assay, it would be possible to determine the amount of binding by the candidate substance. A control sample would include a mixture where only TwHF was present.

Further methods will be those in which the glucocorticoid receptor incorporates or is conjugated to a label, such as an enzymatic, chemical or radiolabel, or incorporates one of the ligands of a two ligand-based detection system such as the avidin/biotin system. For ease and safety, the use of enzymatic labels, such as, for example, horseradish peroxidase, urease or alkaline phosphatase is preferred. In such cases, a colorimetric indicator substrate would be employed to provide a means detectable by the human eye or by a spectrophotometer.

One of skill in this art upon reading the present disclosure will realize that a candidate substance that is able to bind the glucocorticoid receptor in the presence of TwHF or at least one component thereof possessing pharmacological activity for binding glucocorticoid receptor, may activate steroid responsive genes or may inhibit the activation of steroid responsive genes. An assay using a reporter gene under the control of glucocorticoid receptor regulatory regions as used in Example 13 would determine whether steroid responsive genes are activated, and also serve to provide a method for further selection among candidate substances for those which do not activate steroid responsive genes.

An example of a glucocorticoid receptor preparation is a human skin fibroblast preparation. An example of GR regulatory region is the GR inducible elements of the MMTV long terminal repeat. An example of a reporter gene is the luciferase gene, or the CAT gene (chloramphenicol acetyltransferase).

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

REFERENCES

The following references, to the extent that they provide exemplary procedural or other details supplementary to those set forth herein, are specifically incorporated herein by reference.

1. Kirkman et al. (1989) "Response to monoclonal CD7 antibody in rheumatoid arthritis" Lancet 1:589.
2. Caperton et al. (1989) "Treatment of refractory rheumatoid arthritis (RA) with anti-lymphocyte immunotoxin" *Arthritis Rheum.* 24:2130.
3. Herog et al. (1989) "Anti-CD4 antibody treatment of patients with rheumatoid arthritis: I. Effect on clinical course and circulating T cells" *J. Autoimmunity* 2:627.
4. Kyle et al. (1989) "Beneficial effect of monoclonal antibody to interleukin 2 receptor on activated T cells in Rheumatoid arthritis" *Ann. Rheum. Dis.* 48:428.
5. Jia Li (1985) "Chemistry and pharmacology and clinical application of plants of Tripterygium family" Yao Xue Tong Bao 20:101.
6. Hubei Study Group (1982) "Pharmacological study on the ethanol extract of *Tripterygium wilfordii* Hook F" Zung Cao Yao 13:27.
7. Wei et al. (1988) "Side effects of $T_2$ in the treatment of 106 patients with glomerular diseases" *New Drug and It's Clinical Application* 1(6):37.
8. Jiang et al. (1987) "*Tripterygium wilfordii* Hook caused acute toxicity with kidney involvement in 17 cases" *Chinese J. Kidney Dis* 3 (3):167.
9. Chen et al. (1987) Clinical analysis of 10 cases of *Tripterygium wilfordii* Hook caused toxicity Symposium, "Clinical Application of *Tripterygium wilfordii* Hook", Hubei, China.
10. Tao et al. (1987) "Prospective, controlled, double-blind, cross-over trial of $T_2$ (polyglycosides extracted from *Tripterygium wilfordii* Hook F) in the treatment of rheumatoid arthritis" *Chinese J. Int. Med.* 26:399.
11. Tao et al. (1988) "Mechanism of treatment of rheumatoid arthritis with *Tripterygium wilfordii* Hook FI. Effect of $T_2$ on secretion of total IgM and IgM-RF by PBMC" *Acta. Acad. Med. Sinicae* 10:361.
12. Tao et al. (1989) "A prospective, controlled, double blind, cross-over study of *Tripterygium wilfordii* Hook F in the treatment of rheumatoid arthritis" *Chinese Med. J.* 102(5):327.
13. (1982) "$T_2$ Study Group of Jiang Su Province of China: Summary of the clinical trials of $T_2$ in the treatment of 554 patients with various diseases." *Annals Chinese Acad. Med.* Sci. 3:3.
14. Yu, Dy Y. (1983) "Clinical observation of 144 cases of rheumatoid arthritis treated with glycoside of radix *Tripterygium wilfordii*" *J. Trad. Chinese Med.* 3(2):125.
15. Xue, Z. (1984) "Treatment of 21 cases of systemic lupus erythematosus (SLE) with *Tripterygium wilfordii*" *Chinese J. Derm* 17 (3):201.
16. (1979) "$T_2$ Study Group of Chinese Institute of Dermatology: Clinical observation on the treatment of skin disorders with polyglycoside of *Tripterygium wilfordii*" *Acta. Acad. Med. Sinicae* 1(2):6.
17. Xie, D. (1983) "Experience in the treatment of Behcet's disease with polyglycosides of *Tripterygium wilfordii* Hook" Zhong Xi Yi Jie HE ZA Zhi 3 (6): 349.
18. Peng, S. (1983) "Report on 20 patients with Henoch-Schonlein purpura treated with polyglycosides of *Tripterygium wilfordii* Hook ($T_2$)" Jian Su Yi Yao 11:38.
19. Peng, B. (1985) "Observation on the effect of polyglycosides of *Tripterygium wilfordii* Hook ($T_2$) on 50 cases of leprosy reactive status" *Chinese Clin. Derm. J.* 4:211.
20. Wu, Y. (1986) "Treatment of neuralgia of leprosy reactive status with polyglycosides of *Tripterygium wilfordii* Hook ($T_2$)" *Chinese J. Derm.* 19(4):217.
21. Jiang, X. (1982) "Exploration of the treatment of nephrotic syndrome with polyglycosides of *Tripterygium wilfordii* Hook ($T_2$)" *Chinese J. Ped* 20(4):201.

22. Li, X. (1982) "Clinical observation on the treatment of 53 cases of nephrotic syndrome with polyglycosides of *Tripterygium wilfordii* Hook ($T_2$)" *Chinese J. Ped.* 20 (4):203.

23. Qian, J. (1987) "Observation on the effect of polyglycosides of *Tripterygium wilfordii* Hook ($T_2$) on idiopathic IgA nephropathy" *Annual Meeting of Nephrology* (People's Republic of China).

24. Li, X. (1987) "Treatment of 50 cases of children's purpura nephritis with polyglycosides of *Tripterygium wilfordii* Hook" Jiang Su Yi Yao 12:644.

25. Pan, Y. (1987) "Treatment of purpura nephritis with *Tripterygium wilfordii* Hook" *Acta. Acad. Med. Sinicae* 9(6):2.

26. Cheng, R. (1988) "Observation of the therapeutic effect of polyglycosides of *Tripterygium wilfordii* Hook ($T_2$) combined with thyroid gland tablets on chronic lymphocytic thyroiditis" Zhong Xi Yi Jie He Za Zhi 8 (11):676.

27. Zheng et al. (1983) "Studies on toxicity of total glycosides in *Tripterygium wilfordii*" *Acta. Acad. Med. Sinicae* 5 (2):73.

28. Zuo et al. (1986) "Different effect of *Tripterygium reglii* on T and B cell function" *Chinese J. Immunol.* 2:232.

29. Zhang, L. S. (1986) "Inhibitory effect of celastrol on murine lymphocyte proliferation"*Acta. Pharmacol. Sinicae* 7:85.

30. Zang et al. (1986) Shanghai Yike Dalle Xueba, 13 (4):267–272.

31. Kupchan et al. (1972) *J. Am. Chem. Soc.*, 94:3194–3195.

32. Zheng et al. (1983) "Studies on pharmacological actions of total glycosides in *Tripterygium wilfordii* Hook F"*Acta. Acad. Med. Sinicae* 5:1.

33. Chang et al. (1984) "A preliminary study of the immunosuppressive activity of mixed glycosides of *Tripterygium wilfordii* Hook F" *Chinese J. Immunol.* 4:331.

34. Zheng et al. (1982) "Effect of the decoction of *Tripterygium wilfordii* Hook on immune functions" *Fujiang Med. J.* 4:222.

35. Zhang et al. (1983) "Studies on diterpenoids from *Tripterygium wilfordii*"*Acta. Acad. Med. Shanghai* 13:267.

36. Zhang et al. (1981) "Antineoplastic action of triptolide and its effect on the immunologic function in mice" *Acta. Pharmacol. Sinicae* 2(2):128.

37. Cheng, H. W. et al. (1985) "Cellular immunological study on experimental allergic encephalopathy and the exploration of the effect of *Tripterygium wilfordii* Hook on it", *Immunology Bulletin* 5 (3,4):7.

38. Zheng Jet al. (1983), Studies on toxicity of total glycosides in *Tripterygium wilfordii*. Acta Acad Med Sinicae 5(2):73.

39. Zheng, J. R. et al. (1985a), Effect of total glycosides of *Tripterygium wilfordii* on animal reproductive organs. 1. Experiments of male rats. Acta Academiae Sinicae 5(2):73.

40. Kupchan, S. M. (1976) "Novel plant-derived tumor inhibitors and their mechanisms of action" *Cancer Treatment Reports* 60:1115.

41. Hubei Cooperative Study Group of *Tripterygium wilfordii* Hook (1981), Clinical study of the extract of *Tripterygium wilfordii* hook in the treatment of rheumatoid arthritis. Wu Han Yi Xue Yuan Xue Bao 4:62, 1981.

42. Chen, Zizhen, et al. (1986), Proceedings in the study of the active compounds of *Tripterygium wilfordii* Hook F. Zong Guo Yi Yaun Yao Xue Za Zhi. 6 (9):26.

43. Chen, Zizhen, et al. (1988), Study of the active compounds and the preparation of *Tripterygium wilfordii*. Hook F. Zi Liao Hui Bian. 6–9.

44. Chen, Zizhen et al. (1985), Quantitative measurement of triptolide content in the tablets of *Tripterygium wilfordii* Hook F. Zi Liao Hui Bian.

45. Fang, Guoxin et al. (1986), Quantitative measurement of triptolide contained in the ethyl acetate extract of *Tripterygium wilfordii* Hook F and its tablets. Zhong Tao Tong Bao 11 (8):38.

46. Zhang, Yigu et al. (1983) "An experimental pathological study of intoxication by the ethyl acetate extract of Lei Gung Teng (*Tripterygium wilfordii* Hook F)", Yao Wu Yan Jiu 4:367.

47. Li, Lezhen et al. (1982), Pharmacological study of the ethyl acetate extract of *Tripterygium wilfordii* Hook F. Zhong Cao Yao 13 (4):27.

48. Hubei Cooperative Study Group of *Tripterygium wilfordii* Hook F (1979), Preliminary pharmacologic study of *Tripterygium wilfordii* Hook F. Hubei Wei Sheng 1:73.

49. Phytochemistry Study Group of Hubei Academy of Chinese Traditional Medicine and Therapy. Study of the active ingredients of *Tripterygium wilfordii* Hook F in the treatment of rheumatoid arthritis (1978), Zhong Cao Yao Tong Xum. 11:8.

50. Chen Kunchang et al. (1986), "The lactores from three wingnut (*Tripterygium wilfordii* Hook F) in Huber", Chem. Abstracts, Vol. 105:384, abstract No. 105:130886u.

51. Thiele et al. (1983), *J. Immunol.* 131:2282–2290.

52. Rosenberg, et al. (1979), *J. Immunol.* 122: 926–931.

53. Rosenstreich, et al. (1971), *J. Exp. Med.* 134:1170–1186.

54. Jelinek et al. (1986), *J. Immunol.* 136: 83–92.

55. Geppert et al. (1987), *J Immunol.* 138: 1660–1666.

56. Davis et al. (1986), *J Immunol.* 137:3758–3767.

57. Moreno et al. (1986), *J Immunol.* 136: 3579–3587.

58. Gillis et al. (1978), *J Immunol.* 120:2027–2032.

59. Splawski et al. (1986), *J Immunol.* 139:1432–1437.

60. Weiss et al. (1986) "The role of the T3/antigen receptor complex in T cell activation" *Ann. Rev. Immunol.* 4:593.

61. Remington's Pharmaceutical Sciences (1990), 18th edition.

62. Delaunois, A. L. (1973), International encyclopedia of Pharmacology and Therapeutics, Section 7, *Biostatistics in Pharmacology*, Vol. II, Pergamon Press.

63. Zalkow et al. (1988) "Macrocyclic pyrolizidine alkaloids from Senecio anonymous. Separation of a complex alkaloid extract using droplet countercurrent chromatography" *J. Nat. Prod.* 31:1520.

64. Shu, Dafeu et al. (1989), Report of 270 cases of rheumatoid arthritis treated with ethyl acetate extract of *Tripterygium wilfordii* Hook. Zhong Yao Yao Li Yu Lin Chuang, 5 (3):40.

65. Zhang, L. S. (1986), Inhibitory effect of celastrol on murine lymphocyte proliferation. Acta Phamacol Sinicae 7:85.

66. Nan Jiang Jun Ou Zong Yi Yuan (1979), Effect of T II and Huang Jiang (Po) on lymphocytes. Zi Liao Xuan Bian 10:5.

67. Kuang Yan De et al. (1988), Effect of TWH on IL-2 production and IL-2 receptor expression. Shanghai J Immunology 8(4):250.

68. Zhu Xi Yuan et al. (1988), In vitro observation on the effect of *Tripterygium hypoglaucum* hutch on immune responses. Physiological Sciences 8:417.

69. Zheng, Y. L. et al. (1982) "Effect of the decoction of *Tripterygium wilfordii* Hook on immune functions", *Fujiang Med J.* 4:222.

70. Chang, J. L. et al. (1984) "A preliminary study of the immunosuppressive activity of mixed glycosides of *Tripterygium wilfordii* Hook F." *Chinese J. Immunol.* 4:331.

71. Zheng, J. R. et al. (1985b), Effects of total glycosides of *Tripterygium wilfordii* on reproductive organs of experimental animals. II. Experiments in female rats. Acta Academiae Sinicae 7 (4):256.

72. Durand et al. (1988) *Mol. Cell Biol.* 8:1715.

73. Owaki et al. (1993) EMBO 12:4367–4373.

74. Gorman et al. (1982) *Mol. Cell Biol.* 2:1044.

75. Markar et al., *J. Lipid Research* 35:1888–1895, 1994.

76. Goodman and Gilman, *The Pharmacological Basis of Therapeutics,* 8th Ed., Gilman, A. G., Rall, T. W., Nies, A. S., and Taylor, P., Editors, Pergamon Press, pp. 1448, 1990.

77. U.S. Pat. No. 5,294,443, Lipsky et al.

What is claimed is:

1. A method of screening for a candidate substance having binding affinity for a glucocorticoid receptor comprising:

admixing a candidate substance with a glucocorticoid receptor in the presence of TwHF preparation or a glucocorticoid receptor binding component thereof; and determining binding of the candidate substance to the glucocorticoid receptor.

2. The method of claim 1 wherein the glucocorticoid receptor is from a human skin fibroblast preparation.

3. The method of claim 1 wherein the glucocorticoid receptor binding component is triptolide, tripdiolide or wilforonide.

4. The method of claim 1 wherein the glucocorticoid receptor is conjugated to a label.

5. The method of claim 1 where the label is an enzymatic, chemical, or a radioactive label.

6. The method of claim 1 where the glucocorticoid receptor is conjugated to avidin/biotin.

* * * * *